(12) United States Patent
Auerbach

(10) Patent No.: US 6,261,808 B1
(45) Date of Patent: *Jul. 17, 2001

(54) AMPLIFICATION OF NUCLEIC ACID MOLECULES VIA CIRCULAR REPLICONS

(75) Inventor: Jeffrey I. Auerbach, Rockville, MD (US)

(73) Assignee: Replicon, Inc., Rockville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/657,943

(22) Filed: Sep. 8, 2000

Related U.S. Application Data

(63) Continuation-in-part of application No. 09/188,214, filed on Nov. 9, 1998, which is a continuation of application No. 08/906,491, filed on Aug. 5, 1997, now Pat. No. 5,834,202, which is a continuation-in-part of application No. 08/595,226, filed on Feb. 1, 1996, now Pat. No. 5,733,733, which is a continuation-in-part of application No. 08/533,852, filed on Sep. 26, 1995, now Pat. No. 5,614,389, which is a continuation-in-part of application No. 08/383,327, filed on Feb. 3, 1995, now Pat. No. 5,591,609, which is a continuation-in-part of application No. PCT/US93/07309, filed on Aug. 4, 1993, which is a continuation-in-part of application No. 07/933,945, filed on Aug. 24, 1992, now abandoned, which is a continuation-in-part of application No. 07/924,643, filed on Aug. 4, 1992, now abandoned.

(51) Int. Cl.[7] .............................. C12P 19/34; C07H 21/04
(52) U.S. Cl. ..................... 435/91.1; 435/91.2; 536/23.1
(58) Field of Search ................................ 435/91.1, 91.2; 536/23.1

(56) References Cited

U.S. PATENT DOCUMENTS

| | | | |
|---|---|---|---|
| 4,582,788 | 4/1986 | Erlich | 435/6 |
| 4,673,640 | 6/1987 | Backman | 435/68 |
| 4,683,194 | 7/1987 | Saiki et al. | 435/6 |
| 4,683,202 | 7/1987 | Mullis | 435/91 |
| 4,888,274 | 12/1989 | Radding et al. | 435/6 |
| 4,959,317 | 9/1990 | Sauer | 435/172.3 |

(List continued on next page.)

FOREIGN PATENT DOCUMENTS

| | | | |
|---|---|---|---|
| 329822 | 8/1989 | (EP) . | |
| 1020534A1 | 7/2000 | (EP) | C12Q/1/68 |
| WO88/10315 | 12/1988 | (WO) . | |
| WO89/06700 | 7/1989 | (WO) . | |
| WO90/11375 | 4/1990 | (WO) . | |
| WO94/03624 | 2/1994 | (WO) . | |
| WO96/23904 | 8/1996 | (WO) . | |
| WO97/19193 | 5/1997 | (WO) | C12Q/1/68 |

OTHER PUBLICATIONS

Mullis et al., "Specific Enzymatic Amplification of DNA in Vitro: The Polymerase Chain Reaction," Cold Spring Harbor Symp. Quant. Biol. 51 :263–273 (1986).

Higuchi, "Using PCR to Engineer DNA," In: *"PCR Technology,"* Ehrlich, H. (ed.), Stockton Press, NY, 1989, pp. 61–68.

Hoess, R. et al., "The Nature of the Interaction of the P1 Recombinase Cre with the Recombining Site loxP," Cold Spring Harbor. Symp. Quant. Biol. 49 :761–768 (1984).

Hamilton, D.L. et al., "Site–Specific Recombination by the Bacteriophage P1 loxP–Cre System," *J. Molec. Biol.* 178 :481–486 (1984).

Sauer, B. "Functional Expression of the cre–lox Site–Specific Recombination System in the Yeast Saccharomyces cerevisiae," *Molec. Cell. Biol.* 7 :2087–2096 (1987).

(List continued on next page.)

*Primary Examiner*—Kenneth R. Horlick
(74) *Attorney, Agent, or Firm*—Jeffrey I. Auerbach

(57) ABSTRACT

Methods and compositions suitable for accomplishing the in vitro amplification of nucleic acid molecules via enzymatic means are provided. The preferred means employ circular rather than linear replicons. Means for producing such circular replicons from linear reactants are also provided.

19 Claims, 19 Drawing Sheets

U.S. PATENT DOCUMENTS

| | | | |
|---|---|---|---|
| 5,089,400 | 2/1992 | Meyer | 435/69.1 |
| 5,270,184 | 12/1993 | Walker et al. | 435/91.2 |
| 5,354,668 | 10/1994 | Auerbach | 435/91.1 |
| 5,455,166 | 10/1995 | Walker | 435/91.2 |
| 5,591,609 | 1/1997 | Auerbach | 435/91.2 |
| 5,614,389 | 3/1997 | Auerbach | 435/91.2 |
| 5,714,320 | 2/1998 | Kool | 435/6 |
| 5,733,733 | 3/1998 | Auerbach | 435/6 |
| 5,834,202 | 11/1998 | Auerbach | 435/6 |
| 5,854,033 | 12/1998 | Lizardi | 435/91.2 |
| 5,888,732 | 3/1999 | Hartley et al. | 435/6 |
| 6,054,274 | 4/2000 | Sampson et al. | 435/6 |
| 6,077,668 | 6/2000 | Kool | 435/6 |
| 6,096,880 | 8/2000 | Kool | 536/25.3 |
| 6,124,120 | 9/2000 | Lizardi | 435/91.2 |
| 6,143,495 * | 11/2000 | Lizardi et al. | 435/6 |

OTHER PUBLICATIONS

Sauer, B. et al. "Site–Specific DNA Recombination in Mammalian Cells by the Cre Recombinase of Bacteriophage P1," *Proc. Natl. Acad. Sci. (U.S.A.)* 85 :5166–5170 (1988).

Abremski, K. et al., "Studies on the Properties of P1 Site–Specific Recombination: Evidence for Topologically Unlinked Products Following Recombination," *Cell* 32 :1301–1311 (1983).

Hoess, R. et al., "P1 Site–Specific Recombination: Nucleotide Sequence of the Recombining Sites," *Proc. Natl. Acad. Sci. (U.S.A.)* 79 :3398–3402 (1982).

Sternberg, N. et al., "Site–Specific Recombination and Its Role in the Life Cycle of Bacteriophage P1," *Cold Spring Harbor Symp. Quant. Biol.* 45 :297–309 (1981).

Hoess, R. et al., "Interaction of the Bacteriophage P1 Recombinase Cre with the Recombining site loxP," *Proc. Natl. Acad. Sci. (U.S.A.)* 81 :1026–1029 (1984).

Abremski, K. et al., "Bacteriophage P1 Site–Specific Recombination: Purification and Properties of the Cre Recombinase Protein," *J. Molec. Biol.* 259 :1509–1514 (1984).

Abremski, K. et al., "Bacteriophage P1 Cre–loxP Site–Specific Recombination: Site–Specific DNA Topoisomerase Activity of the Cre Recombination Protein," *J. Biol Chem.* 261 :391–396 (1986.

Sauer, B. et al., "Site–Specific Insertion of DNA into a Pseudorabies Virus Vector," *Proc. Natl. Acad. Sci. (U.S.A.)* 84 :9108–9112 (1987).

Palazzolo, M.J. et al., "Phage Lambda cDNA Cloning Vectors for Subtractive Hybridization, Fusion–Protein Synthesis and Cre–loxP Automatic Plasmid Subcloning," *Gene* 88 :25–36 (1990).

Kwoh D. et al., "Transcription–Based Amplification System and Detection of Amplified Human Immunodeficiency Virus Type 1 with a Bead–Based Sandwich Hybridization Assay," *Proc. Natl. Acad. Sci. (U.S.A.)* 86 :1173 (1989).

Ohara, O. et al., "One–Sided Polymerase Chain Reaction: The Amplification of cDNA," *Proc. Natl. Acad. Sci. (U.S.A.)* 86 :5673–5677 (1989).

Frohman, M.A., "RACE: Rapid Analysis of cDNA Ends," In: *PCR Protocols: A Guide to Methods and Applications* Academic Press, NY (1990).

Wu, D.Y. et al., "The Ligation Amplification Reaction (LAR)—Amplification of Specific DNA Sequences Using Sequential Rounds of Template–Dependent Ligation," *Genomics* 4 :560 (1989).

Mullis, K.B. et al., "Specific Synthesis of DNA in Vitro via a Polymerase–Catalyzed Chain Reaction," In: *Met. Enzymol.* 155 :335–350 (1987).

Walker, G.T. et al., "Isothermal in vitro Amplification of DNA by a Restriction Enzyme/DNA Polymerase System," *Proc. Natl. Acad. Sci. (U.S.A.)* 89 :392–396 (1992).

Chatterjee, D.K. et al., "Cloning and Overexpression of the Gene Encoding Bacteriophage T5 DNA Polymerase," *Gene* 97 :13–19 (1991).

Gillin, F. et al., "Control of Mutation frequency by Bacteriophage T4 DNA Polymerase: I. The CB120 Antimutator DNA Polymerase is Defective in Strand Displacement," *J. Biol. Chem* 251 :5219–5224 (1976).

Kolodner, R. et al., "Gene 4 Protein of Bacteriophage T7: Characterization of the Product Synthesized by the T7 DNA Polymerase and Gene 4 Protein in the Absence of Ribonucleoside 5'–Triphosphates," *J. Biol. Chem* 253 :574–584 (1978).

Eki, T. et al., "Influence of Poly(ADP–ribose) Polymerase on the Enzymatic Synthesis of SV40 DNA," *J. Biol. Chem* 266 :3087–3100 (1991).

Parada, C. et al., "Transcriptional activation of pBR322 DNA can lead to Duplex DNA Unwinding Catalyzed by the *Escherichia coli* Preprimosome," *J. Biol. Chem* 264 :15120–15129 (1989).

Dattagupta, N., "Nucleic Acid Amplification Employing Transcribable Hairpin Probe," *Chem. Abstr.* 115 (10):107787g [citing European Patent Appln. 427074 A2 (May 15, 1991)].

Bellofatto, V. et al., "Generation of a Tn5 Promoter Probe and Its Use in the Study of Gene Expression in *Caulobacter crescentus*,"*Proc. Natl. Acad. Sci. (U.S.A.)* 81 :1035–1039 (1984).

* cited by examiner

C

D or or

SEQUENCE LISTING

```
<160> NUMBER OF SEQ ID NOS: 9

<210> SEQ ID NO 1
<211> LENGTH: 48
<212> TYPE: DNA
<213> ORGANISM: pBR322

<400> SEQUENCE: 1
aattcgcggc cgcataactt cgtataatgt atgctatacg aagttatg            48

<210> SEQ ID NO 2
<211> LENGTH: 48
<212> TYPE: DNA
<213> ORGANISM: pBR322
<220> FEATURE:
<221> NAME/KEY: modified_base
<222> LOCATION: (41)...(41)
<223> OTHER INFORMATION: m5c
<221> NAME/KEY: modified_base
<222> LOCATION: (44)...(45)
<223> OTHER INFORMATION: m5c
<221> NAME/KEY: modified_base
<222> LOCATION: (47)...(47)
<223> OTHER INFORMATION: m5c

<400> SEQUENCE: 2
gatccataac ttcgtatagc atacattata cgaagttatg cggccgcg            48

<210> SEQ ID NO 3
<211> LENGTH: 13
<212> TYPE: DNA
<213> ORGANISM: pBR322

<400> SEQUENCE: 3
aattcgcggc cgc                                                   13

<210> SEQ ID NO 4
<211> LENGTH: 80
<212> TYPE: DNA
<213> ORGANISM: pBR322
<220> FEATURE:
<221> NAME/KEY: modified_base
<222> LOCATION: (55)...(55)
<223> OTHER INFORMATION: methylated or phosphorthiolated
<221> NAME/KEY: modified_base
<222> LOCATION: (58)...(59)
<223> OTHER INFORMATION: methylated or phosphorthiolated
<221> NAME/KEY: modified_base
<222> LOCATION: (61)...(61)
<223> OTHER INFORMATION: methylated or phosphorthiolated

<400> SEQUENCE: 4
tatacgaagt tatggatcca taacttcgta tagcatacat tatacgaagt tatgcggccg   60
cgaattcttg aagacgaaag                                              80

<210> SEQ ID NO 5
```

```
<211> LENGTH: 70
<212> TYPE: DNA
<213> ORGANISM: pBR322

<400> SEQUENCE: 5
tatacgaagt tatgaattca taacttcgta taatgtatgc tatacgaagt tatggatcct      60
ctacgccgga                                                            70

<210> SEQ ID NO 6
<211> LENGTH: 76
<212> TYPE: DNA
<213> ORGANISM: Homo sapiens

<400> SEQUENCE: 6
tatacgaagt tatgaattca taacttcgta taatgtatgc tatacgaagt tatttcccat      60
caagccctag ggctcc                                                     76

<210> SEQ ID NO 7
<211> LENGTH: 88
<212> TYPE: DNA
<213> ORGANISM: Homo sapiens
<220> FEATURE:
<221> NAME/KEY: modified_base
<222> LOCATION: (55)...(55)
<223> OTHER INFORMATION: methylated or phosphorylated
<221> NAME/KEY: modified_base
<222> LOCATION: (58)...(59)
<223> OTHER INFORMATION: methylated or phosphorylated
<221> NAME/KEY: modified_base
<222> LOCATION: (61)...(61)
<223> OTHER INFORMATION: methylated or phosphorylated

<400> SEQUENCE: 7
tatacgaagt tatggatcca taacttcgta tagcatacat tatacgaagt tatgcggccg      60
cccaccctgt tcccttggaa cccaggta                                        88

<210> SEQ ID NO 8
<211> LENGTH: 57
<212> TYPE: DNA
<213> ORGANISM: Homo sapiens

<400> SEQUENCE: 8
ataacttcgt ataatgtatg ctatacgaag ttattaattc ttaaagcacc tgcaccg        57

<210> SEQ ID NO 9
<211> LENGTH: 65
<212> TYPE: DNA
<213> ORGANISM: Homo sapiens
<220> FEATURE:
<221> NAME/KEY: modified_base
<222> LOCATION: (36)...(36)
<223> OTHER INFORMATION: m5c
<221> NAME/KEY: modified_base
<222> LOCATION: (39)...(40)
<223> OTHER INFORMATION: m5c
<221> NAME/KEY: modified_base
<222> LOCATION: (42)...(42)
<223> OTHER INFORMATION: m5c

<400> SEQUENCE: 9
ataacttcgt atagcataca ttatacgaag ttatgcggcc gcccataact aagtaatcca      60
gaaaa                                                                 65
```

AMPLIFICATION OF NUCLEIC ACID MOLECULES VIA CIRCULAR REPLICONS

CROSS-REFERENCE TO RELATED APPLICATIONS

This application is a continuation-in-part of U.S. patent application Ser. No. 09/188,214 (filed Nov. 9, 1998), which application is incorporated herein by reference in its entirety, and which is a continuation application of U.S. patent application Ser. No. 08/906,491 (filed Aug. 5, 1997, which issued on Nov. 10, 1998, as U.S. Pat. No. 5,834,202), which application is a continuation-in-part of U.S. patent application Ser. No. 08/595,226 (filed Feb. 1, 1996; issued Mar. 31, 1998, as U.S. Pat. No. 5,733,733), which is a continuation-in-part of U.S. patent application Ser. No. 08/533,852 (filed Sep. 26, 1995; issued Mar. 25, 1997, as U.S. Pat. No. 5,614,389), which is a continuation-in-part of U.S. patent application Ser. No. 08/383,327 (filed Feb. 3, 1995; issued Jan. 7, 1997, as U.S. Pat. No. 5,591,609), which is a continuation-in-part of PCT Application No. PCT/US93/07309 (filed Aug. 4, 1993), which is a continuation-in-part of U.S. patent application Ser. No. 07/933,945, filed Aug. 24, 1992 (which application was abandoned in favor of continuation application U.S. patent application Ser. No. 08/136,405, filed Oct. 15, 1993, which issued on Oct. 11, 1994 as U.S. Pat. No. 5,354,668), which is a continuation-in-part of U.S. patent application Ser. No. 07/924,643, filed Aug. 4, 1992 (now abandoned).

FIELD OF THE INVENTION

The present invention is in the field of recombinant DNA technology. This invention is directed to a process for amplifying a nucleic acid molecule, and to the molecules, cells, and non-human transgenic animals employed and/or produced through this process.

BACKGROUND OF THE INVENTION

Assays capable of detecting the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

The usefulness of a detection assay is often limited by the concentration at which a particular target nucleic acid molecule is present in a sample. Thus, methods that are capable of amplifying the concentration of a nucleic acid molecule have been developed as adjuncts to detection assays.

One method for overcoming the sensitivity limitation of nucleic acid concentration is to selectively amplify the nucleic acid molecule whose detection is desired prior to performing the assay. Recombinant DNA methodologies capable of amplifying purified nucleic acid fragments in vivo have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

In many instances in clinical medicine and diagnostics, however, the concentration of a target species in a sample under evaluation is so low that it cannot be readily cloned. To address such situations, methods of in vitro nucleic acid amplification have been developed that employ template directed extension. In such methods, the nucleic acid molecule is used as a template for extension of a nucleic acid primer in a reaction catalyzed by polymerase.

One such template extension method is the "polymerase chain reaction" ("PCR"), which is among the most widely used methods of DNAn amplification (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; Saiki, R. et al., U.S. Pat. No. 4,683,194 and Higuchi, R. "PCR Technology," Ehrlich, H. (ed.), Stockton Press, NY, 1989, pp 61–68), which references are incorporated herein by reference).

The polymerase chain reaction can be used to selectively increase the concentration of a nucleic acid molecule even when that molecule has not been previously purified and is present only in a single copy in a particular sample. The method can be used to amplify either single- or double-stranded DNA. The essence of the method involves the use of two oligonucleotides to serve as primers for the template-dependent, polymerase mediated replication of the desired nucleic acid molecule.

The precise nature of the two oligonucleotide primers of the PCR method is critical to the success of the method. As is well known, a molecule of DNA or RNA possesses directionality, which is conferred through the 5'→3' linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a nucleotide having 5' phosphate to the 3' hydroxyl end of a nucleic acid molecule. Thus, the action of a polymerase extends the 3' end of a nucleic acid molecule. These inherent properties are exploited in the selection of the two oligonucleotide primers of the PCR. The oligonucleotide sequences of the two primers of the PCR method are selected such that they contain sequences identical to, or complementary to, sequences which flank the sequence of the particular nucleic acid molecule whose amplification is desired. More specifically, the nucleotide sequence of the Amplification Primer is selected such that it is capable of hybridizing to an oligonucleotide sequence located 3' to the sequence of the desired nucleic acid molecule that is to be amplified, whereas the nucleotide sequence of the Target Primer is selected such that it contains a nucleotide sequence identical to one present 5' to the sequence of the desired nucleic acid molecule that is to be amplified. Both primers possess the 3' hydroxyl groups which are necessary for enzyme mediated nucleic acid synthesis.

In the polymerase chain reaction, the reaction conditions must be cycled between those conducive to hybridization and nucleic acid polymerization, and those which result in the denaturation of duplex molecules. In the first step of the reaction, the nucleic acid molecules of the sample are transiently heated, and then cooled, in order to denature any double stranded molecules that may be present. The amplification and Target Primers are then added to the sample at a concentration which greatly exceeds that of the desired nucleic acid molecule. When the sample is then incubated under conditions conducive to hybridization and polymerization, the Amplification Primer will hybridize to the nucleic acid molecule of the sample at a position 3' to the sequence of the desired molecule to be amplified. If the nucleic acid molecule of the sample was initially double stranded, the Target Primer will hybridize to the complementary strand of the nucleic acid molecule at a position 3' to the sequence of the desired molecule that is the complement of the sequence whose amplification is desired. Upon addition of a polymerase, the 3' ends of the amplification and (if the nucleic acid molecule was double stranded) Target Primers will be extended. The extension of the Amplification Primer will result in the synthesis of a DNA molecule having the exact sequence of the complement of the desired nucleic acid. Extension of the Target Primer will result in the synthesis of a DNA molecule having the exact sequence of the desired nucleic acid.

The PCR reaction is capable of exponentially amplifying the desired nucleic acid sequences, with a near doubling of the number of molecules having the desired sequence in each cycle. This exponential increase occurs because the extension product of the Amplification Primer contains a sequence which is complementary to a sequence of the Target Primer, and thus can serve as a template for the production of an extension product of the Target Primer. Similarly, the extension product of the Target Primer, of necessity, contain a sequence which is complementary to a sequence of the Amplification Primer, and thus can serve as a template for the production of an extension product of the Amplification Primer. Thus, by permitting cycles of hybridization, polymerization, and denaturation, an exponential increase in the concentration of the desired nucleic acid molecule can be achieved. Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Met. Enzymol.* 155:335–350 (1987), which references are incorporated herein by reference).

PCR technology is useful in that it can achieve the rapid and extensive amplification of a polynucleotide molecule. However, the method has several salient deficiencies. First, it requires the preparation of two different primers which hybridize to two oligonucleotide sequences of the target sequence flanking the region that is to be amplified. The concentration of the two primers can be rate limiting for the reaction. Although it is not essential that the concentration of the two primers be identical, a disparity between the concentrations of the two primers can greatly reduce the overall yield of the reaction.

A further disadvantage of the PCR reaction is that when two different primers are used, the reaction conditions chosen must be such that both primers "prime" with similar efficiency. Since the two primers necessarily have different sequences, this requirement can constrain the choice of primers and require considerable experimentation. Furthermore, if one tries to amplify two different sequences simultaneously using PCR (i.e. using two sets of two primers), the reaction conditions must be optimized for four different primers.

A further disadvantage of PCR is that it requires the thermocycling of the molecules being amplified. Since this thermocycling requirement denatures conventional polymerases, it thus requires the addition of new polymerase at the commencement of each cycle. The requirement for additional polymerase increases the expense of the reaction, and can be avoided only through the use of thermostable polymerases, such as Taq polymerase. Moreover, the thermocycling requirement attenuates the overall rate of amplification because further extension of a primer ceases when the sample is heated to denature double-stranded nucleic acid molecules. Thus, to the extent that the extension of any primer molecule has not been completed prior to the next heating step of the cycle, the rate of amplification is impaired.

Other known nucleic acid amplification procedures include transcription-based amplification systems (Kwoh D. et al., *Proc. Natl. Acad. Sci. (U.S.A.)* 86:1173 (1989); Gingeras T. R. et al., PCT appl. WO 88/10315 (priority: U.S. patent applications Ser. Nos. 064,141 and 202,978); Davey, C. et al., European Patent Application Publication no. 329, 822; Miller, H. I. et al., PCT appl. WO 89/06700 (priority: U.S. patent application Ser. No. 146,462, filed Jan. 21, 1988)), and "race" (Frohman, M. A., In: PCR Protocols: A Guide to Methods and Applications, Academic Press, NY (1990)) and "one-sided PCR" (Ohara, O. et al., *Proc. Natl. Acad. Sci. (U.S.A.)* 86:5673–5677 (1989)).

Methods based on ligation of two (or more) oligonucleotides in the presence of nucleic acid having the sequence of the resulting "di-oligonucleotide", thereby amplifying the di-oligonucleotide, are also known (Wu, D. Y. et al., *Genomics* 4:560 (1989)).

An isothermal amplification method has been described in which a restriction endonuclease is used to achieve the amplification of target molecules that contain nucleotide 5'-[a-thio]triphosphates in one strand of a restriction site (Walker, G. T. et al., *Proc. Natl. Acad. Sci. (U.S.A.)* 89:392–396 (1992)).

All of the above amplification procedures depend on the principle that an end-product of a cycle is functionally identical to a starting material. Thus, by repeating cycles, the nucleic acid is amplified exponentially.

Methods that use thermocycling, e.g. PCR or Wu, D. Y. et al., *Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

SUMMARY OF THE INVENTIONS

The present invention concerns a method and in vitro polynucleotide complexes for achieving the amplification of a nucleic acid molecule using a single primer, under isothermal conditions. In detail, the invention provides a method for amplifying a target polynucleotide region of an initial linear nucleic acid molecule, which method comprises the steps of:

(A) providing a partially single-stranded, partially double-stranded nucleic acid complex, wherein a first strand of the molecule contains a polynucleotide region that is complementary in sequence to the target polynucleotide region and is a circular strand lacking termini and a second strand of the complex is non-circular and has a 3' terminus hybridized to the circular strand of the molecule; and (B) incubating the partially single-stranded, partially double-stranded nucleic acid molecule in the presence of a polymerase and under conditions sufficient to permit the polymerase to extend the 3' terminus of the non-circular strand in a template-dependent manner using the circular strand of the molecule as the template to thereby produce an extension product; wherein the template-dependent extension of the 3' terminus of the non-circular strand causes strand displacement of a portion of the non-circular strand and results in the amplification of the target polynucleotide region.

The invention is further directed to the embodiments of such method that additionally includes the step of:

(C) incubating a primer nucleic acid molecule in the presence of the extension product of step (B) under conditions sufficient to permit the polymerase to extend the 3' terminus of the primer in a template-dependent manner using the extension product formed in step (B) as the template, to thereby produce a double-stranded linear nucleic acid molecule whose strands comprise the extension product formed in step (B) and the primer extension product.

The invention is firther directed to the embodiments of such method that additionally includes the step of:

(D) causing a strand of the double-stranded linear nucleic acid molecule produced in step (C) to circularize;

(E) incubating the circularized molecule produced in step (D) with a primer oligonucleotide in the presence of a polymerase and under conditions sufficient to permit the polymerase to extend the 3' terminus of the primer in a template-dependent manner using the circular strand of the molecule produced in step (D) as the template, wherein the template-dependent extension of the 3' terminus of the primer oligonucleotide causes strand displacement of a portion of the oligonucleotide and results in the amplification of the target polynucleotide region.

The invention is further directed to the embodiments of such methods wherein the non-circularized strand of the nucleic acid molecule contains a modified nucleotide (such as a ribonucleotide or a biotinylated nucleotide) and/or wherein the target polynucleotide region contains a mammalian gene or a polynucleotide portion thereof.

The invention is further directed to an in vitro polynucleotide complex comprising a first, second and third strand of DNA, wherein the first strand is circular and lacks termini and the second and third strands are non-circular and possess termini; wherein a 3' terminal region of the second strand is complementary to a region of the circular first strand, and is hybridized thereto, and a non-3' terminal region of the second strand is complementary to a region of the third strand, and is hybridized thereto.

The invention also provides an in vitro polynucleotide complex comprising at least a first, a second, and a third strand of DNA, wherein:

the first strand is circular and lacks termini;

the second strand is non-circular, and possesses a 3' terminal region that is complementary to a region of the circular first strand, and is hybridized thereto; and the third strand is non-circular, and possesses a 3' terminal region that is complementary to a region of the second strand and is hybridized thereto.

The invention particularly concerns such in vitro polynucleotide complexes wherein at least one of the first, second or third strands of DNA contains a modified nucleotide (such as a biotinylated nucleotide or a ribonucleotide), and/or wherein the DNA strand containing the modifiedl nucleotide is a non-circularized DNA strand of the complex.

The invention further particularly concerns such in vitro polynucleotide complexes wherein a DNA strand of the complex contains a nucleotide sequence of a mammalian gene or a polynucleotide portion thereof.

The invention further particularly concerns such in vitro polynucleotide complexes wherein the hybridized 3' terminus of the second DNA strand is extended via a template-dependent polymerase reaction.

BRIEF DESCRIPTION OF THE FIGURES

FIG. 8A shows the twin origin "rolling circle" replicon that results from the extension of two primers during the amplification of a single-stranded circular molecule. FIG. 8B shows the θ ("theta") and "rolling circle" replicons that result from the amplification of a double-stranded circular molecule.

In FIG. 11, the 5' fourth region of Primer I that is complementary to a portion of the proto-Lox site may be deleted, if desired.

In FIG. 12, the 5' fourth region of Primer I that is complementary to a portion of the proto-Lox site may be deleted, if desired.

DETAILED DESCRIPTION OF THE INVENTION

I. Terminology of the Invention

Figure 1:
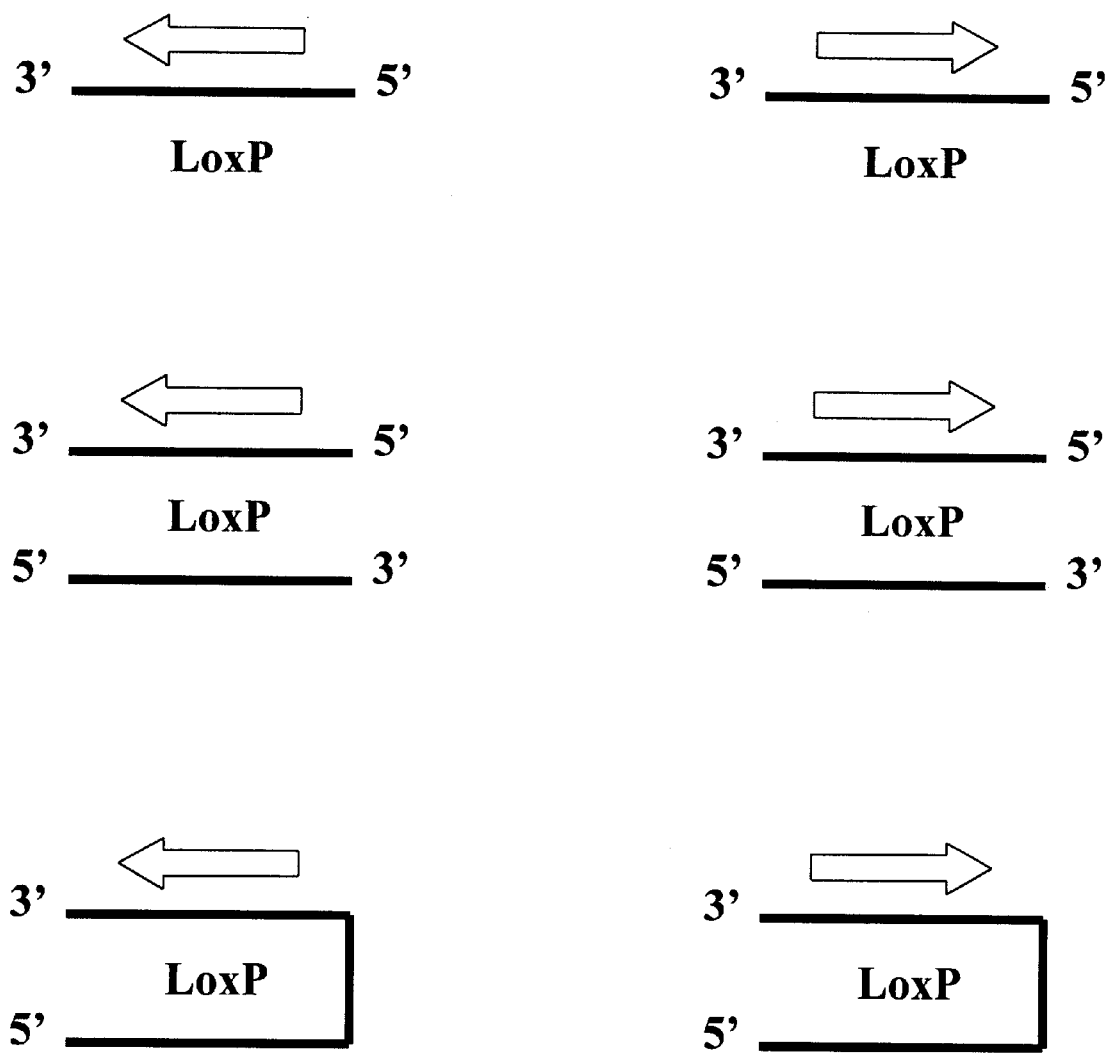
FIG. 1 shows examples of suitable 5' adaptor molecules.

The present invention provides a method for amplifying a "target" polynucleotide region of a nucleic acid molecule that is present in a sample. Such samples may include biological samples derived from a human or other animal source (such as, for example, blood, stool, sputum, mucus, serum, urine, saliva, teardrop, a biopsy sample, an histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

As used herein, the term "desired" nucleic acid molecule is intended to refer to the nucleic acid molecule that is to be amplified by the present methods. The "desired" molecule can have been purified, or partially purified, or may be present in an unpurified state in the sample. A nucleic acid molecule that contains the "desired" molecule is said to be a "target" molecule. The nucleic acid molecules of the present invention are described as "polynucleotides" in order to denote that they contain more than three nucleotide residues. The nucleic acid molecules of the present invention are further described as comprising "regions," in order to more fully describe the structural components of the molecules. The linear nucleic acid molecules of the invention contain terminal "portions." As used herein, such portions define a region at the end of the molecules.

As used herein, the term "amplification" refers to a "template-dependent process" that results in an increase in the concentration of a nucleic acid molecule relative to its initial concentration. As used herein, the term "template-dependent process" is intended to refer to a process that involves the template-dependent extension of a primer molecule. As such, the term amplification, as used herein, is intended to exclude in vivo vector-mediated propagation of the type described by Cohen et al. (U.S. Pat. No. 4,237,224); Maniatis, T. et al., (*Molecular Cloning A Laboratory Manual,* Cold Spring Harbor Laboratory, 1982), etc. The term "template dependent process" refers to nucleic acid synthesis of RNA or DNA wherein the sequence of the newly synthesized strand of nucleic acid is dictated by the well-known rules of complementary base pairing (see, for example, Watson, J. D. et al., *In: Molecular Biology of the Gene,* 4th Ed., W. A. Benjamin, Inc., Menlo Park, Calif. (1987)). As used herein, a sequence of one nucleic acid molecule is said to be the "complement" of another if it contains a T (or U), A, C, or G at a position in which the other molecule contains an A, T (or U), G or C, respectively.

The present invention employs a variety of different enzymes to accomplish the amplification of the desired nucleic acid molecule. A "polymerase" is an enzyme that is capable of incorporating nucleotides to extend a 3' hydroxyl terminus of a "primer molecule." A nucleotide that has been incorporated into a nucleic acid molecule is termed a nucleotide "residue." As used herein, a "primer" or "primer molecule" is a nucleic acid molecule, that when hybridized to a nucleic acid molecule, possesses a 3' hydroxyl terminus that can be extended by a polymerase. Polymerase enzymes are discussed in Watson, J. D. et al., *In: Molecular Biology of the Gene,* 4th Ed., W. A. Benjamin, Inc., Menlo Park, Calif. (1987), which reference is incorporated herein by reference, and similar texts. Examples of DNA polymerases that can be used in accordance with the methods described herein include *E. coli* DNA polymerase I, the large proteolytic fragment of *E. coli* DNA polymerase I, commonly known as "Klenow" polymerase, "Taq" polymerase, T7 polymerase, T4 polymerase, T5 polymerase, reverse transcriptase, etc.

Polymerases exhibiting processivity (the capacity to continue the extension of a particular primer to thereby produce an extension product of significant length) are preferred.

In several of the embodiments of the present invention, amplification is achieved by extending a hybridized primer on a single-stranded DNA template that is base paired to itself. Thus, polymerases capable of mediating such primer extension and strand displacement are particularly preferred. Examples of preferred polymerases include T5 DNA polymerase (Chatterjee, D. K. et al., *Gene* 97:13–19 (1991), T4 polymerase, and T7 polymerase. Where a DNA polymerase does not displace a base-paired stand of a DNA molecule and extend a primer into the previously base-paired region with sufficient efficiency, such capacity may be facilitated by the addition of an accessory protein. For example, the capacity of T7 polymerase to displace a strand of a base-paired molecule is enhanced by the presence of T7 gene 4 protein (Kolodner, R. et al., *J. Biol. Chem* 253:574–584 (1978)). Similarly, T4 DNA polymerase can catalyze extensive primer extension if the reaction additionally contains T4 gene 32 protein (Gillin, F. D. et al., *J. Biol. Chem* 251:5219–5224 (1976)). Use of the T7 promoter and gene 4 protein, however, has the advantage that the gene 4 protein is used catalytically rather than stoichiometrically during the primer extension reaction.

In some embodiments of the invention, amplification is achieved by extending a hybridized primer on a DNA template of a double-stranded DNA molecule composed of two separable strands. Thus, in such embodiments, polymerases capable of mediating such primer extension are preferred. Examples of preferred polymerases include those cited above. The capacity to extend primer molecules using such double-stranded DNA templates may be facilitated through the addition of topisomerases and/or gyrases (Eki, T. et al., *J. Biol. Chem* 266:3087–3100,1991); Parada, C. A. et al., *J. Biol. Chem* 264:15120–15129 (1989)).

When an enzymatic reaction, such as a polymerization reaction, is being conducted, it is preferable to provide the components required for such reaction in "excess" in the reaction vessel. "Excess" in reference to components of the amplification reaction refers to an amount of each component such that the ability to achieve the desired amplification is not substantially limited by the concentration of that component.

A "ligase" is an enzyme that is capable of covalently linking the 3' hydroxyl group of a nucleotide to the 5' phosphate group of a second nucleotide. Ligases capable of joining "blunt ended" or "staggered ended" double-stranded nucleic acids, may be employed. Examples of suitable ligqses include *E. coli* DNA ligase, T4 DNA ligase, etc.

The present invention employs a "recombinase," and most preferably, a "site-specific recombinase." As used herein, a recombinase is an enzyme whose action on two nucleic acid molecules results in recombination between the two molecules. Recombination is a well-studied natural process which results in the scission of two nucleic acid molecules having identical or substantially similar (i.e. "homologous") sequences, and the reformation of the two molecules such that one region of each initially present molecule becomes ligated to a region of the other initially present molecule (Sedivy, J. M., *Bio-Technol.* 6:1192–1196 (1988), which reference is incorporated herein by reference). Recombinases are naturally present in both prokaryotic and eucaryotic cells (Smith, G. R., In: *Lambda II,* (Hendrix, R. et al., Eds.), Cold Spring Harbor Press, Cold Spring Harbor, N.Y., pp. 175–209 (1983), herein incorporated by reference)).

Two types of recombinational reactions have been identified. In the first type of reaction, "general" or "homologous" recombination, any two homologous sequences can be recognized by the recombinase (i.e. a "general recombinase"), and can thus act as substrates for the reaction. In contrast, in the second type of recombination, termed "site-specific" recombination, the recombinase can catalyze recombination only between certain specialized "recombinational sites." Thus, in "site-specific recombination," only homologous molecules having a particular sequence may act as substrates for the reaction.

Site specific recombination is thus mediated by a site-specific recombinase acting on two "recombinational sites." Several such site-specific recombination systems have been described. The most preferred site-specific recombinational system is the site-specific recombination system of the *E. coli* bacteriophage P1. The P1 bacteriophage cycles between a quiescent, lysogenic state and an active, lytic state. The bacteriophage's site-specific recombination system catalyzes the circularization of P1 DNA upon its entry into a host cell. It is also involve in the breakdown of dimeric P1 DNA molecules which may form as a result of replication or homologous recombination.

The P1 site-specific recombination system catalyzes recombination between specialized "recombinational sites" known as "lox" sites (e.g., "loxP," "loxB" etc.). The loxP site is the preferred lox site of the present invention has been shown to consist of a double-stranded 34 bp sequence. This sequence contains two 13 bp inverted repeated sequences which are separated from one another by an 8 bp spacer region (Hoess, R. et al., *Proc. Natl. Acad. Sci. (U.S.A)* 79:3398–3402 (1982); Sauer, B. L., U.S. Pat. No. 4,959,317, herein incorporated by reference).

The recombination of lox sites is mediated by a P1-encoded protein known as "Cre" (Hamilton, D. L. et al., *J. Molec Biol.* 178:481–486 (1984), herein incorporated by reference). The Cre protein mediates recombination between two loxP sequences (Stemberg, N. et al., *Cold Spring Harbor Symp. Quant. Biol.* 45:297–309 (1981)). These sequences may be present on the same DNA molecule, or they may be present on different molecules. Cre protein has a molecular weight of 35,000. The protein has been purified to homogeneity, and its reaction with the loxP site has been extensively characterized (Abremski, K. et al., *J. Molec. Biol.* 259:1509–1514 (1984), herein incorporated by reference). The cre gene (which encodes the Cre protein) has been cloned (Abremski, K. et al., *Cell* 32:1301–1311 (1983), herein incorporated by reference).

Plasmids producing Cre may be obtained from Life Technologies, Inc. (Gaithersburg, Md.). Cre protein is available from Novogen, Inc. (Madison, Wis.).

Any protein that is capable of mediating recombination between two lox sites is the functional equivalent of Cre protein. Any nucleotide sequence that can be recombined with a lox sequence by Cre is the functional equivalent of a lox site.

The site specific recombination catalyzed by the action of Cre protein on two lox sites is dependent only upon the presence of the above-described lox sites and Cre. No energy is needed for this reaction; thus, there is no requirement for ATP or other similar high energy molecules. Moreover, no factors or proteins other than the Cre protein is required in order to mediate site-specific recombination at lox sites (Abremski, K. et al., *J. Molec. Biol. Chem.* 259:1509–1514 (1984)). In vitro, the reaction is highly efficient; Cre is able to convert 70% of the DNA substrate into products and it appears to act in a stoichiometric manner (Abremski, K. et al., *J. Molec. Biol. Chem.* 259:1509–1514 (1984)).

Cre-mediated recombination can occur between lox sites which are present on two different molecules. Because the internal spacer sequence of the loxP site is asymmetrical, two loxP sites exhibit directionality relative to one another (Hoess, R. H. et al., *Proc. Natl. Acad. Sci. (U.S.A.)* 81:1026–1029 (1984)). If the loxP sites are in the same relative orientation, Cre acts to excise and circularize the DNA between them. If the sites are in an opposite relative orientation, Cre acts to flip the DNA between them. The recombinational event works efficiently on linear or circular molecules (Abremski, K. et al., *Cell* 32:1301–1311 (1983); Abremski, K. et al., *J. Molec. Biol. Chem.* 261:391–396 (1986)).

The nature of the interaction between Cre and lox sites has been extensively studied (Hoess, R. P. et al., *Cold Spring. Harb. Symp. Quant. Biol.* 49:761–768 (1984), herein incorporated by reference). In particular, mutations have been produced both in Cre, and in the lox site.

The Cre mutants thus far identified have been found to catalyze recombination at a much slower rate than that of the wild-type Cre protein. lox mutants have been identified which recombine at lower efficiency than the wild-type site (Abremski, K. et al., *J. Molec. Biol. Chem.* 261:391–396 (1986); Abremski, K. et al., *J. Molec. Biol.* 202:59–66 (1988), herein incorporated by reference).

Experiments with mutant lox sites in which either the left or right inverted repeat had been removed, has revealed that Cre is capable of binding to partial loxP sites, but is incapable of mediating efficient recombination between such sites. Insertions in the spacer region impair the ability of Cre to catalyze recombination. Of particular interest to the present invention is the use of a loxP511 mutant site.

The Cre protein is capable of mediating lox-specific recombination in eucaryotic hosts, such as *Saccharomyces cerevisiae* (Sauer, B., *Molec. Cell. Biol.* 7:2087–2096 (1987); Sauer. B. L., U.S. Pat. No. 4,959,317, herein incorporated by reference), or mammalian cells (Sauer, B. et al., *Proc. Natl. Acad. Sci. (U.S.A.)* 85:5166–5170 (1988), Sauer, B. et al., *Nucleic Acids Res.* 17:147–161 (1989), both references herein incorporated by reference).

Significantly, the lox-Cre system can mediate site-specific recombination between lox sites separated by extremely large numbers of nucleotides (Sauer, B. et al., *Gene* 70:331–341 (1988); Stemberg, N., *Proc. Natl. Acad. Sci. (U.S.A.)* 87:103–107 (1990); Sauer, B. et al., *Proc. Natl. Acad. Sci.* (U.S.A.) 84:9108–9112 (1987); Palazzolo, M. J. et al., *Gene* 88:25–36 (1990), all herein incorporated by reference).

It has been found that certain *E. coli* enzymes inhibit efficient circularization of linear molecules which contain two lox sites. Hence, enhanced in vivo circularization efficiency can be obtained through the use of E. coli mutants which lack exonuclease V activity (Sauer, B. et al., *Gene* 70:331–341 (1988)).

Although the Cre-lox site-specific recombination system is preferred, alternative site-specific recombination systems have been identified, and can be used in accordance with the methods of the present invention.

For example, the site-specific recombination system of the *E. coli* bacteriophage X (Weisberg, R. et al., In: *Lambda II,* (Hendrix, R. et al., Eds.), Cold Spring Harbor Press, Cold Spring Harbor, N.Y., pp. 211–250 (1983), herein incorporated by reference) can be employed. Bacteriophage λ uses its recombinational system in order to integrate its genome into its host, the bacterium *E. coli*. The system is also employed to excise the bacteriophage from the host genome in preparation for virus' lytic growth.

The λ recombination system is composed of four proteins- Int and Xis, which are encoded by the bacteriophage, and two host integrative factors encoded by the *E. coli*. These proteins catalyze site-specific recombination between "att" sites.

The λ Int protein (together with the *E. coli* host integration factors) will catalyze recombination between "attP" and "attB" sites. If the attP sequence is present on a circular molecule, and the attB site is present on a linear molecule, the result of the recombination is the disruption of both att sites, and the insertion of the entire attP-containing molecule into the attB site of the second molecule. The newly formed linear molecule will contain an attL and art attR site at the termini of the inserted molecule.

The λ Int enzyme is unable to catalyze the excision of the inserted molecule. Thus, the reaction is unidirectional. In the presence of the λ Xis protein, the reverse reaction can proceed, and a site-specific recombinational event will occur between the attR and attL sites to regenerate the initial molecules.

The nucleotide sequence of both the Int and Xis proteins are known, and both proteins (as well as the host integrative factors) have been purified to homogeneity. Both the integration and the excision reaction can be conducted in vitro (Better, M.; Wickner, S.; Auerbach, J. and Echols, H., *Cell* 32:161–168 (1983)). The nucleotide sequences of the four att sites has also been determined (Weisberg, R. et al., In: *Lambda II*, (Hendrix, R. et al., Eds.), Cold Spring Harbor Press, Cold Spring Harbor, N.Y., pp. 211–250 (1983), which reference has been herein incorporated by reference).

Additional site-specific recombination systems that may be employed include Tpnl and the β-lactamase transposons (Levesque, R. C., *J. Bacteriol.* 172:3745–3757 (1990)); the Tn3 resolvase (Flanagan, P. M. et al., *J. Molec. Biol.* 206:295–304 (1989); Stark, W. M. et al., *Cell* 58:779–790 (1989)); the yeast recombinases (Matsuzaki, H. et al., *J. Bacteriol.* 172:610–618 (1990)); the *B. subtilis* SpoIVC recombinase (Sato, T. et al., *J. Bacteriol* 172:1092–1098 (1990)); the Flp recombinase (Schwartz, C. J. et al., *J. Molec. Biol.* 205:647–658 (1989); Parsons, R. L. et al., *J. Biol. Chem.* 265:4527–4533 (1990); Golic, K. G. et al., *Cell* 59:499–509 (1989); Amin, A. A. et al., *J. Molec. Biol.* 214:55–72 (1990)); the Hin recombinase (Glasgow, A. C. et al., *J. Biol. Chem.* 264:10072–10082 (1989)); immunoglobulin recombinases (Malynn, B. A. et al., *Cell* 54:453–460 (1988)); and the Cin recombinase (Hafter, P. et al., *EMBO J.* 7:3991–3996 (1988); Hubner, P. et al., *J. Molec. Biol.* 205:493–500 (1989)), all herein incorporated by reference. Such alternate systems are discussed by Echols, H. (*J. Biol. Chem.* 265:14697–14700 (1990)), de Villartay, J. P. (*Nature* 335:170–174 (1988); Craig, N. L. (*Ann. Rev. Genet.* 22:77–105 (1988)), Poyart-Salmeron, C. et al. (*EMBO J.* 8:2425–2433 (1989)), Hunger-Bertling, K. et al. (*Molec. Cell. Biochem.* 92:107–116 (1990)), and Cregg, J. M. (*Molec. Gen. Genet.* 219:320–323 (1989)), all herein incorporated by reference.

Conditions or agents which increase the rate or the extent of priming, primer elongation, or strand displacement, may be used to increase the extent of the amplification obtained with the methods of the present invention. For instance, as indicated above, the addition of topoisomerases, helicases, gyrases or single-stranded nucleic acid binding proteins (such as the gene 32 protein of T4 or the gene 4 protein of T7) may be used to increase the strand displacement rate of a DNA polymerase, or may allow the use of a DNA polyrnerase that might not ordinarily give substantial amplification.

It is desirable to provide to the assay mixture an amount of required co-factors such as $Mg^{++}$, and dATP, dCTP, dGTP, TTP, ATP, CTP, GTP, UTP or other nucleotides in sufficient quantity to support the degree of amplification desired. Nucleotide analogues, etc. (Piccirilli, J. A. et al., *Nature* 343:33–37 (1990)) can be substituted or added to those specified above, provided that the base pairing, polymerase and strand displacing functions are not adversely affected to the point that the amplification does not proceed to the desired extent.

II. The Molecules Employed in the Amplification Method

A. The Nature of the Target Molecule

The methods of the present invention may be used to amplify any desired target nucleic acid molecule. Such molecules may be either DNA or RNA. The molecule may be homologous to other nucleic acid molecules present in the sample (for example, it may be a fragment of a human chromosome isolated from a human cell biopsy, etc.).

Alternatively, the molecule may be heterologous to other nucleic acid molecules present in the sample (for example, it may be a viral, bacterial, or fungal nucleic acid molecule isolated from a sample of human blood, stools, etc.). The methods of the invention are capable of simultaneously amplifying both heterologous and homologous molecules. For example, amplification of a human tissue sample infected with a virus may result in amplification of both viral and human sequences.

The present methods do not require that the desired target molecule have any particular sequence or length. In particular, the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Mycoplasma, etc.), eucaryotic (for example, protozoans (such as amoebas, etc.), parasites (such as Plasmodium, and Trypanosomes), fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the desired target nucleic acid sequence need not be found in Nature.

The target nucleic acid molecule which is to be amplified may be in either a double-stranded or single-stranded form. If the nucleic acid is double-stranded at the start of the amplification reaction it may be first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, DC (1985)), which references are herein incorporated by reference. Such treatment permits the obtained single-stranded molecules to be amplified using the recombinational-site-containing primer molecules described below. Alternatively, double-stranded target molecules may be ligated into circular or linear double-stranded molecules that contain recombinational sites.

Single-stranded RNA, double-stranded RNA or MRNA are also capable of being amplified by the method of the invention. For example, the RNA genomes of certain viruses can be converted to DNA by reaction with enzymes such as reverse transcriptase (Maniatis, T. et al., *Molecular Cloning (A Laboratory Manual)*, Cold Spring Harbor Laboratory, 1982; Noonan, K. F. et al., *Nucleic Acids Res.* 16:10366 (1988)). The product of the reverse transcriptase reaction may then be amplified according to the invention.

The complete nucleotide sequence of the desired molecule need not be known in order to employ the methods of the present invention. The present invention requires knowledge only of the sequences that flank the sequence that is to be amplified. The target polynucleotide that is to be amplified may thus be envisioned as consisting of three regions. The first region, corresponding to the 3' terminus of the desired molecule that is to be amplified is the region to which the single-primer of the present invention hybridizes, or to which double-stranded ligation adaptors are added. Thus, the sequence of this first region must be ascertained in order to construct a complementary primer that would be capable of hybridizing to the desired molecule.

As used herein, two nucleic acid molecules are said to be able to hybridize to one another if their sequences are complementary and they are thus capable of forming a stable anti-parallel double-stranded nucleic acid structure. Conditions of nucleic acid hybridization suitable for forming such double stranded structures are described by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, DC (1985)). For the purpose of the present invention, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

The size of the first region of the target molecule is such as to permit a primer molecule to stably hybridize to it. Preferably, therefore, the first region of the desired molecule will be greater than 10 nucleotides in length, and most preferably, 15 to 50 nucleotides in length. Longer or shorter primers may be used, however. The use of shorter primers may result in the amplification of nucleic acid sequences in addition to that of the desired sequence. The use of longer primers may slow the rate of hybridization. Extension of the primer may be done with reverse transcriptase where the desired molecule is present as RNA Alternatively, such extension can be accomplished with other DNA polymerases where the desired molecule is DNA. If the first region is not used as a template for a primer, it need not be of a length sufficient to permit stable priming.

The second region of the desired molecule is located 5' to the first region, and consists of the central portion of the desired molecule. The second region of the desired molecule may have any sequence, and be of any length. As stated above, the sequence of this region need not be known in order to follow the methods of the present invention. Typically, the second region may extend from a few nucleotides to several kilobases.

The third region of the desired molecule is located at the 5' terminus of the desired molecule. The sequence of this region must be known in order to follow the methods of the present invention. Typically, the third region may extend from as few as 3 nucleotides to 10–20. If the third region is not used as a template for a primer, it need not be of a length sufficient to permit stable priming. In a preferred embodiment, however, the third region must be of sufficient length to permit stable hybridization to occur. In this embodiment, the third region is preferably of a length of 15 to 50 nucleotides in length. Longer or shorter primers may be used, however.

Thus, the extent of sequence information of the desired molecule that is needed to practice the present invention is typically less than that needed to practice PCR methods.

B. The Nature of the Single Primer

In its most preferred embodiments, the present invention employs a single primer to achieve the amplification of the desired molecule. This single primer is also referred to herein as an "Amplification Primer," in order to distinguish it from other primers that optionally may be employed. The single primer molecule is of suitable length to stably hybridize to the first region of tic desired molecule. Primer molecules of 10–50 nucleotides are thus suitable. In a most preferred embodiment, the primer molecule will comprise from 3' terminus to 5' terminus:

(1) a first polynucleotide region complementary to the 3' terminus of the target polynucleotide region;

(2) a second polynucleotide region containing modified nucleotides (especially methylated nucleotides or ((x-thio)phosphorothioate nucleotides, wherein, if the second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains the modified nucleotides; and (3) a third polynucleotide region, wherein, if the third polynucleotide region were hybridized to a complementary polynucleotide, a double-stranded polynucleotide would thereby be formed that would contain a recombinational site (especially a lox site);

The nucleotide sequence of the second polynucleotide region of the Amplification Primer may be selected from any of a wide variety of sequences that, if hybridized to a complementary polynucleotide, would form a double-stranded polynucleotide that would contain one or more restriction endonuclease sites. All that is desired is that the restriction endonuclease(s) that recognizes the contained site(s) be substantially incapable of cleaving a strand of a nucleic acid molecule that contains the modified nucleotides and that the contained site(s) not be present in the target polynucleotide that is to be amplified (i.e., that the second polynucleotide region of the Amplification Primer not be complementary to any portion of the target polynucleotide).

In a highly preferred sub-embodiment, the single primer will additionally contain a fourth polynucleotide region, the fourth polynucleotide region of the Amplification Primer molecules being located 5' to the third polynucleotide region of the Amplification Primer molecules, and having a nucleotide sequence complementary thereto, such that the third and fourth polynucleotide regions of the Amplification Primer molecules are hybridized to one another forming a complete or (more preferably) a partial recombinational site.

Any of a variety of methods can be used to produce the primer molecule. For example, the molecule can be excised from a vector that contains it using suitable enzymes, such as restriction enzymes. Most preferably, however, the primer will be made synthetically, using well-known. chemical methods. Since the lox site is the most preferred recombinational site of the present invention, the following description illustrates the invention by reference to the lox recombinational site. It will, however, be recognized that any of the above-described recombinational sites may be alternatively employed.

C. The Adaptor Molecules of the Invention

The above-described single primer is preferably employed in concert with a target polynucleotide that has been adapted to be a part of a circular double-stranded DNA molecule that comprises: (a) a lox site; (b) the target polynucleotide region; and (c) a hemi-modified restriction site located between the target polynucleotide region and the lox site, wherein one strand of the hemi-modified restriction contains modified nucleotides (especially methylated nucleotides and (α-thio)- phosphorothioate nucleotides), such that a restriction endonuclease that recognizes such restriction site will be incapable of cleaving that strand containing the modified nucleotides, but will cleave that stand lacking modified bases (or vice versa). The target polynucleotide will be present in that strand of the hemi-modified site that is cleaved by the restriction endonuclease.

Figure 11:
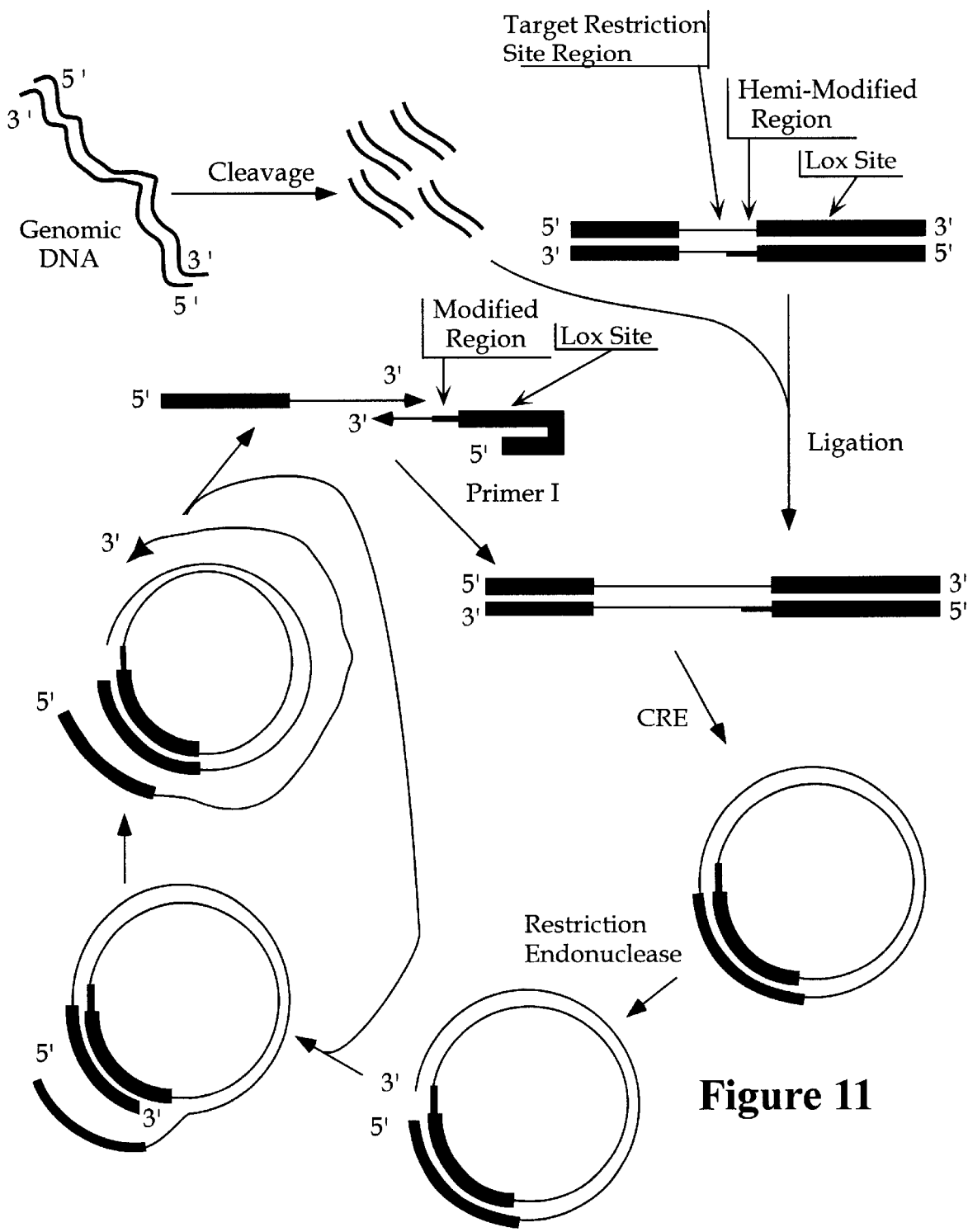
FIG. 11 provides a diagramatic representation of the use of ligation to form double-stranded circular molecules, as described in Example 2.
Figure 12:
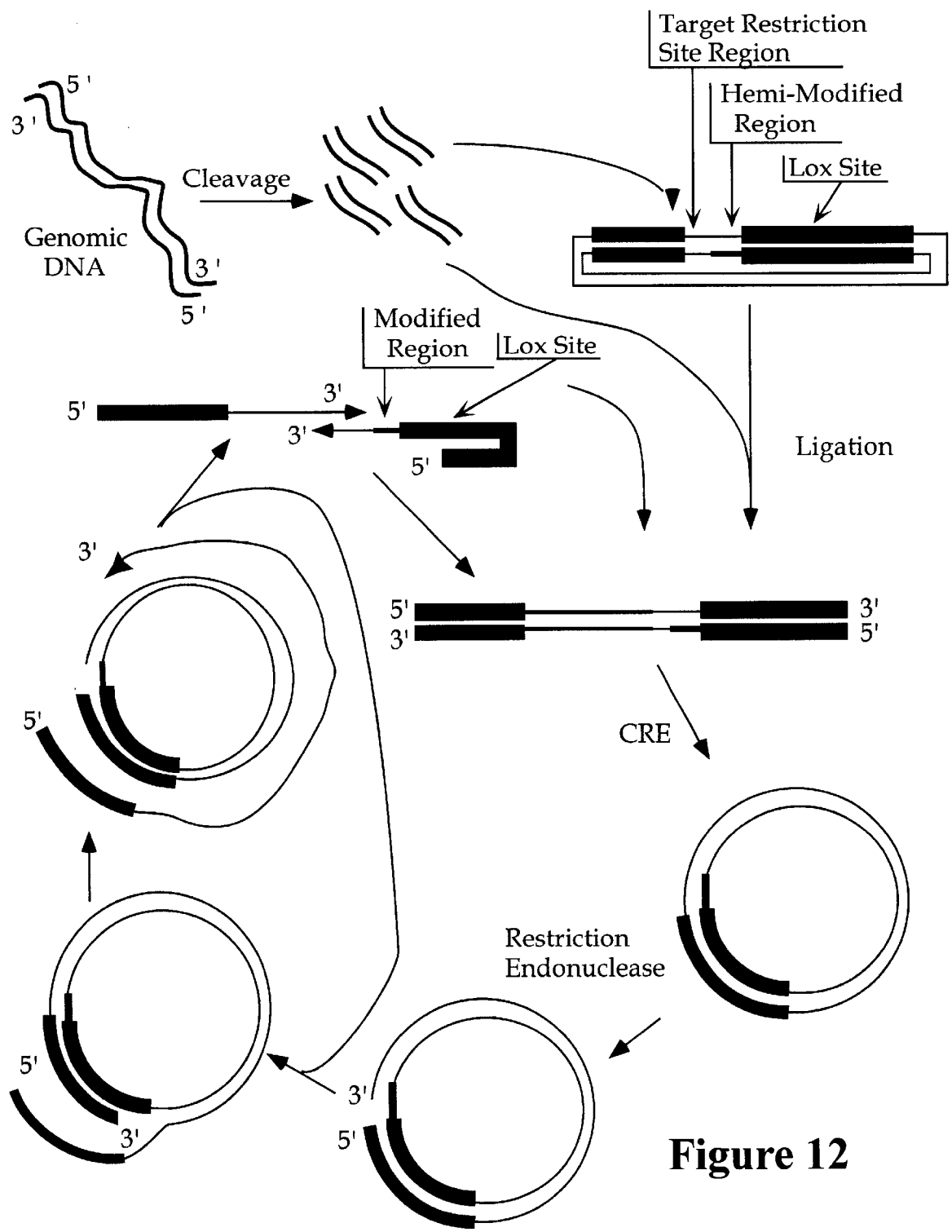
FIG. 12 provides a diagramatic representation of an alternative use of ligation to form double-stranded circular molecules, as described in Example 2.

Such a double-stranded circular molecule can be obtained in any of a variety of ways (see FIGS. 11 and 12). In one embodiment, a circular double-stranded DNA precursor molecule comprising: (a) a lox site; (b) a target restriction endonuclease cleavage site; and (c) a hemi-modified restriction site located between the target restriction endonuclease cleavage site and the lox site will be employed. The target polynucleotide is introduced (e.g., via target restriction site cleavage and ligation) into such a circular precursor molecule in order to form the desired double-stranded circular molecule. In employing such a circular precursor molecule, the molecule's lox site must be oriented (3'→5') opposite to the orientation of the single primer (such that if that strand of the desired circular molecule that lacks modified nucleotides were linearized by cleavage at the hemi-modified restriction site, and were hybridized to the single primer, primer extension of the linearized molecule would yield a linear double-stranded molecule having a lox site at each end that would be in direct orientation with respect to one another (see, FIG. 11).

In an alternative embodiment, such a double-stranded circular molecule is obtained via Cre-mediated recombination of a linear double-stranded DNA molecule that comprises: (a) a first lox site located at a first end of the linear molecule, (b) a second lox site located at a second end of the linear molecule, wherein the first and the second lox sites are directly oriented with resperct to one another so as to permit the Cre to mediate the circularization of the linear double-stranded molecules, and to thereby form the double-stranded circular molecule; (c) the target polynucleotide region located internal to the first and second lox sites; and (d) a hemi-modified restriction site located between the target polynucleotide region and one of the lox sites, wherein one strand of the hemi-modified restriction site of each of the linear molecules contains modified nucleotides (especially methylated nucleotides and (α-thio)phosphorothioate nucleotides), such that a restriction endonuclease that recognizes such restriction site will be incapable of cleaving that strand containing the modified nucleotides (see, FIG. 12).

In a sub-embodiment, such a linear molecule may be obtained by inserting the target polynucleotide into a target restriction endonuclease site of a precursor double-stranded inear nucleic acid molecule that comprises: (a) a first lox site located at a first end of the linear molecule, (b) a second lox site located at a second end of the linear molecule, wherein the first and the second lox sites are directly oriented with respect to one another so as to permit the Cre to mediate the circularization of the linear double-stranded molecules, and to thereby form the double-stranded circular molecule; (c) a target restriction endonuclease cleavage site; and (d) a hemi-modified restriction site located between the target restriction site and one of the lox sites.

In alternative embodiments, such linear molecules may be obtained using one or more specialized "adaptor molecules." Such adaptor molecules alter the 3' and 5' termini of the target molecule in oder to install the lox sites and hemi-modified restriction site onto the target molecule.

Such adaptor molecules may be either partially single-stranded, partially double-stranded nucleic acid molecules, completely single-stranded or completely double-stranded molecule. Thus, in one embodiment, the adaptation of the 5' terminus is accomplished by employing a primer molecule whose 5' terminus is designed such that it contains the desired adaptation. In a second embodiment, the 5' terminus of the primer extension product is altered (e.g., via ligation) using a 5' adaptor molecule. With respect to the alteration of the 3' terminus of the primer extension product, such alteration can be accomplished using either a single adaptor molecule, or, in an alternate embodiment with a pair of adaptor molecules having similar structure (and resulting in a mixture of primer extension products, some of which have been modified by one of the 3' adaptor molecules, and some of which have been modified by the other 3' adaptor molecule). Thus, for example, a linear double-stranded nucleic acid molecule containing the desired sequence may be incubated in the presence of ligase and double-stranded nucleic acid adaptor molecules so as to cause the adaptation of both ends of the linear molecule. Alternatively, such adaptation may be accomplished using primers and a polymerase-mediated primer extension reaction. In a third alternative, a combination of ligation (to adapt one end of the linear nucleic acid molecule containing the desired sequence) and primer extension (to adapt the linear molecule's other end) may be employed.

The adaptor molecules permit the linear molecule to form either single-stranded or double-stranded circular nucleic cold molecules which may be readily amplified under isothermal conditions.

1) Illustrative Adaptor Molecules of the 5' Terminus

Any of a variety of adaptor molecules may be used to modify the 5' terminus of the primer molecule or the primer extension product such that it contains a recombinational site, most preferably a lox site.

The adaptor molecule of the 5' terminus can be added to the primer molecule either before or after its template dependent extension. In the most preferred embodiment, a primer molecule is employed that has been modified to contain the 5' adaptor molecule. Thus, in this embodiment, the primer may be synthesized such that it contains an additional region (including the recombinational site) at its 5' terminus. If desired, when employing a recombinational site that, like lox exhibits directionality, some of the primer may be synthesized with the lox site in one orientation, and some of the primer synthesized with the lox site in the opposite orientation. Alternatively, 5' adaptor primer molecules that all have their recombinational site in a single orientation can be used in conjunction with 3' adaptor molecules that contain their recombinational site in an appropriate orientation.

Alternatively, however, the 5' terminus can be modified through the action of a ligase using either single-stranded or, more preferably, double-stranded DNA containing the recombinational site. In one embodiment, such ligation substrates will possess a 5' terminus (such as a 5' hydroxyl group) that prevents the ligation of more than one such ligation substrate molecule to the primer extension molecule. Alternatively, the adaptor molecule may be a single-stranded molecule, that exhibits intra-strand hybridization (i.e. a "hairpin" loop). As in the case of the adapted primer molecule discussed above, the use of a recombinational site having directionality will generally require the use of two hairpin loop species having opposite orientations for their recombinational sites. Alternatively, one may ligate a double-stranded molecule having the above-described attributes of the single-stranded 5' adaptor to one end of the linear double-stranded molecules of the sample. Additional sequences may, if desired, be added 3' or 5' of the recombinational site. Examples of suitable 5' adaptor molecules are shown in FIG. 1.

2) Illustrative Adaptor Molecules of the 3' Terminus

Figure 2A:
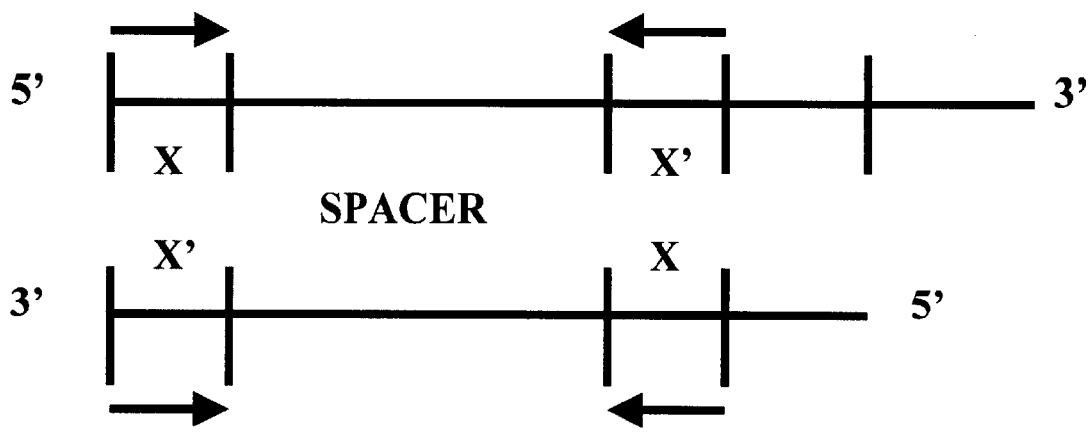
FIGS. 2A and 2B (comprising Drawings A,B,C and D) show examples of suitable 3' adaptor molecules.
Figure 2A:
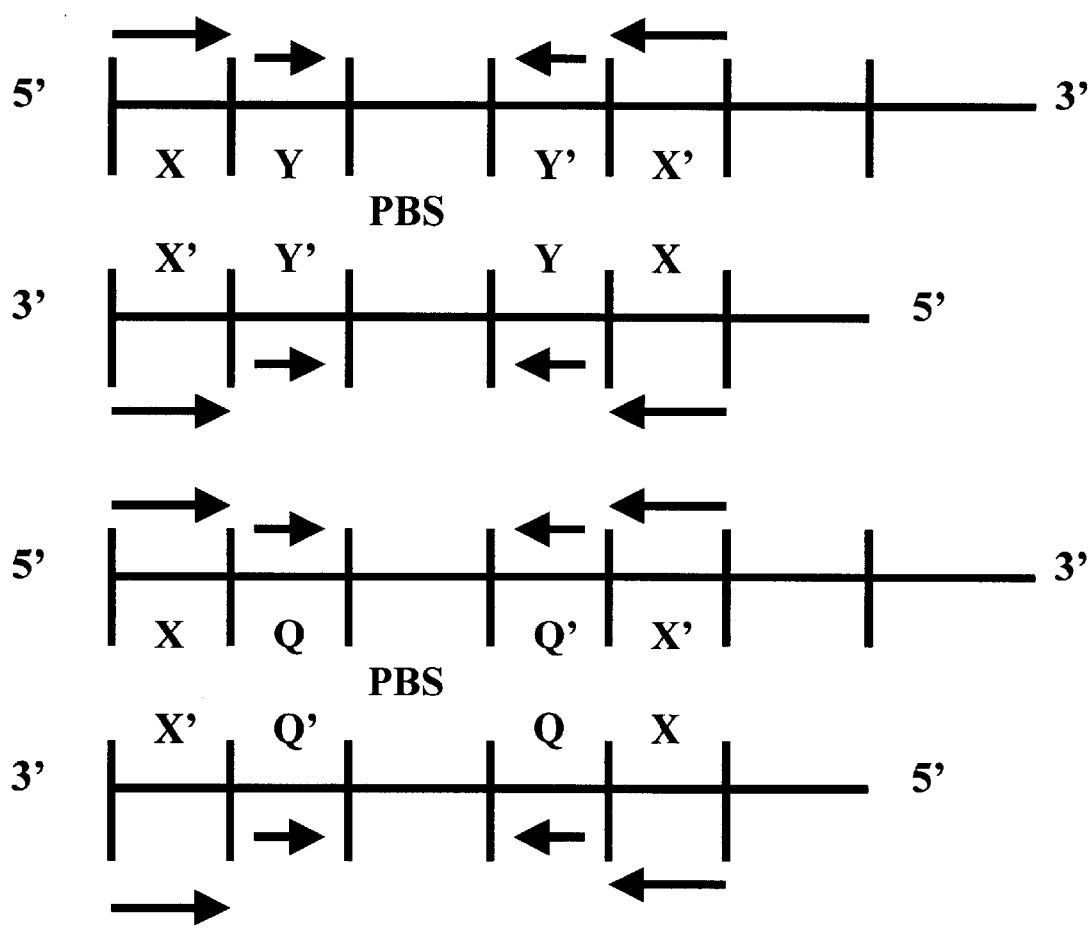
Figure 2B:
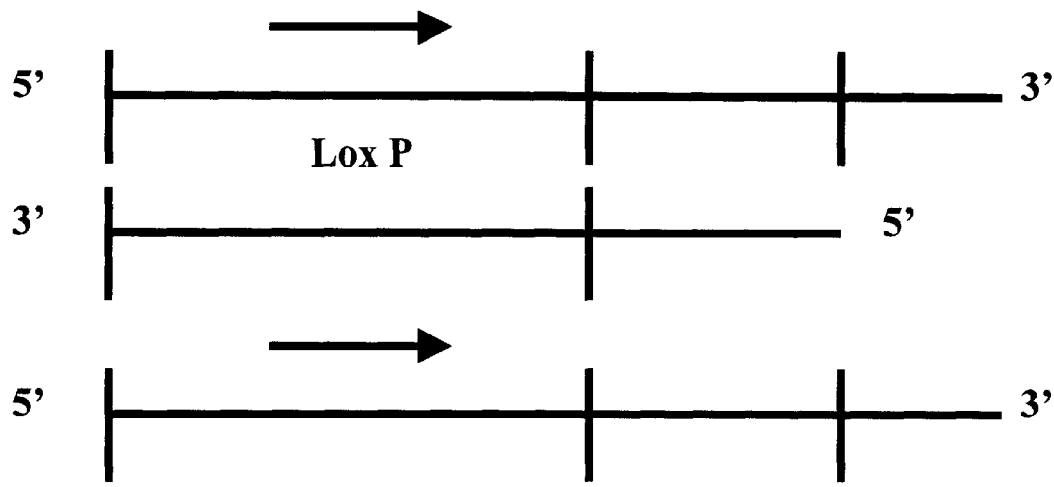
Figure 2B:
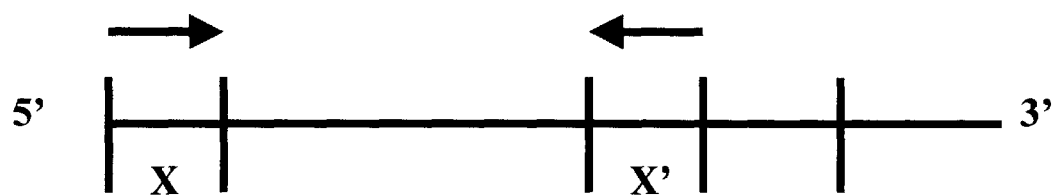
Figure 2B:
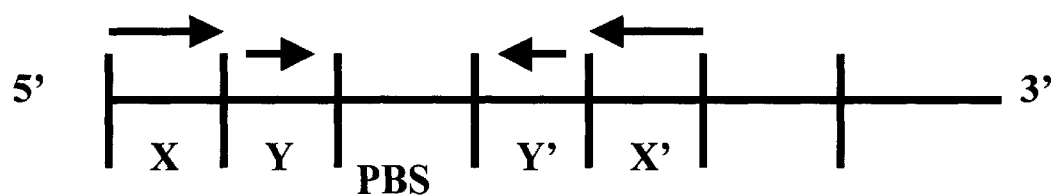
Figure 2B:
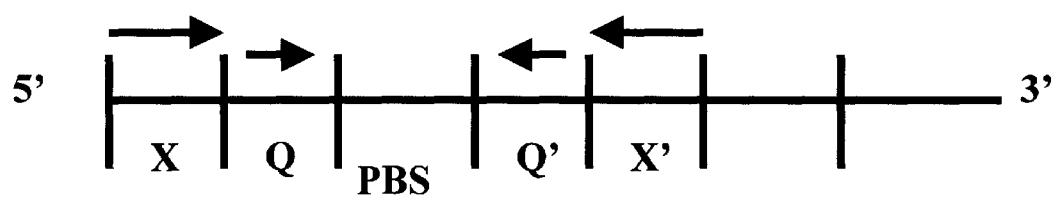

Any of a variety of different adaptor molecules can be used to alter the 3' terminus of the primer extension molecule. The choice of which type of adaptor molecule to use will depend upon whether the formation of single-stranded or double-stranded molecules is preferred. Examples of suitable 3' adaptor molecules are shown in FIGS. 2A and 2B.

a) Adaptor Molecules for the Formation of Single-Stranded Circular Molecules: Use of Partially Single-Stranded and Partially DoubleStranded 3' Adaptor Molecules In one embodiment, a partially single-stranded and partially double-stranded nucleic acid adaptor molecule is employed to alter the 3' terminus of the primer extension product as a prelude to the formation of single-stranded circular molecules. A feature of such molecules is that they possess a 3' protruding region having a predefined sequence. The sequence of this protruding sequence is selected such that 3'-most portion of the region has the same sequence as that of the third region of the desired molecule. In a first preferred sub-embodiment, this protruding terminus is blocked, as by the use or presence of a dideoxynucleotide, etc., such that it is incapable of being extended by a polymerase in a template-directed process.

The strand of the adaptor molecule that contains the 3' protruding sequence may be composed of RNA, such that it can be readily degraded by the inclusion of RNAse to the reaction, or by alkali treatment. Methods of forming RNA oligonucleotides are disclosed by Sharmeen, L. et al. (*Nucleic Acids Res.* 15:6705–6711 (1987)) and by Milligan, J. F., et al., *Nucleic Acids Res.* 15:8783–8798 (1987)). In another embodiment, the strand of the adaptor molecule that contains this protruding sequence is composed of a nucleic acid that has been biotinylated, such that the strand can be selectively removed from the reaction by addition of agents such as anti-biotin antibodies, avidin, streptavidin, etc.

A second feature of the adaptor molecules is the presence of a double-stranded region located 5' to the above-described protruding 3' terminus.

In one embodiment, the invention employs a single such 3' terminus adaptor molecule whose double-stranded region comprises a pair of inverted repeated sequences, preferably separated by a spacer sequence. This aspect of the invention is shown in FIG. 2A (Drawing A), wherein the terms X and X' are used to designate complementary sequences that comprise the inverted repeated sequence. The spacer sequence is preferably 3–100 nucleotides in length. The length of the spacer is selected such that the inverted repeated sequences are sterically capable of hybridizing to one another. Thus, if the inverted repeated sequences are of sufficient length, the sequences will be capable of hybridizing to one another in the absence of a spacer sequence. In a preferred embodiment, however, the spacer sequence is 10–50 nucleotide long, and preferably not an inverted repeated sequence. In this embodiment, the spacer sequence is adapted to function as a primer binding site (designated "PBS" in the Figures) for the amplification of the desired sequence.

In an alternate preferred embodiment, the invention employs two different 3' terminus adaptor molecules. In each of these adaptor molecules, the spacer sequence is composed of a second pair of inverted repeated sequences, such that the structure of the adaptor molecule provides a pair of external inverted repeated sequences that flank a pair of internal inverted repeated sequences. In a preferred embodiment, the sequences of the pair of internal inverted repeated sequences are interrupted by a primer binding site that is preferably 10–50 bases long, and preferably not an inverted repeated sequence. This aspect of the invention is shown in FIG. 2A (Drawing B) and FIG. 2B (Drawing D), where the term "PBS" is used to designate the relative position of the optional primer binding site, the terms Y and Y' or Q and Q' are used to designate complementary sequences that comprise the optional internal inverted repeated sequences, and the terms X and X' are used to designate complementary sequences that comprise the external inverted repeated sequences. In the most preferred sub-embodiment of this embodiment, the sequences of the external and internal repeated sequences are different. The sequences of the two adaptor molecules are selected such that the nucleotide sequence of the external inverted repeat sequence of the first of the two adaptor molecules is different from the external inverted repeated sequence of the second of the two adaptor molecules. The sequences of the external inverted repeats of the first and second adaptor molecules are thus selected such that they are substantially incapable of hybridizing to one another (i.e. the external repeat sequence of the first adaptor molecule is substantially incapable of hybridizing to the external inverted repeat of the second adaptor molecule). The nucleotide sequence of the internal inverted repeated sequences of the two adaptor molecules is preferably the same, or at least sufficiently similar to allow the respective internal repeated sequences of the adaptor molecules to hybridize to one another. If the internal repeated sequences are inter. opted by a primer binding site, such sequences may be different, but will preferably be the same.

As used herein, two sequences are said to be "inverted repeats" of one another if they are complementary to one another. Similarly, an "inverted repeat sequence" is composed of two oligonucleotide or polynucleotide sequences ("arms") which are complimentary to one another. Thus, a feature of the adaptor molecules is that, although the inverted repeat sequences of the two strands of the double-stranded region of the adaptor molecules are hybridized to one another in the adaptor molecule, they would be capable of intra-strand hybridization (i.e. "snapping-back" and forming a hairpin loop structure) if the adaptor molecule were denatured or converted to a single-stranded form. The length of the inverted repeated sequences is selected such that intra-strand hybridization would be possible if the adaptor molecule were denatured or converted to a single-stranded form. Thus, the inverted repeated sequences are preferably greater than 10 nucleotides in length, and most preferably, 15 to 50 or more nucleotides in length. Longer or shorter inverted repeated sequences may however be used. The use of shorter inverted repeated sequences may result in a decreased rate of hairpin formation. The use of longer sequences may lead to a destablization of inter-strand hybridization, and thus may be undesirable where such hybridization is desired.

When defining conditions to be used in any specific embodiment of the present invention, it is desirable to select a primer that cannot prime on itself. To minimize the likelihood of potential interfering reactions, candidate primers should be tested in reactions which address this issue prior to use in the amplification process. One such example is to measure the addition of nucleotides by a polymerase to the 3' end of the candidate primer in the absence of any target molecule.

The above-described adaptor molecules can be synthesized using any of a variety of methods. For example, the "inverted repeated sequence-inverted repeated sequence," "inverted repeated sequence-spaccr sequence-inverted repeated sequence" or the "external inverted repeated sequence-internal inverted repeated sequence-internal inverted repeated sequence-external inverted repeated sequence" segment of the adaptor molecules can be obtained by cloning such a sequence, propagating the vector, and then excising the sequence using a restriction endonuclease. The protruding 3' terminus can be formed using deoxynucleotide terminal transferase and the appropriate nucleotide triphosphates. In following such a method, it would be desirable to block the 3' terminus of the second strand of the adaptor molecule. Alternatively, the protruding 3' terminus can be added by ligating a single- or double-stranded molecule to the "inverted repeat-inverted repeat" segment of the adaptor molecule (or any of the above-described variants thereof), and then removing the seqlience complementary to the "protruding 3' sequence" to thereby render that sequence actually protruding.

In a preferred embodiment, the strands of the adaptor molecule(s) are prepared separately (preferably by primer extension using suitable primers and templates, or by clonal propagation, by transcription, by synthetic means, or by any combination of these methods), and then mixed together under conditions sufficient to permit the molecules to hybridize to one another. This method is particularly suited to the embodiments wherein the strand that contains the protruding 3' end is RNA or is biotinylated. Those of ordinary skill will readily comprehend alternative methods for forming the adaptor molecules.

b) Adaptor Molecules for the Formation of Single-Stranded Circular Molecules: Use of Single-Stranded 3' Adaptor Molecules In a second, and preferred, sub-embodiment, the adaptor molecule(s) in the formation of single-stranded circular molecules will be single-stranded DNA (preferably biotinylated) or RNA molecules. Such molecules will have a sequence and structure that are identical to the structure of the that strand of the above-described partially single-stranded and partially double-stranded adaptor molecules which contain the discussed protruding 3' terminus. In the most preferred embodiment, the 3' terminus of the molecule is blocked, such that it cannot be extended by a polymerase.

3) Adaptor Molecules for the Formation of Double-Stranded Circular Molecules

The above-described 3' adaptor molecules are designed to permit the formation of single-stranded circular molecules. In order to form double-stranded circular molecules, a different type of 3' adaptor molecule is preferably employed.

In this embodiment of the invention, the 3' terminus of the primer extension product is modified such that it contains a recombinational site. If a site such as lox is employed, the orientation of the site must be such that upon adaptation, the two lox sites are present in a direct repeat orientation. For such purpose, a partially single-stranded and partially double-stranded adaptor molecule or a single-stranded molecule is employed. The partially single-stranded and partially double-stranded adaptor molecule will have a protruding 3' terminus that is capable of hybridizing to the primer extension product in the manner described above, and of being extended in a template-dependent manner. The double-stranded region of the molecule, located 5' to the protruding 3' terminus, will comprise a recombinaLional site. Most preferably, the double-stranded region will also contain a region that is substantially incapable of participating in inter-strand hybridization flanked by sequences that are capable of participating in such hybridization. Most preferably, such incapacity is obtained through the use of sequences that are identical, and have the attributes of the primer binding sequence discussed above. Such a molecule is illustrated in FIG. 2B (Drawing C). If a single-stranded 3' terminus adaptor molecule is employed, the molecule will preferably contain the same structure and sequence as that strand of the above-described partially single-stranded and partially double-stranded adaptor molecule that possess the protruding 3' terminus. Alternatively, one may ligate a double-stranded molecule having the above-described attributes of the single-stranded 3' adaptor to one end of the linear double-stranded molecules of the sample.

D. The Amplification Substrates

The present invention employs amplification substrate molecules in order to achieve the amplification of the desired molecule.

Any of a variety of amplification substrates may be employed. In one embodiment, such substrates are either the primer molecule used to form the primer extension product (i.e., a 5' adaptor primer (either containing or lacking the 5' recombinational site) or a sequence complementary to that of the optional primer binding site of the 3' terminus adaptor molecule. Most preferably, the substrate is a primer that contains the 5' adaptor molecule (including a recombinational site). The above-described single primer is the most preferred amplification substrate.

III. Illustrative Amplification Methods of the Present Invention

A. Primer Extension Method

1. The First Step of the Method

In the first step of one embodiment of the amplification methods of the present invention, the nucleic acid molecules of the sample are incubated with the above-described single primer molecule in the presence of DNA polymerase, and requisite nucleotide triphosphates and co-factors. The molecules are incubated under conditions sufficient to permit the primer to hybridize to its target sequence, and to be extended to form a primer extension product. Thus, if the desired sequence is a double-stranded DNA or RNA molecule, the strands are separated as by heat denaturation, or other means. If the desired sequence is a single-stranded DNA or RNA molecule, the denaturation step may be omitted.

In one sub-embodiment of the invention, as for example when the concentration of the desired molecule is anticipated to be low, the molecules can be denatured and renatured in a cyclical manner so as to permit repeated rounds of primer extension. In this embodiment, the use of theii-ilostable polymerases, such as Taq polymerase is preferred, so that the expense of adding new polymerase can be avoided.

Most preferably, the conditions of the primer extension will be controlled such that the average length of the extended single primers will be the length separating the beginning of the first region from the end of the third region of the desired molecule. Such controlling of conditions can be accomplished by altering the concentration of DNA polymerase, the duration of the polymerization reaction, or by limiting the concentration of a nucleotide triphosphate such that "stuttering" of the primer extension product occurs when it reaches the desired average length.

After single primer extension has been completed, the reaction is treated, preferably with heat or RNAse H the target molecule was RNA) so as to denature double-stranded nucleic acid molecules and render such molecules single-stranded. If desired, excess primer can be removed from the sample (as by filtration, adsorption, etc.), however, such action is not necessary to the invention.

2. The Second Step of the Methods: Adaptation of the 3' Terminus of the Primer Extension Product The second step of this embodiment of the method entails the adaptation of the primer extension product such that it is capable of conversion into a circular molecule. The adaptation of the 3' terminus may precede or follow the adaptation of the 5' terminus, depending upon the adaptor molecules selected. Adaptation of the termini may also be accomplished simultaneously. As indicated, the adaptation of the 5' terminus may be accomplished through the use of modified primers, and may thus be accomplished prior to the primer extension step.

a) Further Primer Extension

Figure 3A:
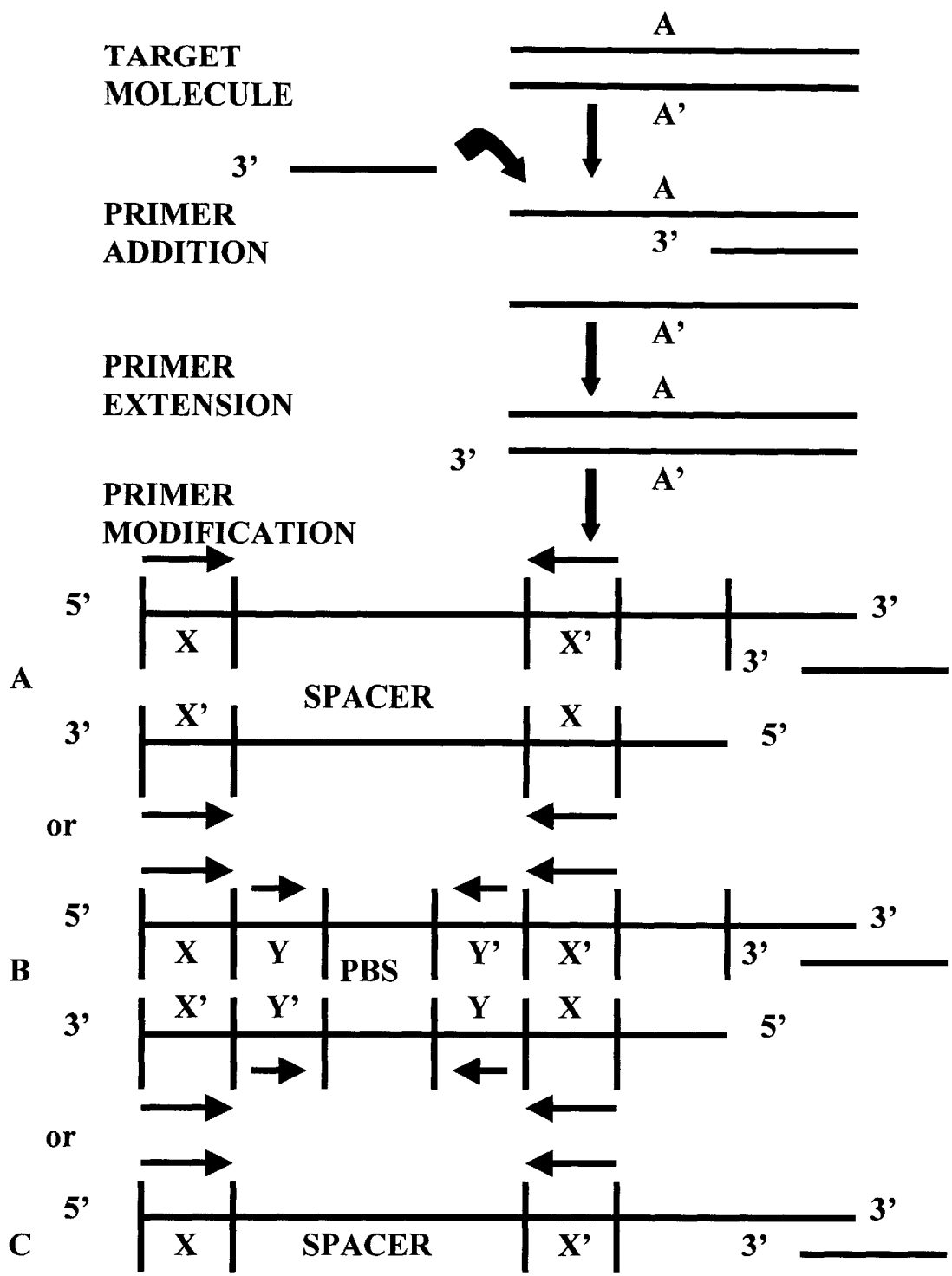
FIGS. 3A and 3B show the adaptation of the 3' terminus of the primer extension product. Lines A, B and C of FIG. 3A illustrate the use of different adaptor molecules to modify the 3' terminus of the primer extension product through further primer extension. Line D of FIG. 3B shows the use of ligation to modify the 3' terminus.

In a first and preferred sub-embodiment employing either the partially single-stranded/partially double-stranded 3' adaptor molecule(s) or the single-stranded 3' adaptor molecule(s), the adaptation of the 3' terminus of the primer extension product is accomplished through the further template-mediated extension of the primer extension products (FIG. 3A, lines A, B, C). Most preferably, the adaptor molecules used in this embodiment will contain blocked 3' termini.

In this embodiment, the primer extension products, which have been rendered single-stranded, are permitted to hybridize to the adaptor molecules. As indicated above, the molecules have regions of homology sufficient to permit the primer extension products to hybridize to the adaptor molecule.

Regardless of which type of adaptor molecule(s) is employed, the further extension of the primer extension products results in the formation of a partially-double-stranded and partially single stranded molecule. The molecule is characterized in possessing a protruding 5' terminus whose sequence comprises that of the primer extension product. If the adaptor molecule was partially double-stranded, the further extension of the primer extension product causes the displacement or destruction of the strand that was initially complementary to the template.

b) Ligation

Figure 3B:
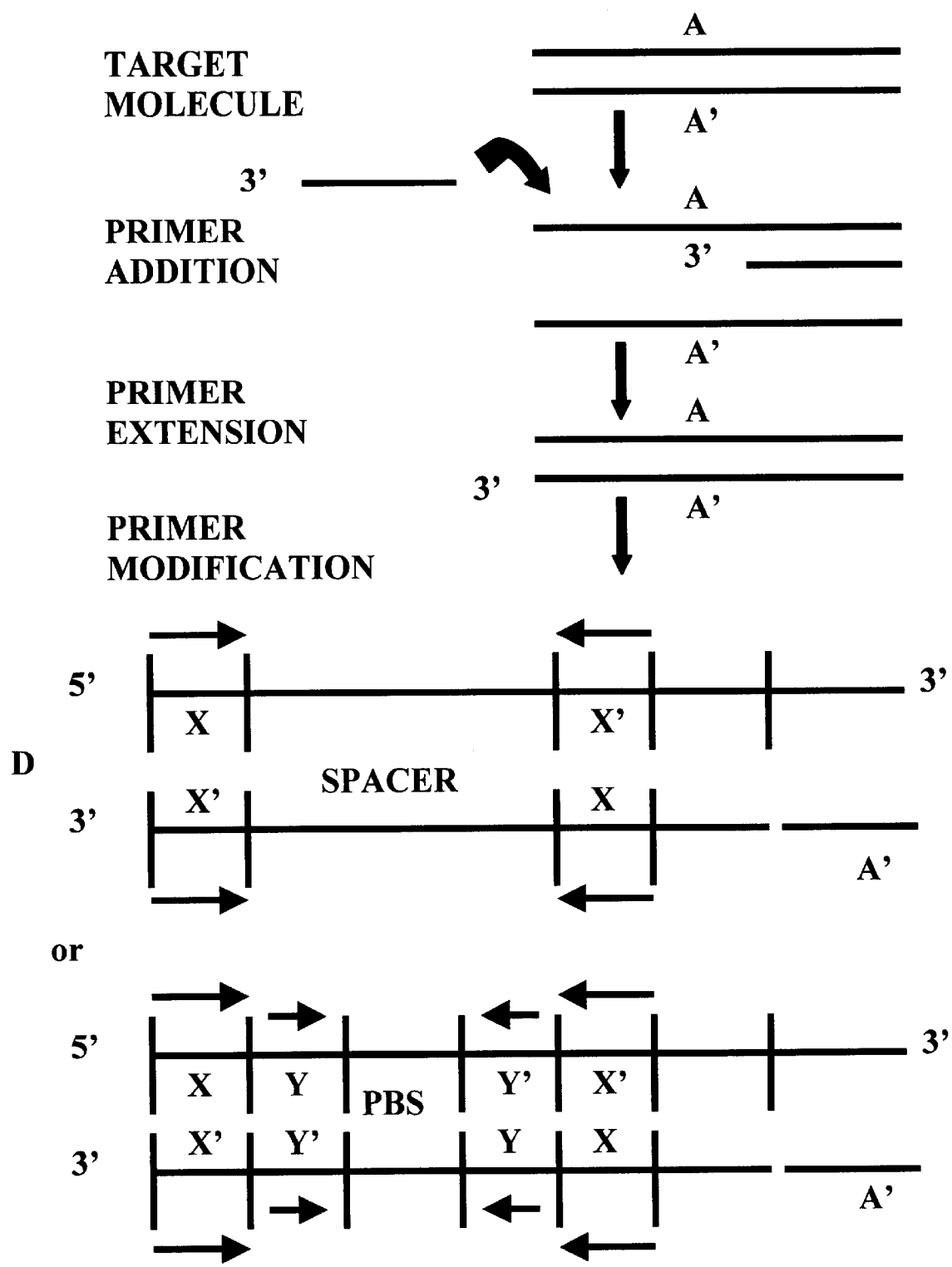
Figure 4A:
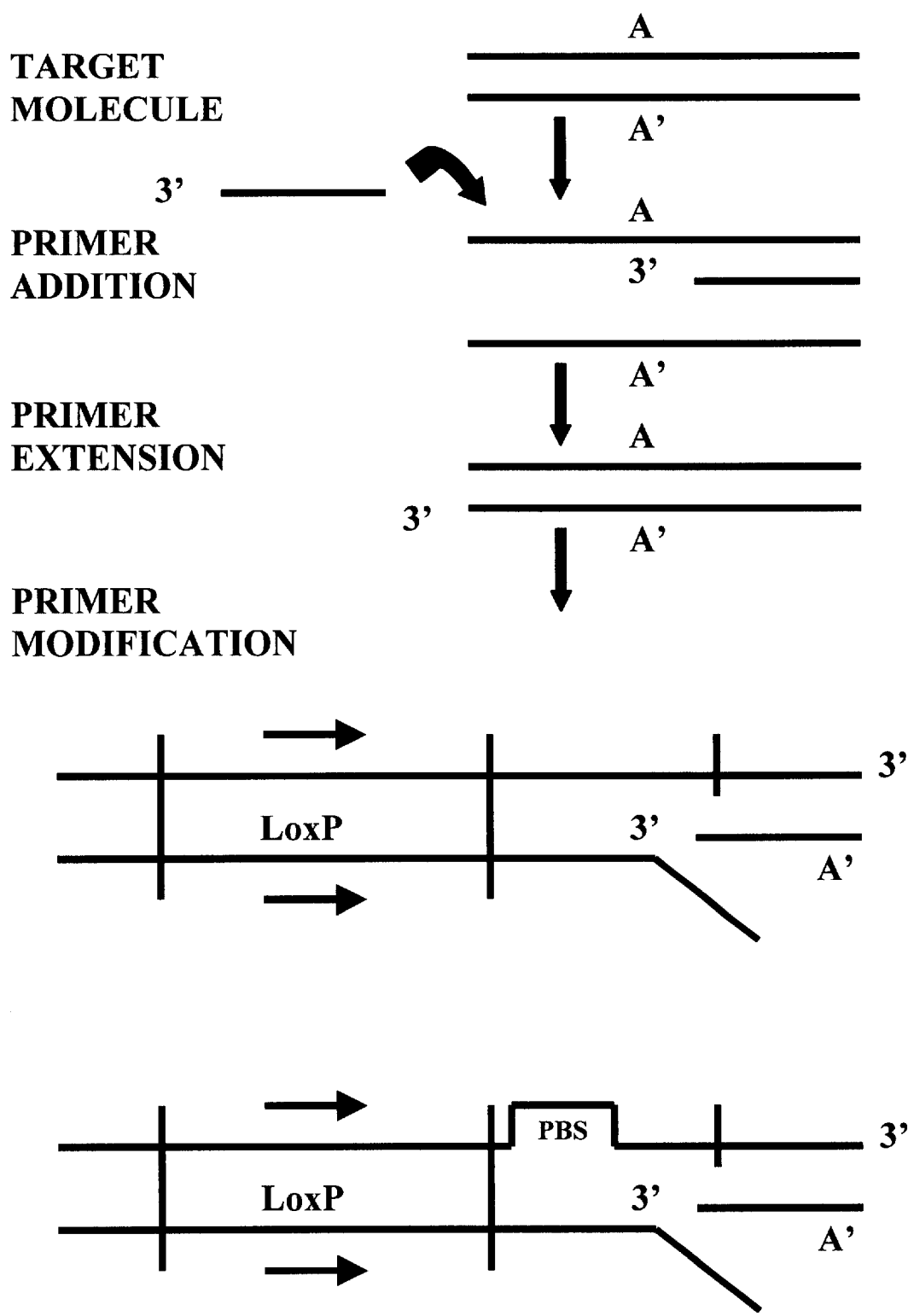
FIGS. 4A, 4B, 4C, and 4D show the formation of double-stranded circular molecules from linear molecules adapted using adaptor molecules that contain a recombinational site.
Figure 4B:
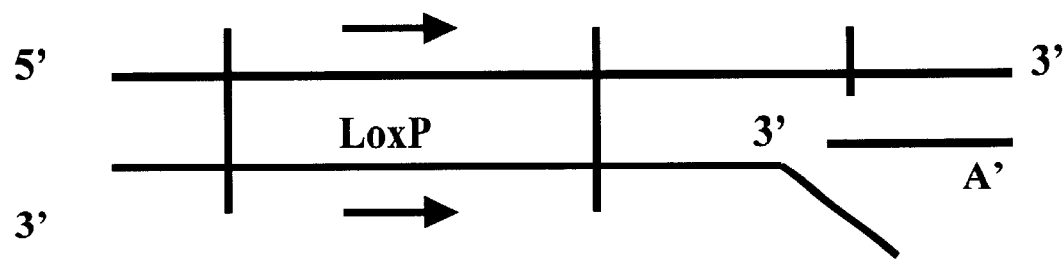
Figure 4B:
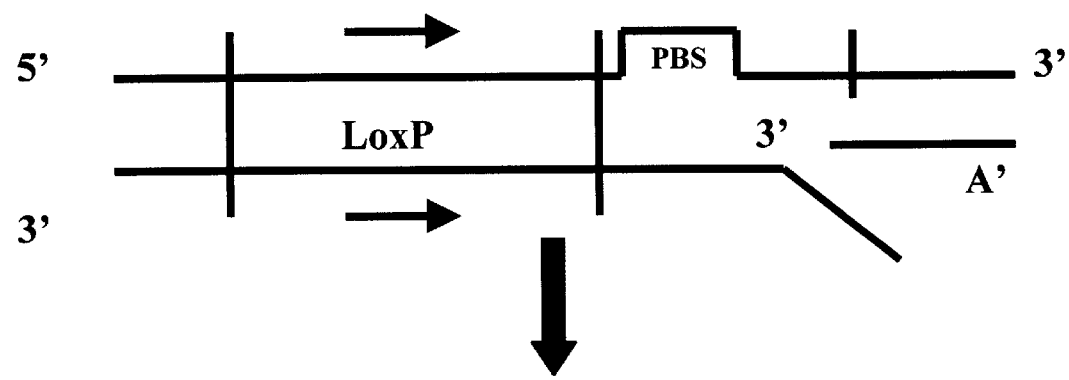
Figure 4B:
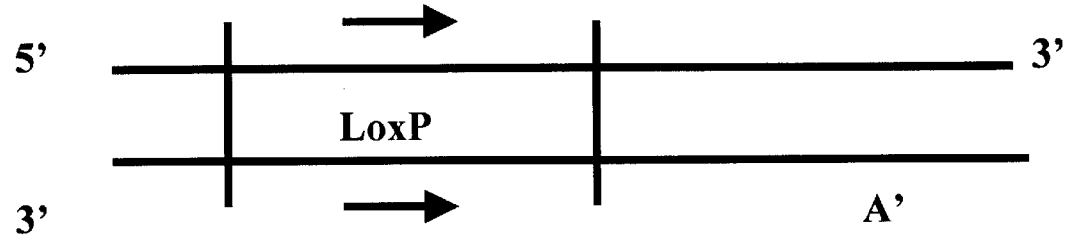
Figure 4B:
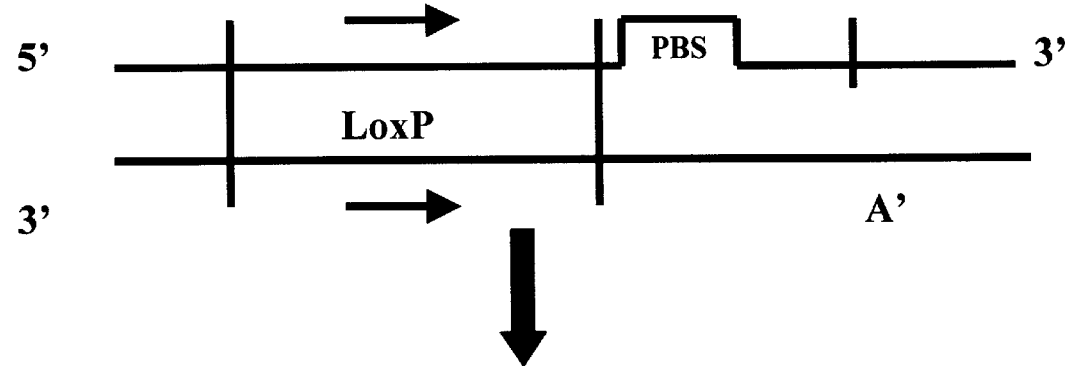
Figure 4C:
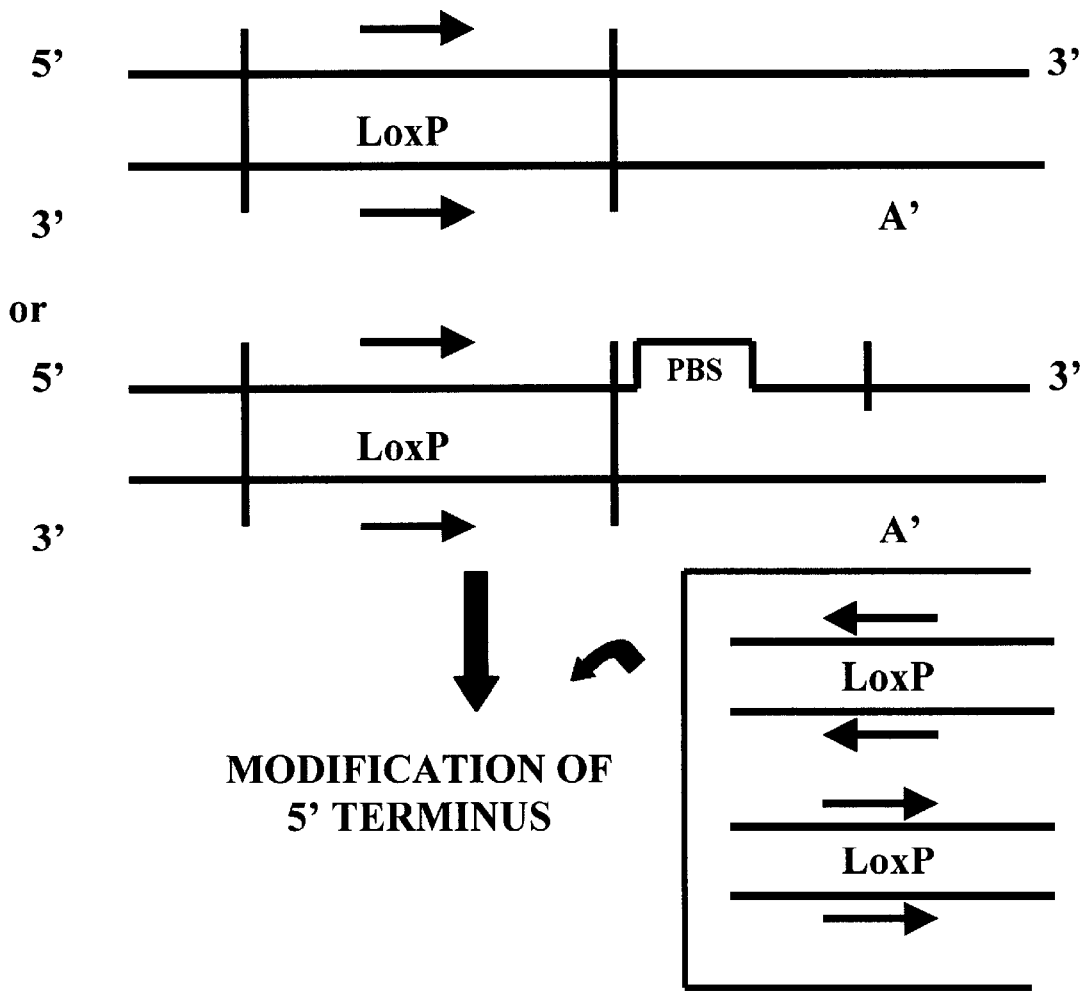
Figure 4C:
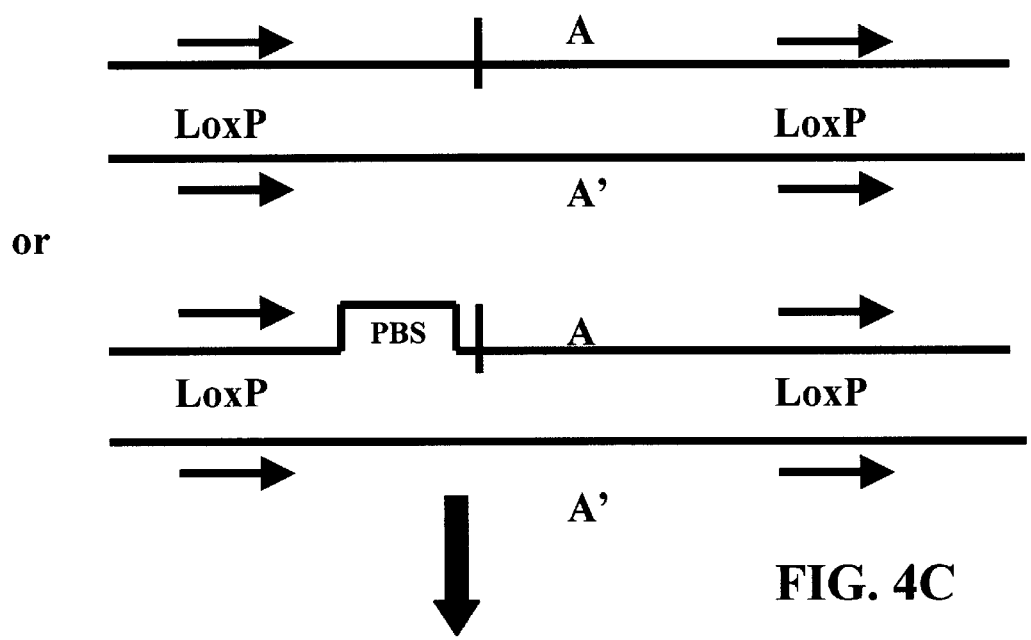
Figure 4D:
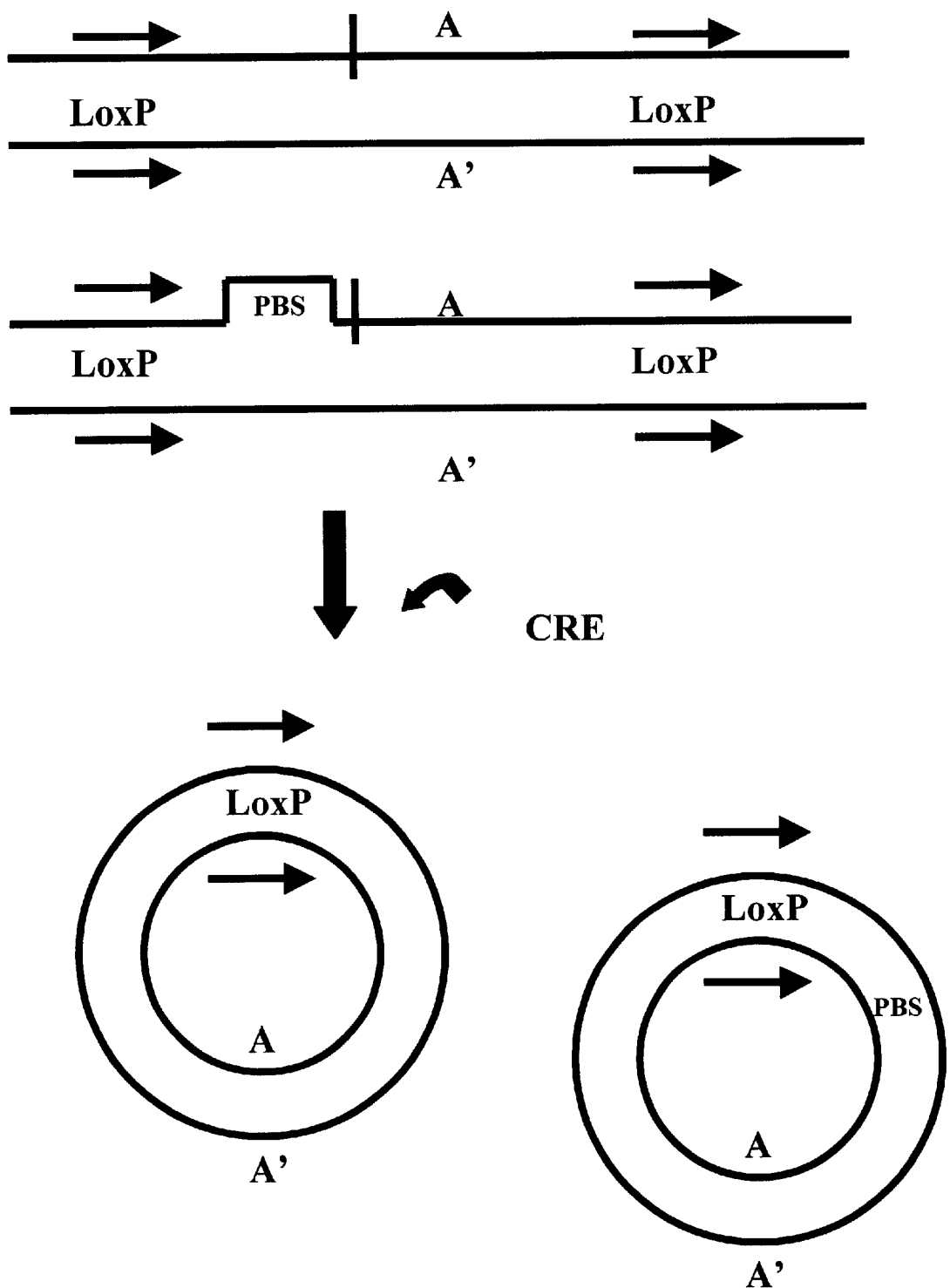

In a second subembodiment, to be used for example when the partially single-stranded/partially double-stranded 3' adaptor molecule(s) of the present invention is employed, the adaptation of the 3' terminus of the primer extension product is accomplished by the ligation of the primer extension molecule to the 3' adaptor molecule (FIG. 3B, line D). Because of the complementarity between the sequence of the protruding 3' terminus of the adaptor molecule and the 5' terminus of the primer extension molecule, the two molecules can hybridize to one another. Since the primer extension reaction has been controlled so that the average extension product terminates at a length corresponding to the end of the third region of the desired molecule, the average primer extension product will have a 5' terminus that can hybridize to the adaptor molecule.

In an alternative embodiment, of the invention, as for example when the concentration of the desired molecule is anticipated to be high, the molecules of the sample need not be denatured and can be directly cleaved into double-stranded molecules and then incubated with double-stranded or "hairpin"-shaped adaptors that contain recombinational sites and the other adaptor attributes described herein, so as to produce double-stranded molecules that contain the desired 3' and 5' adaptations.

When the adaptor molecule is DNA, any DNA ligase may be used to accomplish the ligation of the strands. Significantly, primer extension products that are longer or shorter than the precise length needed to permit the recessed 5' terminus of the adaptor to abut the 3' terminus of the primer extension are not amplified by the methods of the invention. They need not be removed from the reaction, and do not interfere with the subsequent desired amplification.

When the adaptor molecule is a DNA/RNA hybrid (in which the strand having the protruding 3' terminus is RNA), T4 ligase is employed to ligate the DNA strands together (Lehman, I. R., *Science* 186:790–797 (1974); Olivers, B. M. et al., *J. Molec. Biol.* 26:261 (1968); Kleppe, K. et al., *Proc. NatL. Acad. Sci.* (*U.S.A.*) 67:68 (1970); Fareed, G. C. et al., *J. Biol. Chem.* 246:925 (1971); Sgaramella, V. et al., *Proc. Natl. Acad. Sci.* (*U.S.A.*) 67:1468 (1970)).

The primer molecules will also have been modified to contain a recombinational site at their 5' terminus as discussed above. Such modification may be performed prior to or after the primer extension of the first or second steps of the method. If the modification is performed by ligation using a single-stranded molecule, the modification is performed prior to the third step of the process. If the modification is performed by ligation using a double-stranded molecule, the modification is performed after the 5' terminus of the primer extension product has been rendered double-stranded.

3. The Third Step of the Embodiment: Adaptation of the 5' Terminus of the Primer Extension Product Where the 5' terminus of the above-described primer was not initially modified to contain a DNA sequence that, when present in a double-stranded form comprises a recombinational site, such a sequence or site is added to the molecule produced after modification by the above-described 3' adaptor molecules.

a) The Methods wherein the 3' Adaptor Molecule Comprises a Recombinational Site

In the subembodiment wherein the 3' adaptor molecule comprises a recombinational site, it is important that the orientation of that site be the same as the orientation of the recombinational site that is to adapt, or has adapted, the 5' terminus of the primer or primer extension product.

In this embodiment of the methods of the invention, illustrated in FIGS. 4A, 4B, 4C and 4D, the single-stranded adaptor molecule (if that 3' terminus adaptor molecule was used), or the strand of the above-described partially single-stranded and partially double-stranded adaptor molecule that possesses the protruding 3' terminus (if that 3' terminus adaptor molecule was used) is not removed, and is extended by a DNA polymerase to form a double stranded linear DNA molecule having termini that comprise recombinational sites (in direct orientation, if loxP sites). Preferably, the use of a primer binding site in the adaptor molecule will create a "bubble" of single-stranded region located between the recombinational sites.

Action by a recombinase on the recombinational sites yields a double-stranded circular molecule. If the molecule contains the described primer binding site, then such site will provide a single-stranded region which may be used to initiate the replication of the circular molecule.

Figure 5:
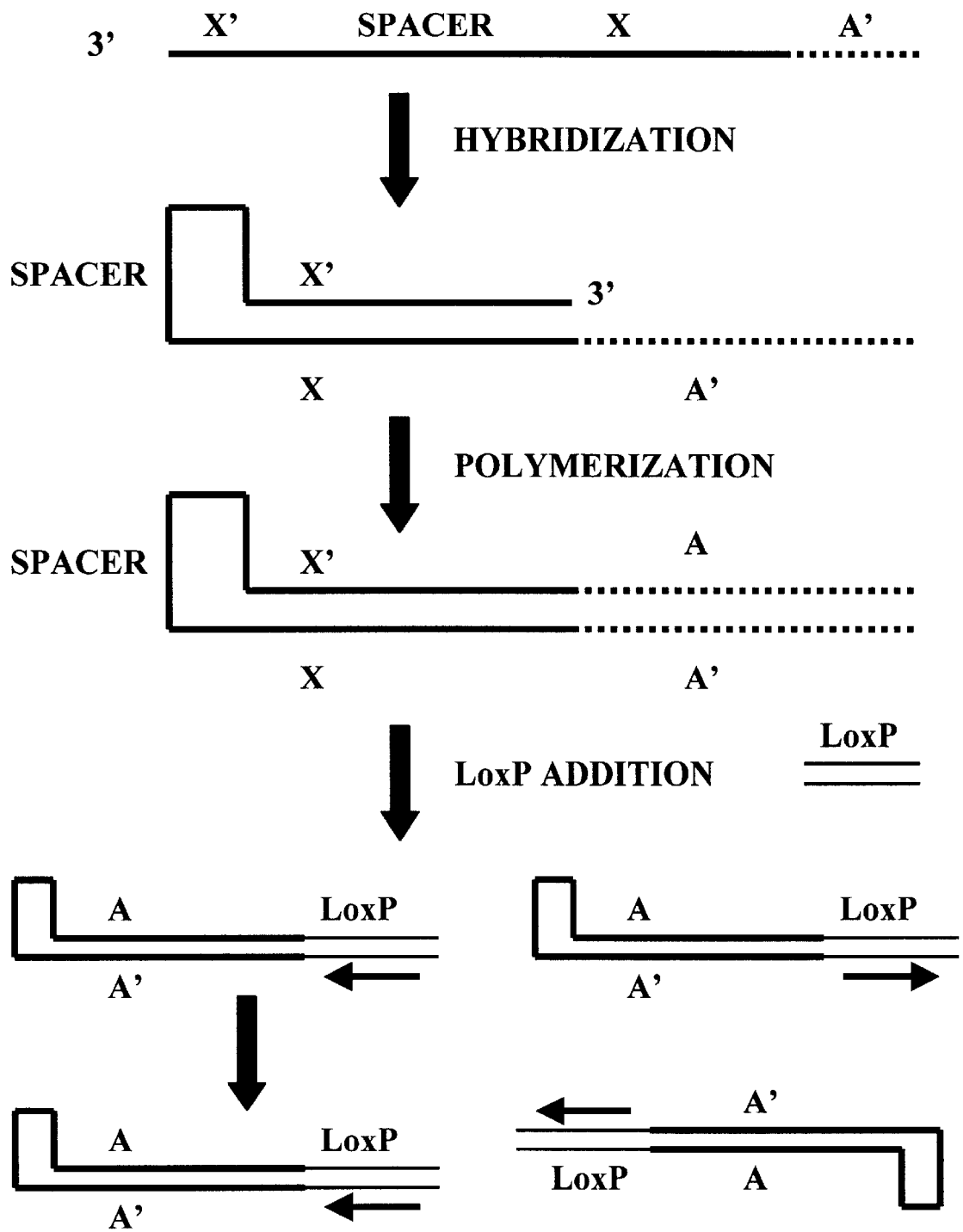
FIG. 5 shows the formation of hairpin loop molecules from the adaptation of the primer extension product with a 3' adaptor molecule having an inverted repeated sequence.

In one embodiment, such replication leads to a theta replicon. In a preferred embodiment, the double-stranded circle is "nicked" in one strand to permit a "rolling circle" replicon to form.

b) The Methods wherein the 3' Adaptor Molecule Comprises an Inverted Repeated Sequence In the subembodiment wherein the 3' adaptor molecule comprises an inverted repeated sequence (FIG. 5), the strand of the adaptor molecule that contained the "protruding 3' terminus" is separated from the primer extension strand. Any means known in the art may be used to accomplish such separation. Optionally, and preferably, the strand of the adaptor molecule that contained the "protruding 3' terminus" is removed from the sample. In a less preferred embodiment, the strand of the adaptor molecule that contained the "protruding 3' terminus" is labelled with biotin. In this subembodiment, the sample is heated to denature double-stranded molecules and treated with a biotin-binding agent (for example, streptavidin) to Hereby separate or remove the biotinylated molecule from the primer extension product.

In the most preferred subembodiment, the strand of the adaptor molecule that contained the "protruding 3' terminus" is RNA, and is separated or removed from primer extension product through the enzymatic activity of RNAse H, which preferentially degrades the RNA strand of an RNA/DNA hybrid.

The reaction conditions are then adjusted, if necessary, to permit DNA polymerization to occur. DNA polymerase is added, if needed, to the reaction, along with nucleotide triphosphates, etc., such that template-dependent extension of the 3' terminus of the adapted molecules can occur.

Since the adaptor molecule contains an inverted repeat, such polymerization results in the formation of a hairpin loop structure. In a preferred mode of the invention, the adaptation of the 5' terminus of the extension product is accomplished after such hairpin loop structures have formed, by providing double-stranded recombinational sites to the reaction, and permitting such sites to ligate to the terminus of the hairpin. This mode of adaptation is preferred, since the ligation of such molecules will occur in a randomized orientation, such that, on average one-half of the molecules will contain recombinational sites that are in one orientation, and one-half of the molecules will contain recombinational sites that are in the opposite orientation.

Figure 6:
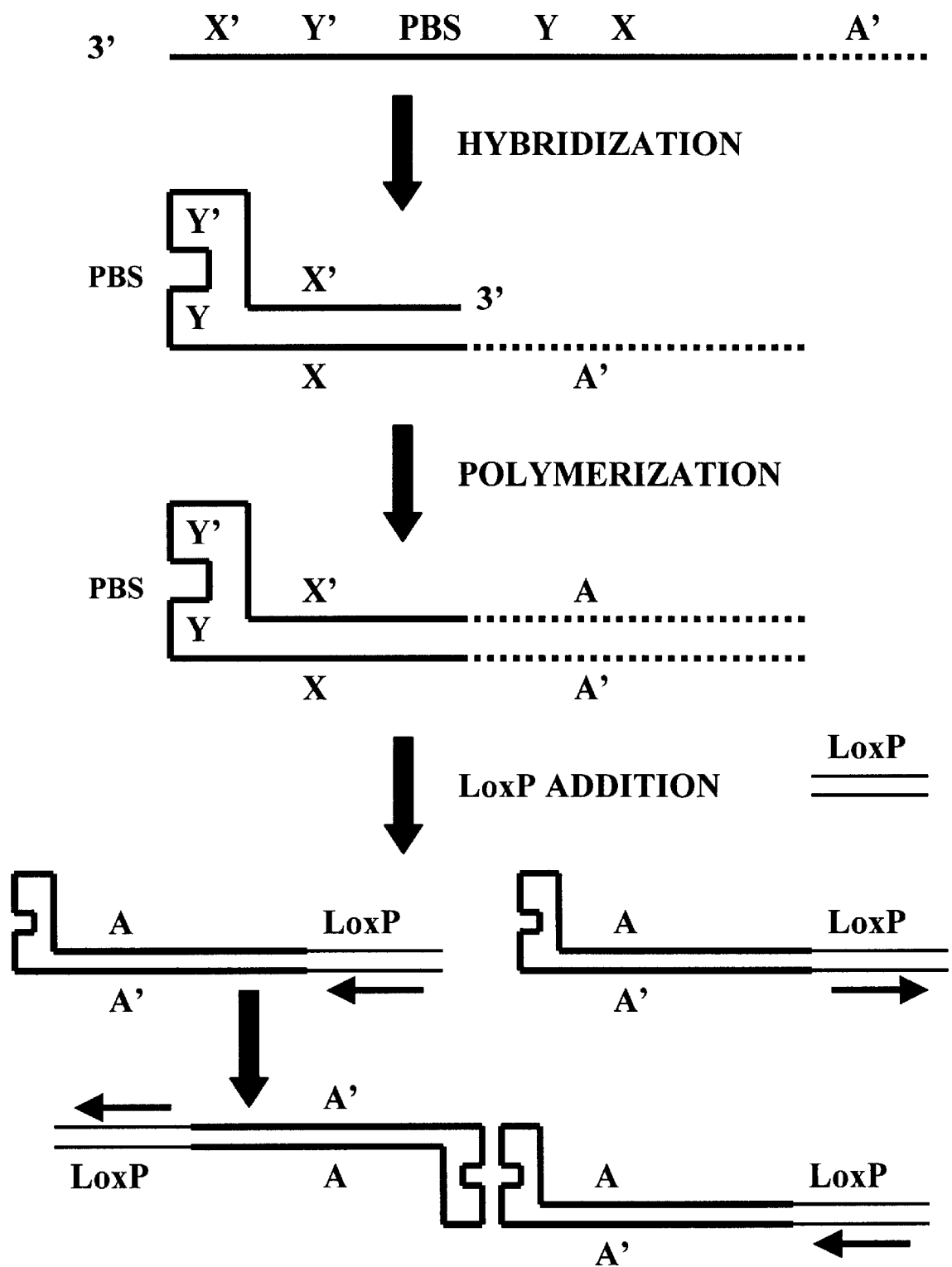
FIG. 6 shows the formation of "bow-tie" molecules from the adaptation of the primer extension product with a 3' adaptor molecule having a pair of nested inverted repeated sequences.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin origin "rolling circle" replicon manner as described below.

c) The Methods wherein the 3' Adaptor Molecule Comprises a Pair of Nested Inverted Repeated Sequences In the subembodiment wherein the 3' adaptor molecule comprises a pair of nested inverted repeated sequences (FIG. 6), the strand of the adaptor molecule that contained the "protruding 3' terminus" is separated from the primer extension strand, in the manner described above.

The reaction conditions are then adjusted, if necessary, to permit DNA hybridization to occur. The random hybridization of the primer extension products will also result in the formation of a double-stranded molecule having different external inverted repeated sequences (i.e. formed from different 3' adaptor molecules, having different external inverted repeated sequences such as are depicted as X/X' and Q/Q'). The strands of these molecules will anneal to one another due to hybridization between their respective internal inverted repeated sequences. Because the external inverted repeated sequences of the two strands are not complementary to one another, they will not hybridize to one another. Thus, the external repeated sequences of each strand will be able to participate in intra-strand hybridization.

After permitting such hybridization, DNA polymerase is added, if needed, to the reaction, along with nucleotide triphosphates, etc., such that template dependent extension of the 3' terminus of the adapted molecules can occur. The action of DNA polymerase on these molecules will lead to the formation of a "bow-tie" molecule characterized in possessing two hairpin loops that are annealed to one another by virtue of the hybridization between the internal inverted repeated sequences of the molecules.

The terminus of these molecules is then preferably adapted by providing double-stranded recombinational sites to the reaction, and permitting such sites to ligate to the terminus of the hairpin, in the manner described above. Approximately one-half of all bow-tie molecules will contain recombinational sites in direct repeat.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin-origin "rolling circle" manner as described below.

4. The Fourth Step of the Embodiment: Amplification

Because the above steps produce molecules that contain recombinational sites (e.g. loxP), the addition of a recombinase (preferably Cre) catalyzes a double-strand exchange at the recombinational sites of the molecules.

Figure 7:
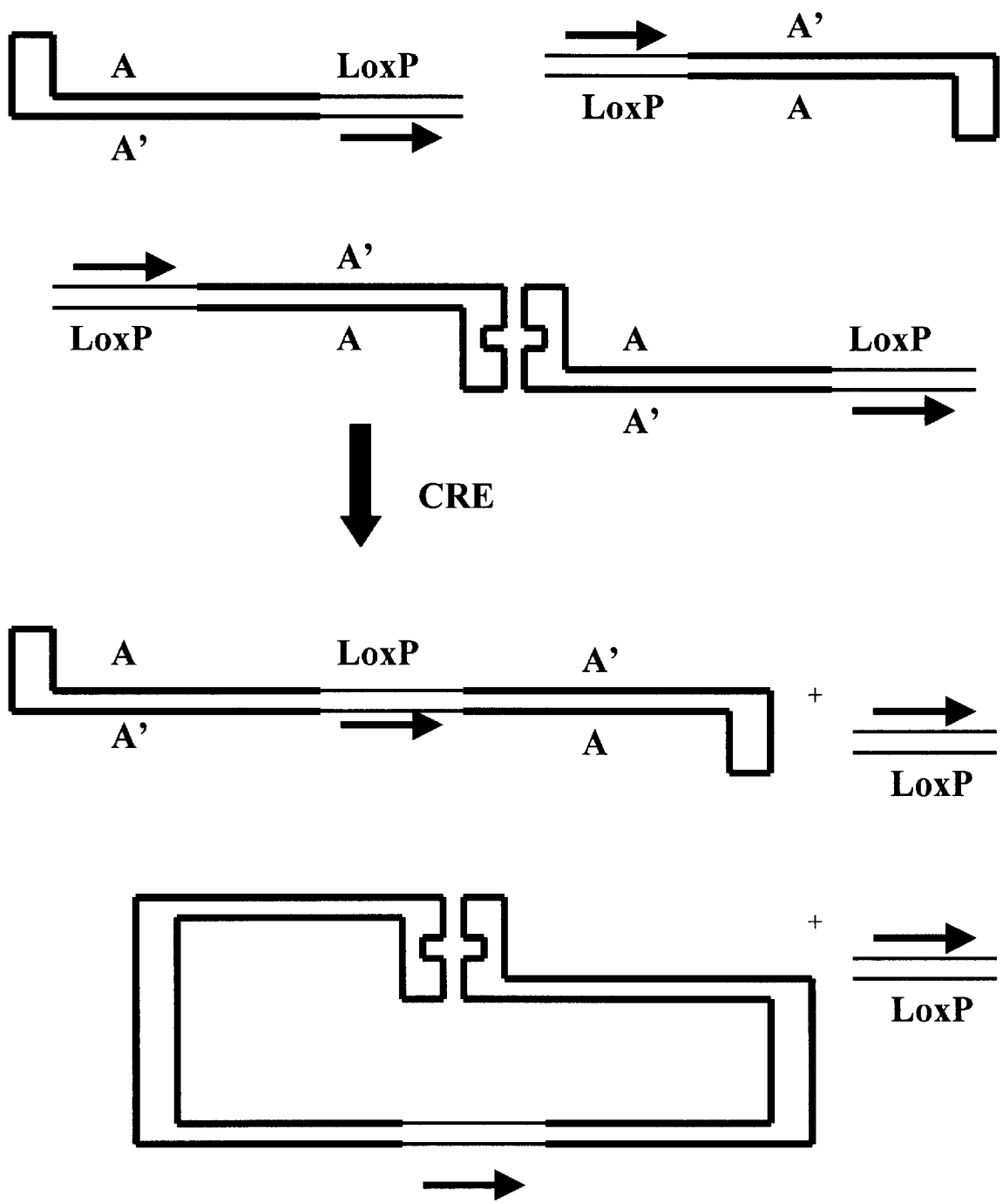
FIG. 7 shows the conversion of hairpin loop and "bow-tie" molecules having directly repeated recombinational sites into single strand circular molecules.

For a "bow-tie" molecule hidaving recombinational sites in the same directional orientation, the recombinational action of the recombinase converts the linear molecules into a single strand circular molecule (FIG. 7). Similarly, two hairpin loops having recombinational sites in the same directional orientation can be recombined to form a single strand circular molecule (FIG. 7). These circular molecules are characterized in having two copies of each strand of the desired sequence, four copies of the spacer region (which optionally comprises the described internal inverted repeated sequences), two copies of each of the two external inverted repeated sequences and a single recombinational site (FIG. 7).

Unless the initially employed primer sequences have been removed or destroyed, these sequences will displace the hybridized strands of the circular molecule. Such displacement may be facilitated by thermally denaturing the molecule, if desired. Such sequences may be used to amplify the desired sequence.

Alternatively, amplification may be accomplished by providing a primer that is complementary to the optional primer binding site. Since the circular molecule does not contain any sequence complementary to the primer binding site, such primer molecules can readily access the site and initiate amplification without thermal denaturation.

Figure 8A:
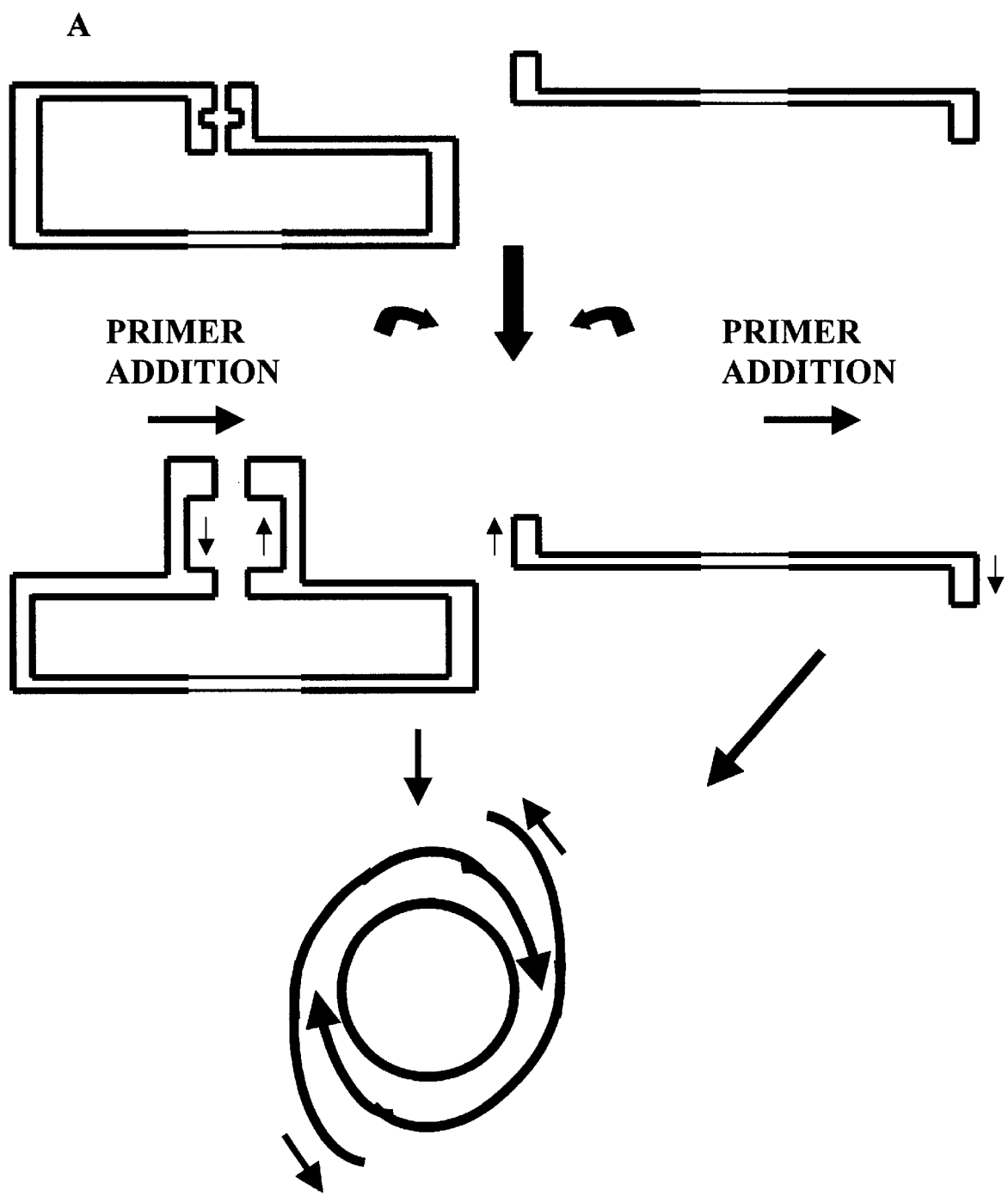
FIGS. 8A and 8B show the amplification replicons of the present invention.

For single-stranded circular molecules, since the primers can anneal at two sites on the molecule, primer extension yields a twin-origin "rolling circle" replicon (i.e. a rolling circle replicon having two extending strands, as shown in FIG. 8A).

Figure 8B:
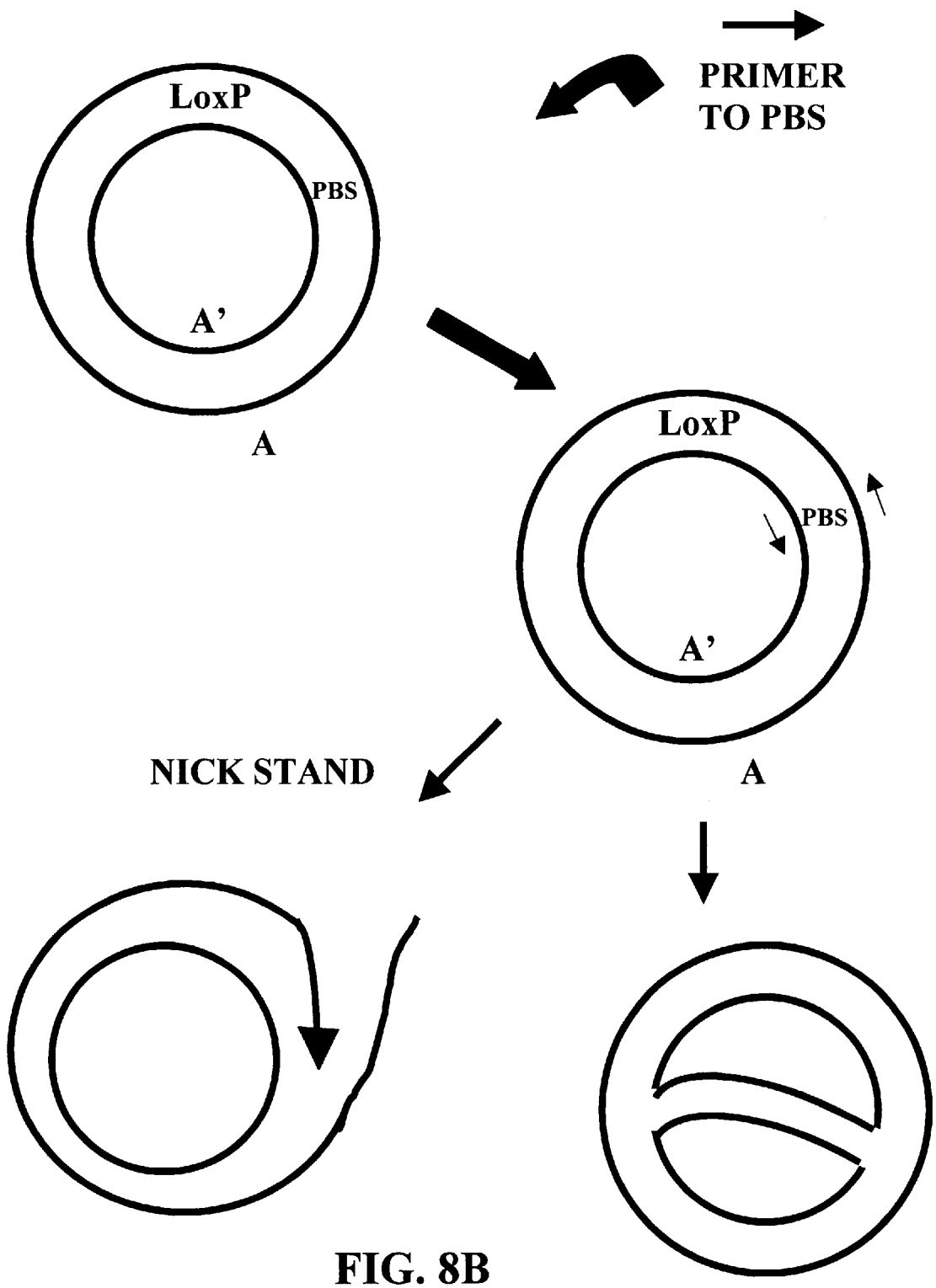

For the double-stranded circular molecules produced by the above method steps, amplification can be preferably obtained in either of two manners. In one embodiment, in which the addition of topoisomerase or gyrase is desirable, the double-stranded molecule is replicated to form a theta replicon (FIG. 8B). More preferably, one strand of the double-stranded molecule is nicked, such that primer extension results in the displacement of the nicked strand atid the formation of a "rolling circle" replicon. Such nicks can be produced by radiation, by chemical adducts (ethidium bromide, etc.), by an endonuclease, or by other means. A preferred method for forming such nicks is by incorporating at least one modified nucleotide (e.g., α5'-[a-thio] triphosphate (Pharmacia) or methylated nucleotide) into one strand of a restriction site (preferably present in the 3' adaptor molecule). Cleavage at that site by the relevant restriction endonuclease will create a single-strand nick (Walker, G. T. et al., *Proc. Natl. Acad. Sci. (U.S.A.)* 89:392–396 (1992)).

As each strand of any of the above replicons is extended, it provides additional template binding sites for additional primer extension. Thus, the kinetics of amplification are similar to, but faster than, viral b list kinetics.

The presence of inverted repeated sequences and recombinational sites permits additional hairpin loop structures to form. Since the reaction contains Cre, it will mediate recombination between such additional hairpin loop structures to form additional circular structures, thus increasing the number of amplification foci in the reaction.

All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as the replacement of reactants. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased many-fold.

B. Ligation Extension Method

In an alternate embodiment, the nucleic acid of the sample is cleaved (either enzymatically, or by physical means, such as shearing, sonication, etc.) into linear double-stranded polynucleotides. The ends of the polynucleotides are adapted (if necessary) so as to permit the polynucleotide to be inserted (most preferably via ligation) into a target restriction endonuclease cleavage site of either a precursor linear double-stranded molecule, or into a precursor circular molecule. In a preferred embodiment of such methods, the ligase will not be thermally stable, or will be otherwise labile, such that after the initial ligation reaction the ligase can be substantially inactivated.

1. Forming the Desired Circular Molecule a) Precursor Linear Molecule Method In this sub-embodiment of the present methods, the target polynucleotide is introduced (via ligation, preferably at a restriction site) into the above-described linear precursor molecule. Such introduction forms a double-stranded DNA molecule that comprises: (a) a first lox site located at a first end of the linear molecule, (b) a second lox site located at a second end of the linear molecule, wherein the first and the second lox sites are directly oriented with respect to one another so as to permit the Cre to mediate the circularization of the linear double-stranded molecules, and to thereby form the double-stranded circular molecule; (c) the target polynucleotide region located internal to the first and second lox sites; and (d) a hemi-modified restriction site located between the target polynucleotide region and one of the lox sites, wherein one strand of the hemi-modified restriction site of each of the linear molecules contains modified nucleotides (especially methylated nucleotides and (α-thio) phosphorothioate nucleotides), such that a restriction endonuclease that recognizes such restriction site will be incapable of cleaving that strand containing the modified nucleotides.

In accordance with the present invention, such a molecule is then incubated in the presence of Cre under conditions sufficient to permit circularization of the molecule such that a circular molecule b. Precursor Circular Molecule Method This subembodiment is similar to the above-described precursor linear molecule method, except that the step of the initial circularization is rendered unnecessary because the molecules are initially circularized.

Thus, in this sub-embodiment, the target polynucleotide is introduced (via ligation) into the target restriction site of the above-described circular precursor molecule. The resulting circular molecule comprises: (a) a lox site; (b) the target polynucleotide; and (c) a hemi-modified restriction site located between the target restriction endonuclease cleavage site and the lox site.

2. Amplification of the Circular Molecule

This circular molecule is then incubated in the presence of a restriction endonuclease that recognizes the hemi-modified site and causes a single-strand nick or gap having a 3' hydroxyl terminus to be created.

A polymerase and nucleotides are added to the reaction (if not already present). Under such conditions, the polymerase will mediate the extension of the created 3' terminus, and the consequent strand displacement of the 5' terminus of the cut strand. The nucleotides employed will preferably be unmodified, such that primer extension will recreate the hemi-modified restriction site, which is then cut, generating a new extendible 3' terminus. The net effect of such primer extension, strand displacement and nicking reactions is the displacement of a linear single-stranded molecule having a lox site at (or near) its 5' terminus and a region complimentary to the single primer at its 3' terminus.

The single primer is added (if not already present in the reaction). The presence of the single primer (and the polymerase and unmodified nucleotides) permits the linear molecule and the single primer to act as templates for one another to recreate the initially formed double-stranded DNA molecule.

Significantly, the above reactions use a single primer to mediate the amplification of a specific target polynucleotide even if that molecule were initially present in a complex mixture of undesired polynucleotides.

C. Isolation or Purification of the Amplified Molecules

This invention may be combined with many other processes in the arts of molecular biology to achieve a specific end. Of particular interest is purifying the target sequence from the other sequences in the nucleic acid sample. This can be accomplished most advantageously by annealing the nucleic acid sample to an oligonucleotide that is complementary to the target and is immobilized on a solid support. A convenient support would be a micro-bead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation: Particularly advantageous in some situations is the capture of RNAn amplification products by a DNA oligonucleotide complementary to an RNA sequence determined by the target sequence, the oligonucleotide being bound to a solid support such as a magnetic micro-bead. Preferably, this oligonucleotide's sequence does not overlap with that of any oligonucleotide used to purify the target before the amplification. RNA:DNA hybrids thus formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Since the molecules that are being amplified comprise both strands of the desired sequence, the use of restriction endonucleases can cleave the reaction products into discrete and defined fragments. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

D. Production of Recombinant Cells and Non-Human Transgenic Animals

As stated above, the methods of the present invention provide a means for obtaining a double-stranded linear DNA molecule comprising a lox site at each end, in direct repeat orientation, and a mammalian gene, or a polynucleotide fragment or cDNA transcript thereof between such lox sites. Such DNA molecules can be used as the substrate for the insertion of DNA into non-bacterial cells by, for example, the method of Sauer, B. L., U.S. Pat. No. 4,959,317 (herein incorporated by reference). Hence, the present invention may be employed in concert with the methods of Sauer, B. L., U.S. Pat. No. 4,959,317, to facilitate the production, and to produce recombinant non-bacterial cells, recombinant mammalian cells, and transgenic animals. The use of the Sauer, B. L. method (U.S. Pat. No. 4,959,317) to produce such cells and animals is well known (see, e.g., Xaio, Y. et al., *Nucl. Acids Res.* 25:2985–2991 (1997); Bethke, B. et al., *Nucl. Acids Res.* 25:2828–2834 (1997); Tarutani, M. et al., *Proc. Natl. Acad. Sci.* (*U.S.A*) 94:7400–7405 (1997); Agah, R. et al., *J. Clin. Invest.* 100:169–179 (1997); Jiang, R. et al., *Curr. Biol.* 7:R321–323 (1997); Akagi, K. et al., *Nucl. Acids Res.* 25:1766–1773 (1997), all herein incorporated by reference).

In particular, the methods or the present invention, in concert with such known methods of generating recombinant cells and non-human transgenic animals (such as transgenic rodents) thus permits a non-bacterial cell (e.g., a yeast cell, a mammalian cell (especially a mammalian embryonic stem cell) to be produced by introducing a double-stranded linear DNA molecule comprising a lox site at each end, in direct repeat orientation, and a mammalian gene, or a polynucleotide fragment or cDNA transcript thereof between such lox sites, into a chromosome of such cell, wherein the DNA molecule either contains a hemi-modified restriction site, or was derived from a DNA molecule that contained such a hemi-modified restriction site (as cloning such DNA molecule into a plasmid and permitting in vivo amplification to occur in the absence of modified nucleotides; by employing such DNA molecules in PCR or other in vitro amplification to occur in the absence of modified nucleotides; etc.).

The present invention includes articles of manufacture, such as "kits." In one embodiment, such kits will, typically, be specially adapted to contain in close compartmentalization a first container which contains a nucleic acid molecule comprising a recombinational site at its 5' terminus and a region complementary to the desired polynucleotide at its 3' terminus, and a second container which contains a nucleic acid molecule comprising a recombinational site at its 5' terminus and a region having a sequence complementary to the 5' terminus of the desired polynucleotide at its 3' terminus, and, optionally, a third containing a recombinase suitable for catalyzing the recombination of the sequence of the first container which. The kit may also, optionally, contain one or more DNA and/or RNA polymerases, ligase, buffers, etc. in amounts sufficient to permit the amplification of a desired nucleic acid molecule. The kit may additionally contain instructional brochures, and the like.

E. Gene Detection and the Detection of Gene Expression

The methods and reagents of the present invention may be used to accomplish the detection of genes, gene expression, chromosomal elements (such as telomeres, centromeres, etc.) and polymorphisms, and to facilitate the identification of pathogens and tissue.

In one embodiment, a sample containing DNA (such as a fixed cell or tissue biopsy) is treated with the reagents of the present invention under conditions sufficient to permit either linear or exponential amplification of target sequences that are unique to a particular pathogen or to a particular tissue. The detection of amplification thus establishes the presence of the pathogen in the sample, or the identity and or location of the particular tissue in the sample. For example, a sample of tissue may be treated in situ (or in solution) with oligonucleotide primer reagents of the present invention whose sequences have been selected to amplify DNA sequences unique to chlamydia. The detection of amplification thus establishes the presence of the pathogen. In a further embodiment, the sample of tissue may be treated in situ (or in solution) with oligonucleotide primer reagents of the present invention whoses sequences have been selected to amplify an antibiotic resistance determinant possibly possessed by a pathogen (for example, chlamydia). Such reagents can be used to determine the susceptibility of the pathogen to particular antibiotics. In a sub-embodiment thereof, oligonucleotide primer reagents of the present invention and the processes of the present invention may be performed to assess the presence of mRNA rather than genomic DNA. For such purposes, initial denaturation of the sample DNA is unnecessary, for either the first or second primer molecules will be designed to hybridize to the single-stranded mRNA of transcribed genes selected such that they will together mediate amplification only if the, for example, gene encoding the antibiotic resistance determinant is being expressed.

In an alternative embodiment, the primer molecules can be used to assess, and reveal, the presence of cells of a particular tissue in a sample or biopsy. For example, by selecting primer molecules that possess a sequence capable of amplifying insulin-encoding mRNA, the present invention can be used to detect pancreatic cells that express insulin. In like manner, the primers of the present invention can be designed to amplify sequences of any expressed mRNA, and thereby provide a sensitive means of histological evaluation. Likewise, by addressing such primers to amplify mRNA encoding fetal antigens or tissue-specific proteins, the present invention can be used to detect and locate metastasized tumor cells, and to assess the state of differentiation of tumor cells.

In a further embodiment, the primer molecules of the present invention may be designed such that their sequences will amplify DNA only if the DNA in question contains a particular nucleotide residue at a polymorphic site. In this matter, the reagents and methods of the present invention can be used for polymorphic analysis. For example, either of the primers the present invention can be designed such that their 3' terminus corresponds to a polymorphic site, such that the 3' terminus will hybridize to a target DNA sequence only if that sequence possesses a complementary polymorphic nucleotide. In a sub-embodiment of this embodiment, the primers of the present invention will be designed such that their 3' termini will each correspond to the same polymorphic site (such that the primers for aligned for hybridization, their 3' termini would overlap by a single nucleotide corresponding to the polymorphic site).

Detection of genes and gene expression may be accomplished by any of a variety of means, for example by labeling the amplified product, by hybridization assays (including in situ hybridization), etc.

F. Quantitative Amplification

The reagents and methods of the present invention may be adapted to permit the quantitative amplification of DNA and RNA molecules. In the simplest embodiment, such quantitative amplification can be obtained by conducting the isothermal amplification in the presence of limiting, and preferably exhausted, amounts of Amplification Primer, such that amplification will be substantially linear and non exponential.

In an alternative embodiment, the unique catalysis mediated by site-specific recombinases may be exploited to achieve quantitative amplification. When a site-specific recombinase, such as Cre, is employed to mediate recombination between two recombinational sites (such as two Lox sites) of a linear DNA molecule, the reaction leads to the formation of a circular molecule and to the formation of a Lox oligonucleotide. By performing the amplification in the presence of access Cre, the rate of formation of the Lox oligonucleotide becomes proportional to the concentration of target DNA present in the sample. Accordingly, one may measure the concentration of the target DNA initially present in the sample by determining the concentration of lox oligonucleotide present and the specific activity of the Cre enzyme employed.

G. DNA and Protein Detection

The reagents and methods of the present invention may also be used to facilitate the detection of DNA, or protein or other antigens that may be present in a sample. In one embodiment, this may advantageously be accomplished by exploiting the fact that certain site-specific recombinases, such as Cre, become covalently bound to DNA as a consequence of the recombinational reaction. Accordingly, amplified DNA can be bound and detected using anti-Cre antibodies. This feature of the invention permits DNA amplification to be discerned through an immunoassay format (such as ELISA or radioimmuno assay).

In an alternative embodiment, chimeric antibodies capable of bonding to Cre and to a protein or antigen of interest may be constructed. In the presence of Cre, such antibodies will cause Cre to become bound to the antibody, and will form a reagent that is capable of binding to a protein or antigen of interest, if present in a sample, and mediating site-specific amplification of target DNA in the presence of suitable primers. In one sub-embodiment, the employed primers will be designed with overlapping sequences such that they are capable of hybridizing to one another even the absence of exogenous template. In such a sub-embodiment, the presence of the protein of interest in the sample can thus be detected by DNA amplification mediated by Cre and the employed primers. In an alternative sub-embodiment, the employed primers will not possess overlapping sequences, and additional complementary target template molecule will be provided to the reaction.

Having now generally described the invention, the same will be more readily understood through reference to the following examples, which are provided by way of illustration, and are not intended to be limiting of the present invention, unless specified.

EXAMPLE 1

Isothermal Amplification Method I

Figure 9:
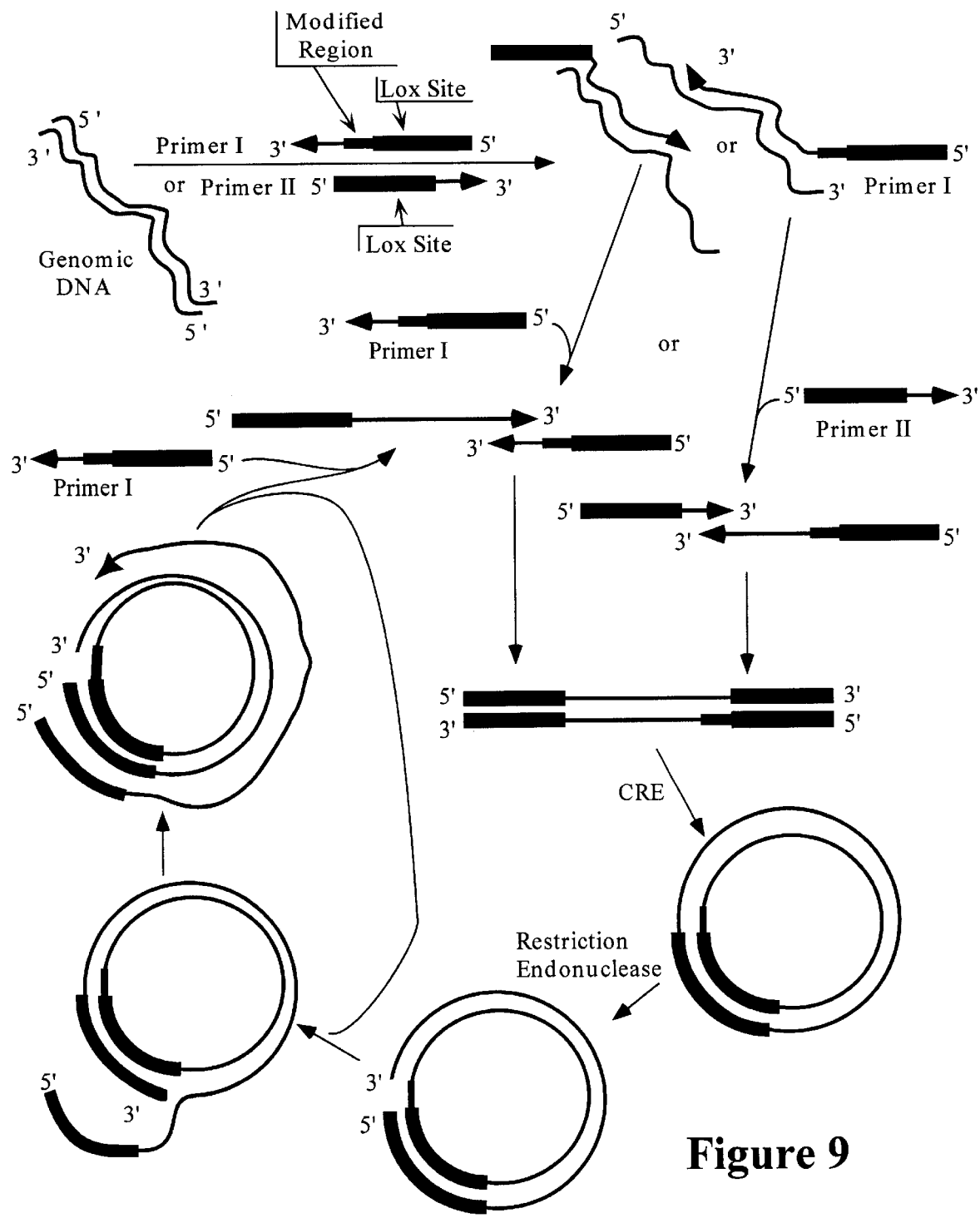
FIG. 9 provides a diagramatic representation of an illustrative isothermal amplification reaction described in Example 1.

FIG. 9 provides a diagrammatic representation of a first preferred method for achieving the amplification of a desired region of genomic DNA.

With reference to FIG. 9, a sample of double-stranded genomic DNA is denatured, as by heat, etc., and incubated in the presence of either an Amplification Primer molecule whose 3' terminus is complementary to a target polynucleotide region whose amplification is desired, or a Target Primer whose 3' terminus contains a target polynucleotide region (or, equivalently, a region complementary to the complement of a target polynucleotide region whose amplification is desired).

Most preferably, the Target Primer is added as the initial primer (i.e., prior to the addition of Amplification Primer). The purpose of this primer is to create an initial template for further amplification that is mediated by the Amplification Primer. Thus, the Target Primer may be provided at lower concentration than the Amplification Primer, which should be present in significant excess. By providing the Target Primer before addition of the Amplification Primer, undesired effects caused by primer-primer hybridization can be avoided.

In the preferred embodiment shown in FIG. 9, the Target Primer comprises two polynucleotide regions: (1) a "target" polynucleotide region present at the 5' end of the polynucleotide that is to be amplified, and (2) a "proto-lox" polynucleotide region. The "proto-lox" region is located 5' to the "target" region of the primer.

In the preferred embodiment shown in FIG. 9, the Amplification Primer comprises three polynucleotide regions: (1) a "target complement" polynucleotide region (i.e., a polynucleotide complementary to a polynucleotide present at the 3' end of the target polynucleotide that is to be amplified), (2) a polynucleotide region containing modified nucleotides and (3) a "proto-lox" polynucleotide region (i.e., a polynucleotide, which, if hybridized to a complementary polynucleotide would form a double-stranded molecule that would comprise a lox site. The polynucleotide region containing modified nucleotides is located 3' to the "proto-lox" region. The sequence of the polynucleotide region containing modified nucleotides is selected such that if it were hybridized to a complementary polynucleotide, the resulting double-stranded polynucleotide would comprise one or more restriction endonuclease recognition site(s). The sequence of the polynucleotide region containing modified nucleotides of the primer is preferably further selected such that this restriction endonuclease recognition site is recognized by a restriction endonuclease that is capable of cleaving DNA that lacks such modified nucleotides, but is substantially or completely incapable of cleaving a polynucleotide containing such modified nucleotides. Examples of modified nucleotides include ribonucleotides (where the polynucleotides are DNA), phosphorothioate nucleotides, methylated nucleotides, bromodeoxyuridine, deoxyuridine, etc. Examples of suitable restriction endonucleases and their recognition sequences are described in Sambrook, J., et al. (In: *Molecular Cloning, A Laboratory Manual,* Second Edition, Cold Spring Harbor Laboratories, Cold Spring Harbor, N.Y. (1989)), in Walker, G. T. et al. (*Proc. Natl. Acad. Sci.* (*U.S.A.*) 89:392–396 (1992)), and in the GibcoBRL/Life Technologies 1993–1994 Catalog and Reference Guide, all of which references are herein incorporated by reference.

The primer (either Amplification Primer or Target Primer) is incubated with the denatured DNA of the sample under conditions which permit both hybridization and template dependent primer extension. to occur. Thus, a polymerase and (non-modified) nucleotides are provided to the reaction. The primer extension reaction is terminated by adjusting the reaction conditions to cause the denaturation of the extended primer from its template molecule.

As will be appreciated, if the target molecule was present in the initial sample, the Ad extension product of the Amplification Primer molecule will contain a region that is complementary to the target molecule, and thus complementary to the 3' terminus of the Target Primer (see FIG. 9). As such, it and can hybridize to the Target Primer. If the Target Primer was employed in the initial primer extension reaction, then the resulting extension product will comprise a region that is complementary to the 3' terminus of the Amplification Primer (see FIG. 9). and can hybridize to the Amplification Primer. A second primer extension reaction is conducted using whichever primer (amplification or Target Primer) was not used in the initial primer extension reaction.

Thus, the reaction conditions are adjusted to permit hybridization and primer extension to occur. As a consequence of the presence of polymerase and nucleotides, the annealed amplification and Target Primers produce blunt-ended linear molecules in which the desired "target" region is flanked by lox sites. Significantly, the "proto-lox" polynucleotides of the amplification and Target Primers are oriented (with respect to the target complement and target polynucleotide regions) such that the flanking lox sites are in a direct repeated orientation.

Cre recombinase is added to the reaction. As will be appreciated, Cre may be added at an earlier step in the process if desired. The presence of Cre catalyzes the circularization of the lox sites of the blunt-ended linear molecules produced above. As a result, a double-stranded circular molecule is formed. The double-stranded molecule contains the target polynucleotide, a single lox site, and a restriction endonuclease site in which one strand (i.e., the strand derived from the Amplification Primer) contains modified nucleotides and the other strand (i.e., that derived from the extension of the Target Primer via DNA polymerase) does not contain modified nucleotides.

A restriction endonuclease that recognizes the restriction endonuclease recognition site of the double-stranded circular molecule is added to the reaction. As discussed above, the restriction endonuclease and the recognition site are selected such that the endonuclease does not cleave DNA containing modified nucleotides. Thus, the introduction of the endonuclease "nicks" (if a single site is present) or "gaps" (if more than one site are present) the non-modified strand of the circular molecule.

Such "nicking" or "gapping" creates a 3' terminus which may be extended by the previously added polymerase. Such extension displaces the 5' terminus of the non-modified strand. As the polymerase extends the 3' terminus through the region containing the restriction site, a new hemi-modified site is created. This new site is "nicked" or "gapped" by the previously added restriction endonuclease, and thus generates yet another 3' terminus that may be extended by the polymerase (see, FIG. 9). Since the cleavage that creates this subsequent 3' terminus occurs behind the initially created 3' terminus, it does not affect the ability of a polymerase to extend the initially created 3' terminus. In a like manner, the reactions continue without further intervention: generating a new 3' terminus, extending that terminus, creating a new hemi-modified restriction site, "nicking" or "gapping that site to create yet another 3' terminus.

As each primer extension product is extended, it displaces the prior strand that was hybridized to its template. This strand displacement reaction continues without fturther intervention, and generates a set of identical linear molecules, all of which contain a "proto-lox" site and the target polynucleotide region.

At this point in the protocol, a linear isothermal amplification of the target polynucleotide has been accomplished. Since the Amplification Primer (discussed above) has not been removed from the reaction, it will hybridize with the linear amplification product, and thereby provide a substrate for a new primer extension reaction. The consequence of this reaction is the generation of a new double-stranded blunt-ended linear molecule in which a double-stranded target region is flanked by lox sites (see, FIG. 9). This new blunt-ended molecule is identical to that described above.

Since the reaction still contains Cre recombinase, the linear molecule is converted into the above-described double-stranded circular molecule. Significantly, the newly formed circular molecule contains the same hemi-modified restriction endonuclease recognition site as the initially formed circular molecules. Thus, cleavage of that site results in a "nick" or "gap," which creates a further amplification nucleus.

In sum, an exponential isothermal reaction results. This reaction produces double-stranded polynucleotides having the sequence of the desired target molecule.

Significantly, if the Amplification Primer were provided in limiting amounts, were made of RNA and degraded (as with RNase A, etc.) after the reaction had been initiated, or if it contained other nuclease sensitive bases, or was at least partially biotinylated, it would be possible to exhaust, degrade or remove the Amplification Primer from the reaction after the reaction had initiated. Upon such exhaustion, degradation or removal, the reaction will shift from an exponential amplification reaction that amplifies both strands of the target to a linear reaction that amplifies only the target polynucleotide strand. Such a modification is desirable in instances in which the purification and recovery of only a single strand is desired (e.g., in DNA sequencing, and in probe generation).

Figure 10:
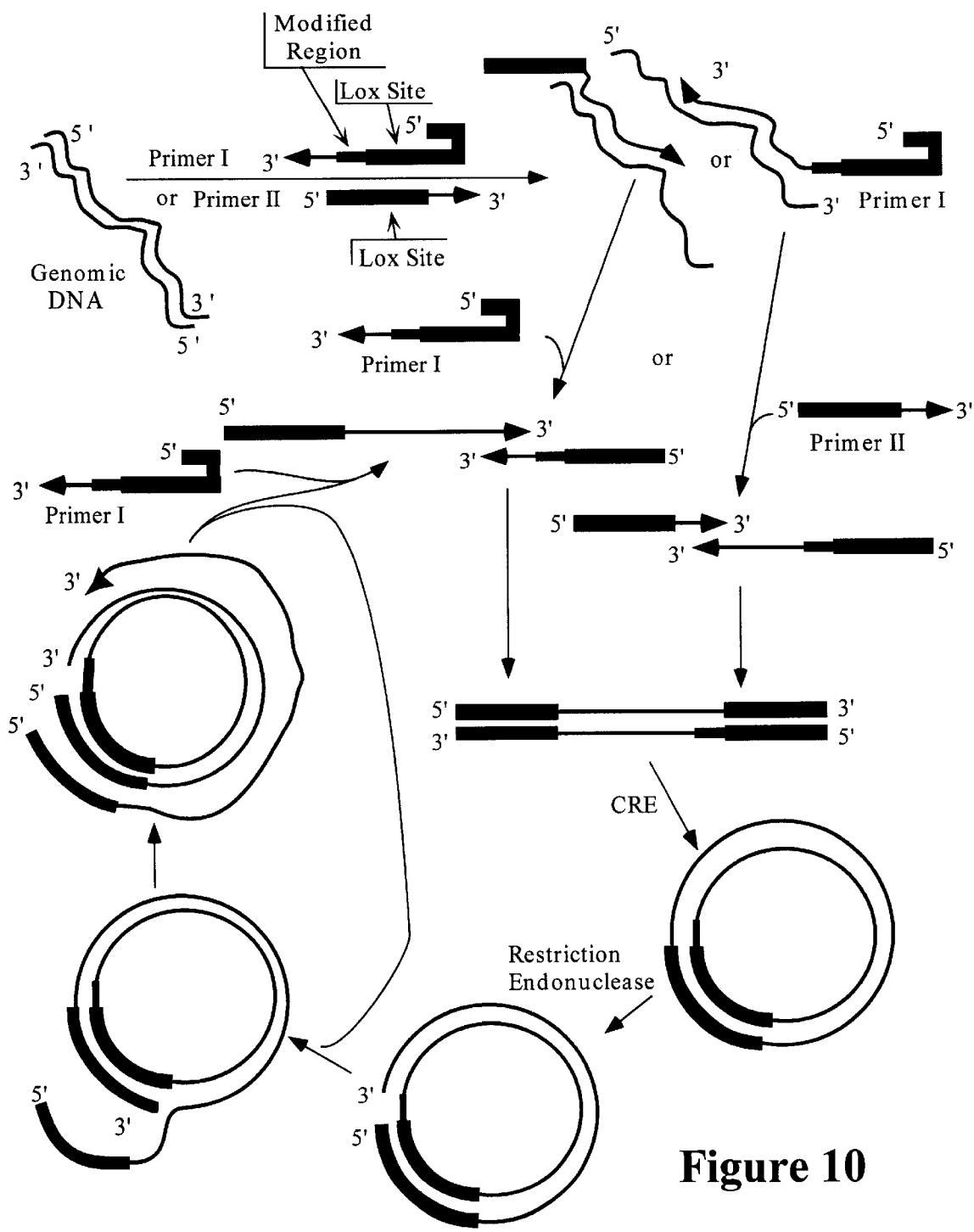
FIG. 10 provides a diagramatic representation of an alternative illustrative isothermal amplification reaction described in Example 1. The Figure illustrates the use of a 5' fourth region of Primer I that is complementary to a portion of the proto-Lox site.

FIG. 10 provides an alternative embodiment of the above-described method. In this alternative embodiment, either or both of the amplification and Target Primers is modified to contain a sequence that causes the 5' terminus of the primer(s) to partially self-hybridize to the primer, such that the 3' terminus of the primer is single-stranded. Such self-hybridization acts to minimize or prevent any hybridization between the Amplification Primer and the Target Primer molecules.

EXAMPLE 2

Isothermal Amplification Method II

FIGS. 11 and 12 provide diagrammatic representations of alternate preferred methods for achieving the amplification of a desired region of genomic DNA.

With reference to FIG. 11, an amplification "cassette" is employed. The cassette comprises a linear double-stranded polynucleotide having directly oriented lox sites at its two termini. The lox sites are separated from one another by a double-stranded region that comprises a hemi-modified restriction site, and a target restriction site region that contains one or more restriction sites suitable for receiving the target DNA fragment(s). Most preferably, the target restriction site region will have multiple restriction cleavage sites, such that, by treating the cassette with multiple restriction endonucleases two fragments are produced, one of which contains a lox site and a first partial restriction site, and the other of which contains a second, and preferably different partial partial restriction site, the hemi-modified restriction site, and a lox site. The use of a cassette whose target restriction site region contains two restriction sites having different sequences, and yielding incompatible termini upon cleavage is preferred, since such prevents the religation of the cassette. Incompatible termini are termini that cannot be ligated to one another. Compatible termini are termini that are ligatable.

Genomic or other target DNA is cleaved using a restriction fragment that produces termini that are compatible with the termini generated from the restriction cleavage of the cassette. The target fragments and the cassette fragments are incubated together in the presence of ligase under conditions sufficient to form a ligation product in which the target fragment has been inserted into the target restriction site region (replacing any DNA present between the original restriction sites).

The resulting molecule is a double-stranded linear molecule having lox sites at its ends. The molecule is preferably purified away from the restriction enzymes and ligase used above. Alternatively, such enzymes can be inactivated by heat, antibodies, or other means.

As shown in FIG. 11, Cre, present or now added to the reaction, catalyzes the circularization of the target fragment-bearing cassette. Since the circular molecule bears a hemi-modified restriction site, it comprises a substrate for a restriction enzyme that recognizes this site. As in Example 1, such a restriction endonuclease will cleave only the unmodified strand, and will produce a nick in one strand of the double-stranded circular molecule. The 3' termini genertated from such cleavage is extended by polymerase, in the presence of all four nucleotide species. Such extension regenerates the restriction site, and leads to the production of a linear single-stranded molecule containing the entire length of one circular strand.

An Amplification Primer is added to the reaction (it may be provided earlier, if desired). The Amplification Primer is identical to that described in Example 1. As such, the Amplification Primer contains a region complementary to the 3' terminus of the linear single-stranded molecule produced above. The amplification moleule hybridizes with the linear single-stranded molecule, and, because polymerase and nucleotides are present, mediates the formation of a double-stranded molecule whose structure is essentially identical to that of the target fragment-bearing cassette (differing only in having a partial restriction site at one terminus). The molecule has two directly oriented lox sites, and is thus circularized by Cre to yield a molecule that is identical to the double-standed circular molecule discussed above. This molecule is processed in the manner described above, leading to exponential amplification FIG. 12 shows a related embodiment, differing only in employing a precircularized "cassette" molecule.

EXAMPLE 3

Attributes of the Isothermal Amplification Methods I and II

Several aspects of the embodiments discussed in Examples 1 and 2 are noteworthy. FIGS. 9–12 show the circularization of a single "full-length" linear molecule into a "unit length" circle. However, the same lox orientations responsible for circularization of nucleic acid molecules can mediate multiple head to tail joining of full-length linear molecules so as to form a "multi-unit length" circle. Significantly, since the lox site is asymmetric, such head to tail joining conserves the both the orientation of lox sites, and the orientation of strands. Thus, when multiple full-length linear double-stranded molecules are joined together, all of the target strand sequences of the individual full-length linear molecules are present on the same strand of the "multi-unit length" circle; similarly, all of the target complement strand sequences of the individual full-length linear molecules are present on the other strand of the "multi-unit length" circle. Hence, because the modified nucleotides of the respective hemi-modified restriction site will all be present on the same strand of the resulting double-strand "multi-unit length" circle. As a consequence, only one strand of the multi-unit circle would be cleaved by the restriction enzyme, and the other would remain intact. Thus, such a circle will be processed in the same manner as a unit length circle, but will result in the production of multiple copies of the target (or target complement) strand each time the entire circle is replicated. The same unit length amplification product will be produced regardless of the number of full-length linear molecules that have recombined to form a circle.

This attribute of the present invention is of particular significance since it permits one to amplify target molecules that would otherwise be too small (i.e., too thermodynamically rigid) to circularize readily into unit length circles. Thus, the processes of the invention, without any additional intervention or attention, mediate the head to tail joining of target molecules until a multimer is formed that possesses sufficient thermodynamic flexibility to be capable of circularizing into a circle. If the target molecule is large, the resulting circle can be of unit length; if the target molecule is small, a multi-unit length circle can be formed.

In embodiments, such as that described in Example 2, in which no Target Primer is employed, amplification is single-primer mediated. As a consequence, if the method were employed in the absence of Amplification Primer (or if the supply of Amplification Primer became exhausted), the method would mediate a general, linear amplification of one strand of all of the DNA in a sample. Such reaction conditions are useful in applications, such as those encountered in forensic analysis, in which the supply of target material is limited and finite. The method provides a means for amplifying all molecules present, thus increasing target material supply.

In such single primer embodiments, the Amplification Primer controls both the sequence specificity of the reaction, and the extent of exponential amplification. Thus, whereas the reactions of this Example 2 mediate a linear amplification of all target DNA present in the sample, reactions conducted in the presence of Amplification Primer mediate an exponential amplification of those molecules of the sample containing sequences complementary to the sequence of the target region of the Amplification Primer.

In any of the methods of Example 1 or 2, multiple Amplification Primers may be employed in lieu of the single Amplification Primer described. The use of multiple Amplification Primers permits one to selectively amplify subpopulations of molecules having desired characteristics. However, this use is particularly valuable with the single primer amplification methods of this Example 2. For example, if such methods are conducted with an Amplification Primer that contains a sequence complementary to a promoter sequence, an exponential amplification of all molecules having such a promoter sequence will occur. If a second Amplification Primer is employed that contains a sequence complementary to a repressor binding site, an exponential amplification of all molecules having both a repressor binding site and a promoter will occur.

Likewise, in any of the embodiments, such as those of Example 1, in which two primers are employed, the primers may be used to amplify polynucleotides having desired attributes without prior knowledge of their sequences. Thus, for example, by employing an Amplification Primer that is complementary to a promoter or centromere sequence, and a Target Primer that is complementary to a telomere sequence, the methods of the present invention permit amplification of nucleic acid molecules that possess both the promoter (or centromere) sequence and the telomere sequence.

EXAMPLE 4

Isothermal Amplification Method III

Figure 13:
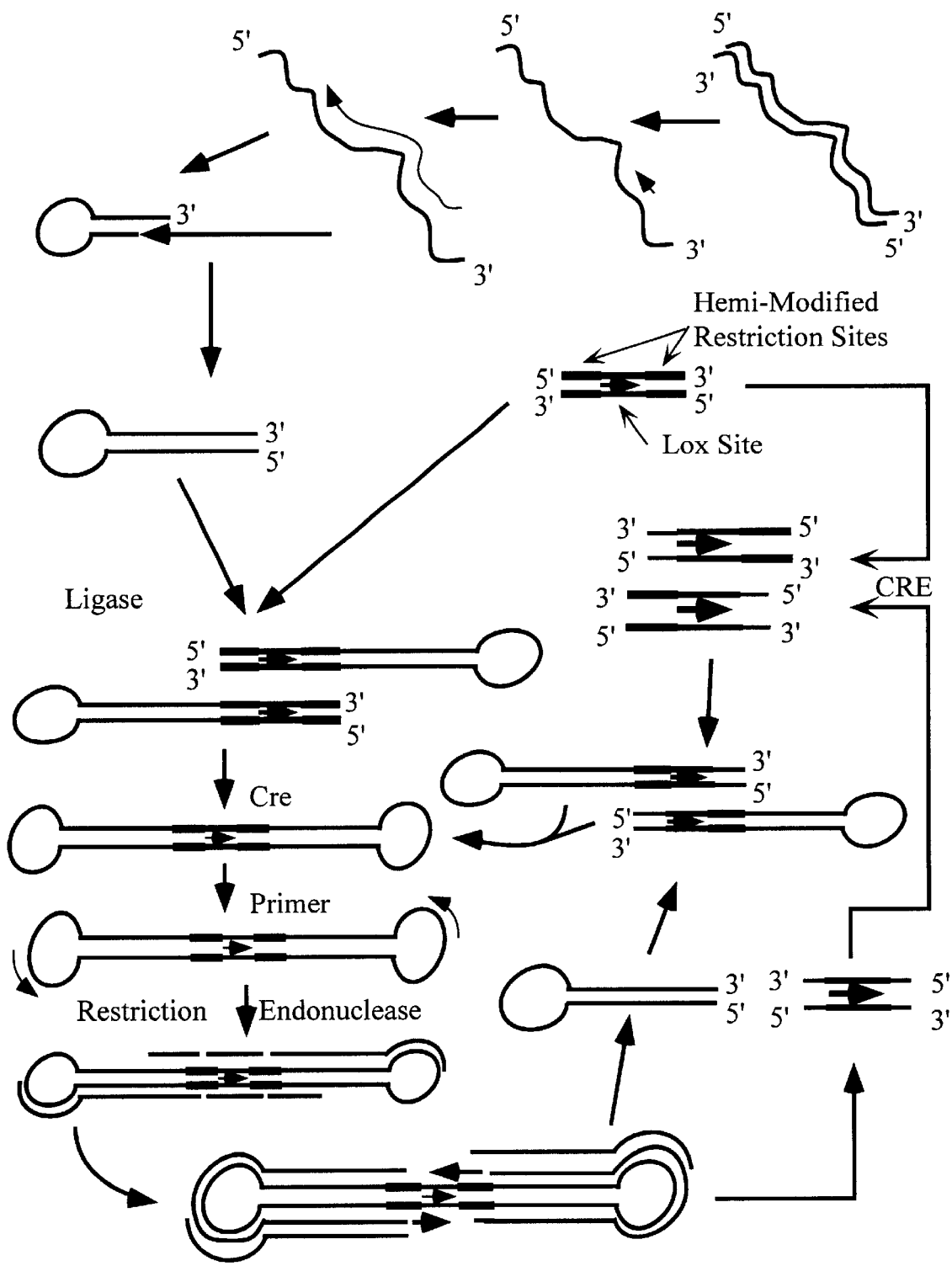
FIG. 13 provides a diagramatic representation of the alternative illustrative isothermal amplification reaction described in Example 4 in which an unmodified primer is used and a DNA ligase is employed.

FIG. 13 provides a diagrammatic representation of a second preferred method for achieving the amplification of a desired region of genomic DNA.

With reference to FIG. 13, a sample of double-stranded genomic DNA is denatured, as by heat, etc., and incubated in the presence of an Amplification Primer molecule whose 3' terminus is complementary to a target polynucleotide region whose amplification is desired.

In the preferred embodiment shown in FIG. 13, the Amplification Primer need not be modified in any respect. It merely needs to be of sufficient length to permit stable hybridization.

The primer is incubated with the denatured DNA of the sample under conditions which permit both hybridization and template dependent primer extension to occur. Thus, a polymerase and (non-modified) nucleotides are provided to the reaction. The primer extension reaction is terminated by modifying the reaction conditions to cause the denaturation of the extended primer from its template molecule.

A Target Primer is added to the reaction. Although, in a preferred embodiment, this Target Primer is introduced after the termination of the primer extension reaction, such Target Primer may be introduced at any time before, during or after the introduction of the modified Amplification Primer discussed above. The Target Primer comprises a partially single-stranded-partially double-stranded "loop" structure. It contains a protruding 3' terminus whose sequence is the same as a sequence present at the 5' end of the polynucleotide that is to be amplified, such that the protruding 3' terminus is complementary to the 3' terminus of the extension product of the Amplification Primer.

The reaction conditions are adjusted to permit both the ligation of the primer extension product of the Amplification Primer to the recessed 5' terminus of the Target Primer, and the template dependent extension of the protruding 3' terminus of the Target Primer. Thus ligase, polymerase and nucleotides are provided. The resulting product comprises a double-stranded, blunt-ended, target molecule having the 5' terminus of one strand connected to the 3' terminus of the other via the "loop" structure of the Target Primer (see, FIG. 13).

A linker molecule is introduced into the reaction. The linker molecule is a blunt-ended, double-stranded linear molecule which comprises a lox site flanked by one or more pairs of restriction endonuclease recognition sites. Preferably, as shown in FIG. 13, the restriction sites are composed of modified nucleotides. Both strands of the restriction site are modified.

The previously added ligase catalyzes the ligation of the linker molecule to the free 3'/5' terminus of the previously formed product (FIG. 13) to form a "looped target molecule." Such ligation can occur in either of two possible orientations (owing to the directionality of the lox site). The orientation of ligation is unimportant to the reaction.

Two products of such ligation in which the lox site has been ligated in opposite orientations can be recombined via the addition of Cre to form an end-looped structure having two copies of the double-stranded target polynucleotide separated by a single lox site.

A third primer is introduced which is preferably complementary to a polynucleotide region of the non-base paired "loop" part of the molecule. The previously added polymerase, causes the 3' terminus of this third primer to be extended around the "loop" and into the polynucleotide region of the target, displacing the hybridized non-template strand. The third primer is optional, and added to facilitate the initiation of the amplification reaction. Its presence is not needed during amplification.

Extension of the primer past the modified restriction site, creates a hemi-modified restriction site. The introduction into the reaction of a restriction endonuclease that recognizes this site, causes a "nick" or "gap" in the non-modified strand. As in Example 1, once started, these reactions continue without fuirther intervention. Thus, primer extension creates a hemi-modified site, that site is cleaved by a restriction endonuclease thereby creating a new 3' terminus which is extended to form a new hemi-modified site, thereby restarting the cycle.

Again, as in Example 1, the cleavage that creates a new 3' terminus occurs behind a previously created 3' terminus, and thus does not affect the ability of a polymerase to extend the initially created 3' terminus. As shown in FIG. 10, the product of such primer extension and cleavage reactions is the same "looped target molecule" as that described above.

Since the reaction still contains ligase and the linker molecules, such molecules will be ligated together, and the products of such ligation can then circularize via the action of the previously added Cre recombinase. Such circularization generates new amplification foci.

In sum, the method achieves the exponential amplification of both strands of the target polynucleotide without using modified primers.

The isothermal nature of the amplification processes described above permits each product of each reaction to procede through the entire set of reactions at its own pace. This capacity, which reflects the isothermal nature of the reactions, is in marked contrast to cyclic reactions such as the polymerase chain reaction, in which all reactants are required to procede in unison to the next step of the reaction. By avoiding such a requirement, the isothermal amplification methods of the present invention provide faster reaction kinetics.

EXAMPLE 5

Isothermal Amplification of a 4 kb DNA Molecule

The ability of the methods of the present invention to mediate DNA amplification is illustrated with respect to a 4 kb fragment of pBR322. The fragment is introduced into a cassette comprising a LOX site and a hemi-methylated restriction site, and is amplified in vitro.

Construction of the pBR322-LOX derivative: Method I pBR322 is a double-stranded DNA plasmid 4,362 nucleotides long Maniatis, T. et al., In: "Molecular Cloning A Laboratory Manual," Cold Spring Harbor Press, Cold Spring Harbor, N.Y. (1982)). It has a single EcoRI site located at nucleotide 4360, and a single BainHI site located at nucleotide 375. Accordingly, pBR322 DNA that is restricted with both EcoRI and BamHI yields two fragments whose lengths are 377 and 3,985 nucleotides (the 3,985 nucleotide fragment is referred to as the 4 kb fragment). Because cleavage at the EcoRI site leaves a protruding 5' AATT end, and cleavage at the BamHI site leaves a protruding 5' GATC end, a pBR322 fragment restricted with both EcoRI and BamHI cannot be ligated together. The LOX-pBR322 derivative is made as follows:

1. Isolation of a pBR322 EcoRI-BamHI fragment

To isolate the desired pBR322 EcoRI-BamHI fragment, pBR322 is obtained (Life Technologies, Gaithersburg, Md.) and cleaved with both EcoRI and BamHI (Life Technologies, Gaithersburg, Md.) according to the manufacturer's instructions. Linear molecules having a length of approximately 4,000 nucleotides are purified by agarose gel electrophoresis (Sambrook, J. et al., In "Molecular Cloning A Laboratory Manual," Cold Spring Harbor Press, Cold Spring Harbor, N.Y. (1989)).

2. Construction of an EcoRI-NotI-LOX-BamHI Fragment

A double-stranded EcoRI-Noti-LOX-BamHI DNA linker molecule is produced having the sequences SEQ ID NO:1:

5' aattcgcggc cgcataactt cgtataatgt atgctatacg aagttatg 3' and SEQ ID NO:2:

5' gatccataac ttcgtatagc atacattata cgaagttatg cggccgcg 3'

These oligonucleotides hybridize to one another as shown below:

The underlined nucleotides in SEQ ID NO:2 are 5-methylcytosine (however, phosphorothioated residues may be used). The double-stranded DNA linker molecule can be obtained in any of a variety of ways. In one embodiment, it may be formed by mixing equimolar amounts of synthetic oligonucleotides having the sequences SEQ ID NO:1 and SEQ ID NO:2.

Alternatively, and more preferably, the double-stranded EcoRI-NotI-LOX-BaniHI DNA linker molecule can be made by incubating an oligonucleotide primer having the sequence of SEQ ID NO:3:

5'aattcgcggc age 3' with a synthetic oligonucleotide having the sequence of SEQ ID NO:2 in the presence of DNA polymerase, dATP, TTP, dCTP and dGTP. As indicated above, the underlining below the nucleotides indicates that the residues are 5-methylcytosine residues. The appropriate termini are obtained from the resulting blunt-ended double-stranded DNA molecule by treating it with EcoRI and BamHI.

3. Construction of the pBR322-LOX derivative

The desired pBR322-LOX Derivative is constructed by incubating the previously isolated 4 kb EcoRi-BamHI pBR322 fragment in the presence of the EcoRI-NotI-LOX-BamHI DNA linker molecule, and DNA ligase. After permitting the ligation reaction to occur, the ligated material is purified by gel electrophoresis, and material migrating at the position of relaxed double-stranded circular DNA is recovered. This material is the desired pBR322-LOX derivative.

Construction of the pBR322-LOX Derivative: Method II

The desired pBR322-LOX derivative is alternatively made as follows: pBR322 is obtained (Life Technologies, Gaithersburg, Md.) and cleaved with both EcoRI and BamHI (Life Technologies, Gaitbersburg, Md.) according to the manufacturer's instructions. Linear molecules having a length of approximately 4,000 nucleotides are thereby obtained (Sambrook, J. et al., In "Molecular Cloning A Laboratory Manual," Cold Spring Harbor Press, Cold Spring Harbor, N.Y. (1989)).

The restricted DNA is then subjected to a PCR amplification using two PCR primers comprising the sequences, SEQ ID NO:4 and SEQ ID NO:5.

SEQ ID NO:4:

5' tatacgaagt tatggatcca taacttcgta tagcatacat tatacgaagt tatgcggccg cgaattcttg aagacgaaag 3'

As will be recognized, the first PCR primer (SEQ ID NO:4) contains a 13 base long span of nucleotides (nucleotides 1–13) that is connected to a BamHI recognition sequence (14–19). Nucleotides 20–53 are a LOX site. The initial span of nucleotides is complementary to the initial 13 nucleotides of the LOX site, such that a "loop" can form between these regions of the primer. Nucleotides 54–61 are a NotI site. Nucleotides 62–80 comprise the sequence of the EcrRI site of plasmid pBR322 and nucleotides 4359–4347 of pBR322. The underscoring of C residues in the NotI site

```
SEQ ID NO:1
    EcoRI    NotI                                                          LOX SITE
                                                                             BamHI
5'  aattc gcggccgc ataacttcgtataatgtatgctatacgaagtt at g         3'

3'       g cgccggcg tattgaagcatattacatacgatatgcttcaa ta cctag    5'
SEQ ID NO:2
``` indicates that at least one of the residues is methylated or phosphorothioated.

SEQ ID NO:5:
5' tatacgaagt tatgaattca taacttcgta taatgtatgc tatacgaagt tatggatcct ctacgccgga 3'

As will be recognized, nucleotides 1–13 of the second PCR primer (SEQ ID NO:5) are complementary to the first 13 nucleotides of the LOX site that is present at nucleotides 20–53. Nucleotides 14–19 are an EcoRI site. Nucleotides 54–70 are the BamHI site of pBR322, and the eleven nucleotides of pBR322 that follow that site.

The PCR amplification thus yields linear double-stranded molecules having LOX sites on each terminus. The molecule is circularized using Cre.

The Amplification Primer

The Amplification Primer is most preferably obtained by nucleotide synthesis. The primer is single-stranded, and has 80 nucleotides comprising the sequence, SEQ ID NO:4:

5' tatacgaagt tatggatcca taacttcgta tagcatacat tatacgaagt tatgcggccg cgaattcttg aagacgaaag 3'

As a control, a Target Primer may be synthesized having 70 nucleotides, and comprising the sequence, SEQ ID NO:5:

5' tatcagaagt tatgaattca taacttcgta taatgtatgc tatacgaagt tatggatcct ctacgccgga 3'

The Amplification Primer and the Target Primer are oriented with respect to one another so as to comprise primers that may be used in PCR for amplifying the 4 kb pBR322 EcoRI BaniHI derivative.

Cre, NotI and Polymerase

Cre is obtained from Novogen, Inc. (Madison, Wis.). Alternatively, it may be purified according to the methods of Abremski, K. et al. (*J. Molec. Biol.* 150:467–486 (1981), herein incorporated by reference). NotI endonuclease, Klenow DNA polymerase, Taq polymerase and plasmids that overproduce Cre are obtained from Life Technologies, Inc., Gaithersburg Md.

The Amplification Reaction

Amplification is obtained by incubating either the circular pBR322-LOX derivative produced in Method I, or the linear pBR322-LOX derivative produced in Method II, in the presence of 10 units/ml DNA polymerase (Klenow), 1 unit/ml NotI endonuclease, Amplification Primer and Cre. A typical reaction aliquot (50 µl) contains 50 mM Tris-HCl (pH 7.5), 33 mM NaCl, 1 µg/ml pBR322-LOX derivative, 0.2 µg/ml of Amplification Primer, 50 µg/ml each of DATP, TTP, dCTP, and dGTP, and 2 µg/ml Cre. 2 mM $MgCl_2$ is added in reactions conducted with Taq polymerase. Reactions are incubated at 37–45° C. for 1–2 hours, or longer.

Analysis of Amplification Reaction

To analyze the amplification reaction, a series of control experiments are conducted. Each such experiment is conducted in a reaction volume of 50 µl. The Buffer in the experiments is 50 mM Tris-HCl (pH 7.5), 33 mM NaCl, and 50 µg/ml each of dATP, TTP, dCTP, and dGTP. All reactions are incubated for 2 hours either isothermally, or under thermocycling conditions, with 10 µl aliquots removed at 0, 30, 60 and 120 minutes. The Experimental protocol for such experiments is shown below:

Experimental Protocol

| Reagent | Experiment | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Buffer | + | + | + | + | + | + | + | + | + | + | + | + | + | + |
| 2 µg/ml Cre | + | − | + | + | + | + | − | − | + | − | − | − | − | + |
| 10 Units/ml Polymerase | | | | | | | | | | | | | | |
| Klenow | + | + | − | + | + | + | − | − | − | − | − | − | − | − |
| Taq/$MgCl_2$ | − | − | − | − | − | − | + | + | − | − | − | − | + | + |
| 1 unit/ml NotI | + | + | + | + | − | + | − | − | − | − | − | − | + | + |
| 0.2 µg/ml Amplification Primer | + | + | + | − | + | + | + | + | − | − | − | − | + | + |
| 0.2 µg/ml Target Primer | − | − | − | − | − | − | + | + | − | − | − | − | + | + |
| pBR322-LOX | | | | | | | | | | | | | | |
| 1 µg/ml | + | + | + | + | + | − | − | − | − | + | − | − | − | − |
| 10 µg/ml | − | − | − | − | − | − | − | − | + | − | + | − | − | − |
| 1 µg/ml 4 kb EcoRI-BamHI pBR322 fragment | − | − | − | − | − | − | + | + | − | − | − | + | + | + |

The results of the above-described experiments are analyzed by gel electrophoresis in order to detect amplification of DNA. Experiment 1 is a Cre-facilitated amplification reaction. Experiments 2–6 explore the effect of deleting Cre, Polymerase, Amplification Primer, NotI and Substrate, respectively, from the amplification reaction. Experiments 7–8 are designed to permit a comparison between Cre-facilitated amplification and PCR under approximately identical conditions. Experiment 7 is an amplification reaction run under isothermal conditions 37–45° C. using Taq polymerase instead of Klenow. Experiment 8 is a PCR protocol performed as described by Sambrook, J. et al. (In "Molecular Cloning A Laboratory Manual," Cold Spring Harbor Press, Cold Spring Harbor, N.Y. (1989)). Experiment 9 is a Cre control for demonstrating the capacity of the Cre to mediate recombination. Experiments 10–12 are controls to identify the nature and migration of the DNA substrates.

Experiments 13 and 14 demonstrate the capacity of Cre-mediated amplification to amplify DNA lacking lox sites. Experiments 13 and 14 are performed as follows:
1. The 3.9 kb EcoRI-BamHI linear pBR322 fragment (in Buffer) is heat denatured and then cooled to 37–45° C.
2. The Target Primer and Taq polymerase are added, and a polymerization reaction is permitted to occur for 20 minutes.
3. The reaction is then heated to heat denature any double-stranded DNA present.
4. The reaction is cooled to 37–45° C., and Amplification Primer and NotI restriction endonuclease are added. Cre is added to Experiment 14.
   Reactions 13 and 14. The reaction is then permitted to continue under isothermal conditions for 2 flours.
Evaluation of Amplification Reaction The absolute capacity of Cre-facilitated amplification methods to amplify DNA is demonstrated by a comparison of the results of Experiments 1, 14 and 10–12. The efficiency of Cre-facilitated amplification relative to PCR is demonstrated by a comparison of the results of Experiments 1, 14 and 8.

EXAMPLE 6

Isothermal Amplification of a Human Gene

The ability of the methods of the present invention to mediate DNA amplification is further illustrated with respect to the human p53 gene.

The p53 gene is a human tumor suppressor gene that comprises approximately 20 kilobases, and contains 11 exons (393 codons). The gene is located at chromosome region 17p13.105–p12. Its sequence can be obtained from the GSDB database at accession X54156. Mutations in the p53 gene are the single most common genetic alteration in human cancers. Indeed, of the more than 100,000 additional cases of colon, lung and breast cancer diagnosed each year, more than half have been reported to contain p53 mutations (Levine, A. J., *Canc. Surveys* 12:59–79 (1992); herein incorporated by reference). The majority of presently recognized p53 mutations are missense mutations tightly clustered between codons 118 and 309, the DNA binding region of the protein (Renault, B. et al., *Cancer Res.* 53:2614–2617 (1993); Ziegler, A. et al., *Proc. Natl. Acad. Sci. (U.S.A.)* 90:4216–4220 (1993)). These mutations generally result in loss of function of the p53 protein. Because of the correlation between mutations in p53 and the incidence of cancer, the p53 gene is thought to be part of the cascade necessary for the development of many tumors, and the p53 gene is believed to play a role in regulating cell growth and apoptosis.

The diversity and dispersion of mutations in the p53 gene is thus of substantial clinically relevance. Unfortunately, the large size of the p53 gene, and the large number of intervening sequences that it contains, has hampered efforts to identify additional mutations that may be associated with colon, lung or breast cancer as well as mutations that may be predictive of other types of cancer. Because the methods of the present invention are able to amplify entire human genes, they permit the amplification of the entire p53 gene of a patient in a single reaction.

The p53 gene of an individual can be amplified by incubating the gene in the presence of a Target Primer which is capable of hybridizing to the 5' terminus of one strand of the individual's p53 gene, and then in the presence of an Amplification Primer which is capable of hybridizing to the 5' terminus of the other strand of the individual's p53 gene. Both the Target Primer and the Amplification Primer have 5' termini that, if hybridized to a complementary polynucleotide, would form a double-stranded polynucleotide that contains a lox site. The Amplification Primer additionally includes a polynucleotide region containing at least one modified nucleotide residues, such that, if this polynucleotide region were hybridized to a complementary polynucleotide, a double-stranded polynucleotide would thereby be formed that would contain one or more restriction endonuclease cleavage sites that would be recognized by a restriction endonuclease but which could not (because of the presence of the modified nucleotide residue(s)) be cleaved. Rather, only that strand of the restriction site that lacked modified nucleotide residues would be cleaved.

The sequence of a suitable Target Primer is (SEQ ID NO:6):

5' tatacgaagt tatgaattca taacttcgta taatgtatgc tatacgaagt tatttcccat caagccctag ggctcc 3'

As will be recognized, nucleotides 1–13 of the Target Primer (SEQ ID NO:6) are complementary to the first 13 nucleotides of the LOX site that is present at nucleotides 20–53. Nucleotides 14–19 are an EcoRI site. Nucleotides 54–76 comprise the sequence of the nucleotides 1 through 23 of the p53 gene.

The sequence of a suitable Amplification Primer is (SEQ ID NO:7):

5' tatacgaagt tatggatcca taacttcgta tagcatacat tatacgaagt tatgcggccg cccaccctgt tcccttggaa cccaggta 3'

As will be recognized, the Amplification Primer (SEQ ID NO:7) contains a 13 base long span of nucleotides (nucleotides 1–13) that is connected to a BamHI recognition sequence (14–19). Nucleotides 20–53 are a LOX site. The initial span of nucleotides is complementary to the initial 13 nucleotides of the LOX site, such that a "loop" can form between these regions of the primer. Nucleotides 54–61 are a NotI site. Nucleotides 62–88 are complementary to nucleotides 20303 through 20277 of the human p53 gene. The underscoring of C residues in the NotI site indicates that at least one of the residues is methylated or phosphorothioated.

Amplification is achieved by incubating a sample containing the p53 gene of an individual in the presence of the Target Primer and in the presence of Klenow (or Taq) polymerase, and nucleotides. Incubation is conducted under conditions sufficient to permit the Target Primer to hybridize to the p53 template. A typical reaction aliquot (50 μl) contains 50 mM Tris-HCl (pH 7.5), 33 mM NaCl, 50 units/ml DNA polymerase (Klenow), 1 μg/ml sample DNA, 0.2 μg/ml of Target Primer, and 100 μg/ml each of dATP, TTP, dCTP, and dGTP. The polymerization reaction is monitored, and permitted to proceed until full length Target Primer extension product molecules of 20 kb have been obtained.

The reaction is then treated so as to denature the Target Primer extension product from its p53 template. It is then returned to conditions suitable hot nucleic acid hybridization and primer extension. Cre (2 µg/ml), Amplification Primer (0.2 µg/ml), and 1 unit/ml NotI endonuclease are then added to the reaction. If heat is used as the denaturant, such action will inactivate any non-thermostabile reagents present. Thus, an additional 50 units/ml of Klenow polymerase is also added to the reaction.

As will be recognized, the 3' terminus of the Amplification Primer is complementary to the 3' terminus of the full length Target Primer extension product. It thus hybridizes to that product, and the polymerase mediates both the formation of an Amplification Primer extension product, and the further extension of the Target Primer extension product until a double-stranded linear molecule is formed having lox sites on each end and a hemi-modified NotI recognition site.

The added Cre converts this linear molecule into a double-stranded circular molecule. The NotI endonuclease cleaves the target strand at the NotI restriction site, thereby generating a free 3' terminus that initiates target strand synthesis. This synthesis repairs the NotI site and thus permits its repeated cleavage, thereby "shedding" full length target strand molecules. Since the Amplification Primer is still present in the reaction, it hybridizes with these full length target strand molecules, and is extended by the polymerase to form a new double-stranded linear molecule having lox sites on each end and a hemi-modified NotI recognition site. The amplification process then continues as described above.

Amplification is demonstrated by gel electrophoresis, as described above.

EXAMPLE 7

Circularization of an Amplified Fragment of a Human Gene

The ability of the methods of the present invention to circularize a fragment of a human gene is illustrated with respect to a 1.7 kb fragment of the p53 tumor suppressor gene.

Target Primer 3aLox and Amplification Primer 1794Lox-Not were obtained by custom synthesis (Genosys). The sequence of Target Primer 3aLox is shown below as SEQ ID NO:8. Bases complementary to the p53 gene are shown in underline.

SEQ ID NO:8
ATAACTTCGT ATAATGTATG CTATACGAAG TTAT<u>TAATTC</u>

<u>TTAAAGCACC TGCACCG</u>

The sequence of Amplification Primer 1794LoxNot is shown below as SEQ ID NO:9. Bases complementary to the p53 gene are shown in underline; the NotI site (containing methylated C nucleotide residues) is shown in lowercase.

SEQ ID NO:9
ATAACTTCGT ATAGCATACA TTATACGAAG

TTATgcggc gc<u>CCATAACT AAGTAATCCA GAAAA</u>

To characterize the amplification reaction, the reaction was isolated into three "steps:" (1) the production of a double-stranded linear nucleic acid molecule in which a target polynucleotide is flanked by Lox sites (i.e., a lox site is present at each terminus of the linear molecule), and which contains a hemi-modified (NotI) restriction site between the target polynucleotide and one of the Lox sites; (2) the circularization of such a linear molecule by Cre; and (3) the nicking and amplification of such circular molecules by the restriction endonuclease and a polyw.erase.

As expected, the 3aLox and 1794LoxNot primers were found to possess significant secondary structure. Purified 1794 LoxNot primer migrated as two bands of approximately equal intensity as judged by agarose gel electrophoresis (PreCast Agarose Gels, FMC). The fastest band migrated at the approximate position of primer 3aLox. These results suggest that the 1794LoxNot primer was capable of stable self-hybridization. The primers were found to inhibit the PCR amplification mediated by BDNF primers in control reactions (PCR Amplification Kit, Gibco/BRL). Each Lox primer alone had an $IC^{50}$ of approximately 0.2 µM; a synergistic inhibition was observed when both primers were provided ($IC^{50}$ 0.02 µM).

The observed inhibition was sensitive to primer concentration and to Mg concentration. Successful PCR amplification (2 minutes at 55° C. for 35 cycles in 50–100 µl reaction volumes) of a polynucleotide fragment of the p53 gene was obtained using primers 3aLox and 1794 at 1.5–2 mM Mg; amplification was not observed at 1 mM Mg. Amplification was observed at all primer concentrations tested (0.2–0.8 µM). Optimal PCR amplification was observed at (0.2 µM primer concentration when conducted at 2 mM Mg. Such amplification forms the desired linear, double-stranded polynucleotide containing flanking recombinational sites and a hemi-modified restriction site. The experiment confirmed that primer molecules having extended 5' portions that are not complementary to any portion of an initial target molecule can serve as primers for in vitro amplification.

In order to confirm that the amplified linear molecules contained a lox site at each termini, and to confirm that such sites were in proper orientation to one another, the above-described amplified product was incubated in the presence of Cre recombinase.

Amplified product is purified by glassMax filtration according to the manufacturer's instructions, or by ethanol precipitation. Circularization reactions are performed in 30 µl volumes that contained: 13.5 µl of water, 3 µl of 10×Cre Buffer (50 mM Tris (pH 7.5), 33 mM NaCl, 10 mM $MgCl_2$), 10 mg/ml BSA (0.4 µl of a 75 µg/l solution), 12.5 µl of the purified amplified product, and (except for control reactions) 1 µl of Cre (Novagen stock solution diluted ¹⁄₁₀ in 10×Cre Buffer). Reactions are incubated for 30 minutes at 37° C., and then were stopped by heating to 70° C. for 5 minutes.

Circularization is determined by treating the reaction products with HinDIII. The amplified linear molecule is expected to have two HinDIII sites, and to thus yield three fragments (of approximately 447, 572 and 771 base pairs). If the reactants had circularized, HinDIII digestion would be expected to produce only two fragments (of approximately 572 and 1184 (=447+771−34 (a lox site eliminated through circularization) base pairs.

HinDIII digestion is performed as follows: 15 µl of Cre-treated or control reactions are incubated with 2 µl of a HinDIII solution (16 µl water, 2 µl 10×React II buffer (Life Technologies, Inc.), 2 µl HinDIII (Life Technologies, Inc.)). Digestion is stopped after a one hour incubation at 37° C. Digestion products are analyzed by electrophoresis using 0.8% agarose gels. Bands of approximately 550 and 1150 base pairs are observed in the HinDIII-treated, Cre-treated samples, but are not observed in samples incubated without Cre or without HinDIII. The experiment thus confirmed that the amplified linear product contained functional lox termini, and that Cre recombinase could mediate the circularization of the linear reaction products into the desired double-stranded circular molecule having a recombinational site, a hemi-modified restriction site and a polynucleotide fragment of a mammalian gene.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for amplifying a target polynucleotide region of an initial linear nucleic acid molecule, which method comprises the steps of:
   (A) providing a partially single-stranded, partially double-stranded nucleic acid complex, wherein a first strand of said molecule contains a polynucleotide region that is complementary in sequence to said target polynucleotide region and is a circular strand lacking termini and a second strand of said complex is non-circular and has a 3' terminus hybridized to said circular strand of said molecule; and
   (B) incubating said partially single-stranded, partially double-stranded nucleic acid molecule in the presence of a polymerase and under conditions sufficient to permit said polymerase to extend said 3' terminus of said non-circular strand in a template-dependent manner using said circular strand of said molecule as said template to thereby produce an extension product; wherein said template-dependent extension of said 3' terminus of said non-circular strand causes strand displacement of a portion of said non-circular strand and results in said amplification of said target polynucleotide region.

2. The method of claim 1, wherein said method additionally includes the step of:
   (C) incubating a primer nucleic acid molecule in the presence of the extension product of step (B) under conditions sufficient to permit said polymerase to extend the 3' terminus of said primer in a template-dependent manner using the extension product formed in step (B) as said template, to thereby produce a double-stranded linear nucleic acid molecule whose strands comprise the extension product formed in step (B) and said primer extension product.

3. The method of claim 2, wherein said method additionally includes the step of:
   (D) causing a strand of the double-stranded linear nucleic acid molecule produced in step (C) to circularize;
   (E) incubating the circularized molecule produced in step (D) with a primer oligonucleotide in the presence of a polymerase and under conditions sufficient to permit said polymerase to extend said 3' terminus of said primer in a template-dependent manner using said circular strand of said molecule produced in step (D) as said template, wherein said template-dependent extension of said 3' terminus of said primer oligonucleotide causes strand displacement of a portion of said oligonucleotide and results in said amplification of said target polynucleotide region.

4. The method of claim 1, wherein said non-circularized strand of said nucleic acid molecule contains a modified nucleotide.

5. The method of claim 4, wherein said modified nucleotide is a ribonucleotide.

6. The method of claim 4, wherein said modified nucleotide is a biotinylated nucleotide.

7. The method of claim 1, wherein said target polynucleotide region contains a mammalian gene or a polynucleotide portion thereof.

8. An in vitro polynucleotide complex comprising a first, second and third strand of DNA, wherein said first strand is circular and lacks termini and said second and third strands are non-circular and possess termini; wherein a 3' terminal region of said second strand is complementary to a region of said circular first strand, and is hybridized thereto, and a non-3' terminal region of said second strand is complementary to a region of said third strand, and is hybridized thereto.

9. The in vitro polynucleotide complex of claim 8, wherein at least one of said first, second or third strands of DNA contains a modified nucleotide.

10. The in vitro polynucleotide complex of claim 9, wherein said modified nucleotide is a biotinylated nucleotide or a ribonucleotide.

11. The in vitro polynucleotide complex of claim 9, wherein said DNA strand containing said modified nucleotide is a non-circularized DNA strand of said complex.

12. The in vitro polynucleotide complex of claim 8, wherein a DNA strand of said complex contains a nucleotide sequence of a mammalian gene or a polynucleotide portion thereof.

13. The polynucleotide complex of claim 8, wherein said hybridized 3' terminus of said second DNA strand is extended via a template-dependent polymerase reaction.

14. An in vitro polynucleotide complex comprising at least a first, a second, and a third strand of DNA, wherein:
   said first strand is circular and lacks termini;
   said second strand is non-circular, and possesses a 3' terminal region that is complementary to a region of said circular first strand, and is hybridized thereto; and
   said third strand is non-circular, and possesses a 3' terminal region that is complementary to a region of said second strand and is hybridized thereto.

15. The in vitro polynucleotide complex of claim 14, wherein at least one of said first, second or third strands of DNA contains a modified nucleotide.

16. The in vitro polynucleotide complex of claim 15, wherein said modified nucleotide is a biotinylated nucleotide or a ribonucleotide.

17. The in vitro polynucleotide complex of claim 15, wherein said DNA strand containing said modified nucleotide is a non-circularized DNA strand of said complex.

18. The in vitro polynucleotide complex of claim 14, wherein a DNA strand of said complex contains a nucleotide sequence of a mammalian gene or a polynucleotide portion thereof.

19. The polynucleotide complex of claim 14, wherein said hybridized 3' terminus of said second DNA strand and said hybridized 3' terminus of said third DNA strand are extended via a template-dependent polymerase reaction.

* * * * *